US010570189B2

(12) United States Patent
Apgar et al.

(10) Patent No.: US 10,570,189 B2
(45) Date of Patent: Feb. 25, 2020

(54) MUTEINS OF CLOTTING FACTOR VIII

(71) Applicant: Pfizer Inc., New York, NY (US)

(72) Inventors: James Apgar, Somerville, MA (US); Debra Pittman, Windham, NH (US); Mark Stahl, Lexington, MA (US); Laura Lin, Weston, MA (US); Justin Cohen, Quincy, MA (US)

(73) Assignee: PFIZER INC., New York, NY (US)

( * ) Notice: Subject to any disclaimer, the term of this patent is extended or adjusted under 35 U.S.C. 154(b) by 17 days.

(21) Appl. No.: 14/638,760

(22) Filed: Mar. 4, 2015

(65) Prior Publication Data

US 2015/0306234 A1  Oct. 29, 2015

Related U.S. Application Data

(60) Provisional application No. 61/948,186, filed on Mar. 5, 2014.

(51) Int. Cl.
*C07K 14/755* (2006.01)
*A61K 38/00* (2006.01)
*A61K 47/61* (2017.01)
*A61K 38/37* (2006.01)

(52) U.S. Cl.
CPC ............ *C07K 14/755* (2013.01); *A61K 38/00* (2013.01); *A61K 38/37* (2013.01); *A61K 47/61* (2017.08)

(58) Field of Classification Search
None
See application file for complete search history.

(56) References Cited

U.S. PATENT DOCUMENTS

| | | | |
|---|---|---|---|
| 5,859,204 | A | 1/1999 | Lollar |
| 6,838,437 | B2 | 1/2005 | Kaufman et al. |
| 6,919,311 | B2 | 7/2005 | Lenting et al. |
| 7,033,791 | B2 | 4/2006 | Lollar |
| 7,122,634 | B2 | 10/2006 | Lollar |
| 7,199,223 | B2 | 4/2007 | Bossard et al. |
| 7,211,559 | B2 | 5/2007 | Saenko et |
| 7,285,661 | B2 | 10/2007 | Sommermeyer et al. |
| 7,544,660 | B2 | 6/2009 | Lenting et al. |
| 7,615,622 | B2 | 11/2009 | Saenko et al. |
| 7,632,921 | B2 | 12/2009 | Pan et al. |
| 7,816,516 | B2 | 10/2010 | Sommermeyer et al. |
| 7,863,421 | B2 | 1/2011 | Bossard et al. |
| 7,910,661 | B2 | 3/2011 | Kozlowski et al. |
| 8,133,977 | B2 | 3/2012 | Bossard et al. |
| 8,143,378 | B2 | 3/2012 | Bossard et al. |
| 8,247,536 | B2 | 8/2012 | Bossard et al. |
| 8,519,102 | B2 | 8/2013 | Bossard et al. |
| 8,618,259 | B2 | 12/2013 | Bossard et al. |
| 8,889,831 | B2 | 11/2014 | Bossard et al. |
| 2006/0115876 | A1* | 6/2006 | Pan .................... C07K 14/755 435/69.1 |
| 2008/0064856 | A1* | 3/2008 | Warne ................ A61K 9/0019 530/383 |
| 2008/0227691 | A1* | 9/2008 | Ostergaard .......... C07K 14/755 514/1.1 |
| 2010/0311659 | A1 | 12/2010 | Saboulard et al. |
| 2011/0286988 | A1 | 11/2011 | Jiang et al. |
| 2012/0065136 | A1 | 3/2012 | Fay et al. |
| 2013/0040889 | A1* | 2/2013 | Bolt ..................... C07K 14/755 514/14.1 |

FOREIGN PATENT DOCUMENTS

| | | |
|---|---|---|
| EP | 1200105 | 3/2005 |
| EP | 2338523 | 6/2011 |
| EP | 2150561 | 10/2011 |
| EP | 2572732 | 3/2013 |
| EP | 2572733 | 3/2013 |
| NO | 2006027111 | 3/2006 |
| WO | 1994015625 | 7/1994 |
| WO | 1995018829 | 7/1995 |
| WO | 1997049725 | 12/1997 |
| WO | 0071141 | 11/2000 |
| WO | 0071714 | 11/2000 |
| WO | 2003047507 | 6/2003 |
| WO | 2004024761 | 3/2004 |
| WO | 2004024776 | 3/2004 |
| WO | 2005014050 | 2/2005 |
| WO | 2005046583 | 5/2005 |
| WO | 2006053299 | 5/2006 |
| WO | 2006103298 | 10/2006 |
| WO | 2007109221 | 9/2007 |
| WO | 2008005847 | 1/2008 |
| WO | 2009058446 | 5/2009 |
| WO | 2009140598 | 11/2009 |
| WO | 2009149303 | 12/2009 |
| WO | 2009158511 | 12/2009 |
| WO | 2011060371 | 11/2010 |
| WO | 201101242 | 1/2011 |

(Continued)

OTHER PUBLICATIONS

Coagulation factor VIII, from https://web.archive.org/web/20121022125724/http://www.uniprot.org/uniprot/P00451, Oct. 3, 2012, pp. 1-42.*
B domain-deleted coagulation factor VIII, from https://www.ncbi.nlm.nih.gov/protein/ABV90867, pp. 1-4, accessed Jun. 15, 2018.*
Mei et al., Rational design of a fully active, long-acting PEGylated factor VIII for hemophilia A treatment , Blood, 2010, vol. 116(2): 270-279.*
Baisong, M, et al, Rational design of a fully active, long acting PEGylated factor VIII for hemophilia A treatment, Blood 116(2):270-9 (2010).
Barrowcliffe et al, "Coagulation and Chromogenic Assays of Factor VIII Activity: General Aspects, Standardization, and Recommendations" Semin Thromb Hemost 28(3):247-56 (2002).

(Continued)

*Primary Examiner* — Karlheinz R. Skowronek

(57) ABSTRACT

The present disclosure provides muteins of FVIII to which a biocompatible polymer may be attached to increase the circulatory half-life of the muteins, as well as conjugates of such muteins and biocompatible polymers.

12 Claims, 6 Drawing Sheets

Specification includes a Sequence Listing.

(56) References Cited

FOREIGN PATENT DOCUMENTS

| WO | 201101267 | 1/2011 |
|---|---|---|
| WO | 201135307 | 3/2011 |
| WO | 2011060372 | 5/2011 |
| WO | 2011101284 | 8/2011 |
| WO | 2012007324 | 1/2012 |
| WO | 2012035050 | 3/2012 |
| WO | 2014147173 | 9/2014 |
| WO | 2014147175 | 9/2014 |

OTHER PUBLICATIONS

Barrowcliffe, TW, "Methodology of the Two-Stage Assay of Factor VIII (VIIIC)" Scand J Haematol 33 (Suppl 41):25-38 (1984).

Bi, et al., "Targeted disruption of the mouse factor VIII gene produces a model of haemophilia" Nature Genet 10:119-21 (1995).

Bjorkman, et al., "Population pharmacokinetics of recombinant factor VIII: the relationships of pharmacokinetics to age and body weight" Blood, 119(2):612-8 (2012).

Bjorkman, et al., "Comparative pharmacokinetics of plasma- and albumin-free recombinant factor VIII in children and adults: the influence of blood sampling schedule on observed age-related differences and implications for dose tailoring" J. Thomb. Haemo., 8:730-6 (2010).

Chalker, J.M., et al., Chemical Modification of Proteins at Cysteine: Opportunities in Chemistry and Biology, Chemistry—An Asian J., 4:630-640 (2009).

Chen et al., Lubrication at Physiological Pressures by Polyzwitterionic Brushes, Science 323, 1698-1701 (2009).

Eriksson et al., "The manufacturing process for B-domain deleted recombinant factor VIII" Semin Hematol. 38(2 Suppl 4):24-31 (2001).

Fay, "Factor VIII Structure and Function" Int. J. Hema., 83:103-8 (2006).

Fay, P.J., "Activation of factor VIII and mechanisms of cofactor action" Blood Reviews 18:1-15 (2004).

Gallimore et al, "Chromogenic peptide substrate assays and their clinical applications" Blood Rev 5:117-27 (1991).

Ganter, et al., "Coagulation Monitoring: Current Techniques and Clinical Use of Viscoelastic Point-of-Care Coagulation Devices." Anesth Analg 106(5):1366-75 (2008).

Gregoriadis et al. "Improving the therapeutic efficacy of peptides and proteins: A role for polysialic acids" Intern. J. Pharmaceutics, 300, 125-130 (2005).

Hemker, et al., "Calibrated Automated Thrombin Generation Measurement in Clotting Plasma" Pathophysiol Haemost Thromb 33:4-15 (2003).

Lee, et al., Scientific and Standardization Committee Communication, posted on ISTH website Mar. 21, 2001, Downloaded from www.isth.org/resource/group/d4a6f49a-f4ec-450f-9e0f-7be9f0c2ab2e/official_communications/fviiipharmaco.pdf on Feb. 23, 2015.

Lenting et al, "The Life Cycle of Coagulation Factor VIII in View of Its Structure and Function" Blood. 92(11): 3983-96 (1998).

Lenting et al, "Clearance mechanisms of von Willebrand factor and factor VIII" J. Thromb. Haemost. 5(7): 1353-60 (2007).

Lenting, et al., "The disappearing act of factor VIII" Haemophilia, 16:6-15 (2010).

Mackie et al, "Guidelines on the laboratory aspects of assays used in haemostasis and thrombosis" Int J Lab Hematol 35(1):1-13 (2013).

Mikaelsson et al, "Assaying the Circulating Factor VIII Activity in Hemophilia A Patients Treated with Recombinant Factor VIII Products" Semin Thromb Hemost 28:257-64 (2002).

Morfini et al, "A multicenter pharmacokinetic study of the B-domain deleted recombinant factor VIII concentrate using different assays and standards" J Thomb Haemost 1:2283-9 (2003).

Morfini, et al., "The Design and Analysis of Half-Life and Recovery Studies for Factor VII and Factor IX" Thromb. Haemost., 66(3):384-6 (1991).

Over, J., "Methodology of the One-Stage Assay of Factor VIII (vIII:C)" Scand J Haematol, 33(Suppl. 41):13-24 (1984).

Baenko, RL, et al, "Strategies towards a longer acting factor VIII", Haemophilia 12:42-51 (2006).

Thermo Scientific Crosslinking Technical Handbook (2012).

Varadi et al., "Thrombin generation assay and other universal tests for monitoring haemophilia therapy" Haemophilia 10 (Suppl. 2):17-21 (2004).

Vlot, et al., "The Half-life of Infused Factor VIII Is Shorter in Hemophiliac Patients with Blood Group 0 than in those with Blood Group A" Thromb. Haemost., 83:65-9 (2000).

White et al., "Definitions in Hemophilia Recommendation of the Scientific Subcommittee on Factor VIII and Factor IX of the Scientific and Standardization Committee of the International Society on Thrombosis and Haemostasis" Thromb Haemost 85:560 (2001).

Young, et al., "Thrombin generation and whole blood viscoelastic assays in the management of hemophilia: current state of art and future perspectives" Blood 121(11):1944-50 (2013).

PCT/IB2015/051549 International Search Report; 8 pages; dated May 26, 2015.

PCT/IB2015/051549 International Preliminary Report on Patentability; 9 pages; dated Sep. 6, 2016.

PCT/IB2015/051549 Written Opinion International Searching Authority; 8 pages; dated May 26, 2015.

\* cited by examiner

FIG. 1

Mature human coagulation factor VIII (FVIII) (excluding 19 amino acid signal peptide sequence) (SEQ ID NO:1)

```
   1 ATRRYYLGAV ELSWDYMQSD LGELPVDARF PPRVPKSFPF NTSVVYKKTL   50
  51 FVEFTDHLFN IAKPRPPWMG LLGPTIQAEV YDTVVITLKN MASHPVSLHA  100
 101 VGVSYWKASE GAEYDDQTSQ REKEDDKVFP GGSHTYVWQV LKENGPMASD  150
 151 PLCLTYSYLS HVDLVKDLNS GLIGALLVCR EGSLAKEKTQ TLHKFILLFA  200
 201 VFDEGKSWHS ETKNSLMQDR DAASARAWPK MHTVNGYVNR SLPGLIGCHR  250
 251 KSVYWHVIGM GTTPEVHSIF LEGHTFLVRN HRQASLEISP ITFLTAQTLL  300
 301 MDLGQFLLFC HISSHQHDGM EAYVKVDSCP EEPQLRMKNN EEAEDYDDDL  350
 351 TDSEMDVVRF DDDNSPSFIQ IRSVAKKHPK TWVHYIAAEE EDWDYAPLVL  400
 401 APDDRSYKSQ YLNNGPQRIG RKYKKVRFMA YTDETFKTRE AIQHESGILG  450
 451 PLLYGEVGDT LLIIFKNQAS RPYNIYPHGI TDVRPLYSRR LPKGVKHLKD  500
 501 FPILPGEIFK YKWTVTVEDG PTKSDPRCLT RYYSSFVNME RDLASGLIGP  550
 551 LLICYKESVD QRGNQIMSDK RNVILFSVFD ENRSWYLTEN IQRFLPNPAG  600
 601 VQLEDPEFQA SNIMHSINGY VFDSLQLSVC LHEVAYWYIL SIGAQTDFLS  650
 651 VFFSGYTFKH KMVYEDTLTL FPFSGETVFM SMENPGLWIL GCHNSDFRNR  700
 701 GMTALLKVSS CDKNTGDYYE DSYEDISAYL LSKNNAIEPR SFSQNSRHPS  750
 751 TRQKQFNATT IPENDIEKTD PWFAHRTPMP KIQNVSSSDL LMLLRQSPTP  800
 801 HGLSLSDLQE AKYETFSDDP SPGAIDSNNS LSEMTHFRPQ LHHSGDMVFT  850
 851 PESGLQLRLN EKLGTTAATE LKKLDFKVSS TSNNLISTIP SDNLAAGTDN  900
 901 TSSLGPPSMP VHYDSQLDTT LFGKKSSPLT ESGGPLSLSE ENNDSKLLES  950
 951 GLMNSQESSW GKNVSSTESG RLFKGKRAHG PALLTKDNAL FKVSISLLKT 1000
1001 NKTSNNSATN RKTHIDGPSL LIENSPSVWQ NILESDTEFK KVTPLIHDRM 1050
1051 LMDKNATALR LNHMSNKTTS SKNMEMVQQK KEGPIPPDAQ NPDMSFFKML 1100
1101 FLPESARWIQ RTHGKNSLNS GQGPSPKQLV SLGPEKSVEG QNFLSEKNKV 1150
1151 VVGKGEFTKD VGLKEMVFPS SRNLFLTNLD NLHENNTHNQ EKKIQEEIEK 1200
1201 KETLIQENVV LPQIHTVTGT KNFMKNLFLL STRQNVEGSY DGAYAPVLQD 1250
1251 FRSLNDSTNR TKKHTAHFSK KGEEENLEGL GNQTKQIVEK YACTTRISPN 1300
1301 TSQQNFVTQR SKRALKQFRL PLEETELEKR IIVDDTSTQW SKNMKHLTPS 1350
1351 TLTQIDYNEK EKGAITQSPL SDCLTRSHSI PQANRSPLPI AKVSSFPSIR 1400
1401 PIYLTRVLFQ DNSSHLPAAS YRKKDSGVQE SSHFLQGAKK NNLSLAILTL 1450
1451 EMTGDQREVG SLGTSATNSV TYKKVENTVL PKPDLPKTSG KVELLPKVHI 1500
1501 YQKDLFPTET SNGSPGHLDL VEGSLLQGTE GAIKWNEANR PGKVPFLRVA 1550
1551 TESSAKTPSK LLDPLAWDNH YGTQIPKEEW KSQEKSPEKT AFKKKDTILS 1600
1601 LNACESNHAI AAINEGQNKP EIEVTWAKQG RTERLCSQNP PVLKRHQREI 1650
1651 TRTTLQSDQE EIDYDDTISV EMKKEDFDIY DEDENQSPRS FQKKTRHYFI 1700
1701 AAVERLWDYG MSSSPHVLRN RAQSGSVPQF KKVVFQEFTD GSFTQPLYRG 1750
1751 ELNEHLGLLG PYIRAEVEDN IMVTFRNQAS RPYSFYSSLI SYEEDQRQGA 1800
1801 EPRKNFVKPN ETKTYFWKVQ HHMAPTKDEF DCKAWAYFSD VDLEKDVHSG 1850
1851 LIGPLLVCHT NTLNPAHGRQ VTVQEFALFF TIFDETKSWY FTENMERNCR 1900
1901 APCNIQMEDP TFKENYRFHA INGYIMDTLP GLVMAQDQRI RWYLLSMGSN 1950
1951 ENIHSIHFSG HVFTVRKKEE YKMALYNLYP GVFETVEMLP SKAGIWRVEC 2000
2001 LIGEHLHAGM STLFLVYSNK CQTPLGMASG HIRDFQITAS GQYGQWAPKL 2050
2051 ARLHYSGSIN AWSTKEPFSW IKVDLLAPMI IHGIKTQGAR QKFSSLYISQ 2100
2101 FIIMYSLDGK KWQTYRGNST GTLMVFFGNV DSSGIKHNIF NPPIIARYIR 2150
2151 LHPTHYSIRS TLRMELMGCD LNSCSMPLGM ESKAISDAQI TASSYFTNMF 2200
2201 ATWSPSKARL HLQGRSNAWR PQVNNPKEWL QVDFQKTMKV TGVTTQGVKS 2250
2251 LLTSMYVKEF LISSSQDGHQ WTLFFQNGKV KVFQGNQDSF TPVVNSLDPP 2300
2301 LLTRYLRIHP QSWVHQIALR MEVLGCEAQD LY                     2332
```

FIG. 2

B domain deleted human FVIII (SEQ ID NO:2)

```
   1 ATRRYYLGAV ELSWDYMQSD LGELPVDARF PPRVPKSFPF NTSVVYKKTL   50
  51 FVEFTDHLFN IAKPRPPWMG LLGPTIQAEV YDTVVITLKN MASHPVSLHA  100
 101 VGVSYWKASE GAEYDDQTSQ REKEDDKVFP GGSHTYVWQV LKENGPMASD  150
 151 PLCLTYSYLS HVDLVKDLNS GLIGALLVCR EGSLAKEKTQ TLHKFILLFA  200
 201 VFDEGKSWHS ETKNSLMQDR DAASARAWPK MHTVNGYVNR SLPGLIGCHR  250
 251 KSVYWHVIGM GTTPEVHSIF LEGHTFLVRN HRQASLEISP ITFLTAQTLL  300
 301 MDLGQFLLFC HISSHQHDGM EAYVKVDSCP EEPQLRMKNN EEAEDYDDDL  350
 351 TDSEMDVVRF DDDNSPSFIQ IRSVAKKHPK TWVHYIAAEE EDWDYAPLVL  400
 401 APDDRSYKSQ YLNNGPQRIG RKYKKVRFMA YTDETFKTRE AIQHESGILG  450
 451 PLLYGEVGDT LLIIFKNQAS RPYNIYPHGI TDVRPLYSRR LPKGVKHLKD  500
 501 FPILPGEIFK YKWTVTVEDG PTKSDPRCLT RYYSSFVNME RDLASGLIGP  550
 551 LLICYKESVD QRGNQIMSDK RNVILFSVFD ENRSWYLTEN IQRFLPNPAG  600
 601 VQLEDPEFQA SNIMHSINGY VFDSLQLSVC LHEVAYWYIL SIGAQTDFLS  650
 651 VFFSGYTFKH KMVYEDTLTL FPFSGETVFM SMENPGLWIL GCHNSDFRNR  700
 701 GMTALLKVSS CDKNTGDYYE DSYEDISAYL LSKNNAIEPR SFSQNPPVLK  750
 751 RHQREITRTT LQSDQEEIDY DDTISVEMKK EDFDIYDEDE NQSPRSFQKK  800
 801 TRHYFIAAVE RLWDYGMSSS PHVLRNRAQS GSVPQFKKVV FQEFTDGSFT  850
 851 QPLYRGELNE HLGLLGPYIR AEVEDNIMVT FRNQASRPYS FYSSLISYEE  900
 901 DQRQGAEPRK NFVKPNETKT YFWKVQHHMA PTKDEFDCKA WAYFSDVDLE  950
 951 KDVHSGLIGP LLVCHTNTLN PAHGRQVTVQ EFALFLTIFD ETKSWYFTEN 1000
1001 MERNCRAPCN IQMEDPTFKE NYRFHAINGY IMDTLPGLVM AQDQRIRWYL 1050
1051 LSMGSNENIH SIHFSGHVFT VRKKEEYKMA LYNLYPGVFE TVEMLPSKAG 1100
1101 IWRVECLIGE HLHAGMSTLF LVYSNKCQTP LGMASGHIRD FQITASGQYG 1150
1151 QWAPKLARLH YSGSINAWST KEPFSWIKVD LLAPMIIHGI KTQGARQKFS 1200
1201 SLYISQFIIM YSLDGKKWQT YRGNSTGTLM VFFGNVDSSG IKHNIFNPPI 1250
1251 IARYIRLHPT HYSIRSTLRM ELMGCDLNSC SMPLGMESKA ISDAQITASS 1300
1301 YFTNMFATWS PSKARLHLQG RSNAWRPQVN NPKEWLQVDF QKTMKVTGVT 1350
1351 TQGVKSLLTS MYVKEFLISS SQDGHQWTLF FQNGKVKVFQ GNQDSFTPVV 1400
1401 NSLDPPLLTR YLRIHPQSWV HQIALRMEVL GCEAQDLY               1438
```

FIG. 3A

B domain deleted FVIII heavy chain (SEQ ID NO:3)

```
  1 ATRRYYLGAV ELSWDYMQSD LGELPVDARF PPRVPKSFPF NTSVVYKKTL  50
 51 FVEFTDHLFN IAKPRPPWMG LLGPTIQAEV YDTVVITLKN MASHPVSLHA 100
101 VGVSYWKASE GAEYDDQTSQ REKEDDKVFP GGSHTYVWQV LKENGPMASD 150
151 PLCLTYSYLS HVDLVKDLNS GLIGALLVCR EGSLAKEKTQ TLHKFILLFA 200
201 VFDEGKSWHS ETKNSLMQDR DAASARAWPK MHTVNGYVNR SLPGLIGCHR 250
251 KSVYWHVIGM GTTPEVHSIF LEGHTFLVRN HRQASLEISP ITFLTAQTLL 300
301 MDLGQFLLFC HISSHQHDGM EAYVKVDSCP EEPQLRMKNN EEAEDYDDDL 350
351 TDSEMDVVRF DDDNSPSFIQ IRSVAKKHPK TWVHYIAAEE EDWDYAPLVL 400
401 APDDRSYKSQ YLNNGPQRIG RKYKKVRFMA YTDETFKTRE AIQHESGILG 450
451 PLLYGEVGDT LLIIFKNQAS RPYNIYPHGI TDVRPLYSRR LPKGVKHLKD 500
501 FPILPGEIFK YKWTVTVEDG PTKSDPRCLT RYYSSFVNME RDLASGLIGP 550
551 LLICYKESVD QRGNQIMSDK RNVILFSVFD ENRSWYLTEN IQRFLPNPAG 600
601 VQLEDPEFQA SNIMHSINGY VFDSLQLSVC LHEVAYWYIL SIGAQTDFLS 650
651 VFFSGYTFKH KMVYEDTLTL FPFSGETVFM SMENPGLWIL GCHNSDFRNR 700
701 GMTALLKVSS CDKNTGDYYE DSYEDISAYL LSKNNAIEPR SFSQNPPVLK 750
751 RHQR                                                  754
```

FIG. 3B

B domain deleted FVIII light chain (SEQ ID NO:4)

```
  1 EITRTTLQSD QEEIDYDDTI SVEMKKEDFD IYDEDENQSP RSFQKKTRHY  50
 51 FIAAVERLWD YGMSSSPHVL RNRAQSGSVP QFKKVVFQEF TDGSFTQPLY 100
101 RGELNEHLGL LGPYIRAEVE DNIMVTFRNQ ASRPYSFYSS LISYEEDQRQ 150
151 GAEPRKNFVK PNETKTYFWK VQHHMAPTKD EFDCKAWAYF SDVDLEKDVH 200
201 SGLIGPLLVC HTNTLNPAHG RQVTVQEFAL FLTIFDETKS WYFTENMERN 250
251 CRAPCNIQME DPTFKENYRF HAINGYIMDT LPGLVMAQDQ RIRWYLLSMG 300
301 SNENIHSIHF SGHVFTVRKK EEYKMALYNL YPGVFETVEM LPSKAGIWRV 350
351 ECLIGEHLHA GMSTLFLVYS NKCQTPLGMA SGHIRDFQIT ASGQYGQWAP 400
401 KLARLHYSGS INAWSTKEPF SWIKVDLLAP MIIHGIKTQG ARQKFSSLYI 450
451 SQFIIMYSLD GKKWQTYRGN STGTLMVFFG NVDSSGIKHN IFNPPIIARY 500
501 IRLHPTHYSI RSTLRMELMG CDLNSCSMPL GMESKAISDA QITASSYFTN 550
551 MFATWSPSKA RLHLQGRSNA WRPQVNNPKE WLQVDFQKTM KVTGVTTQGV 600
601 KSLLTSMYVK EFLISSSQDG HQWTLFFQNG KVKVFQGNQD SFTPVVNSLD 650
651 PPLLTRYLRI HPQSWVHQIA LRMEVLGCEA QDLY                 684
```

MUTEINS OF CLOTTING FACTOR VIII

CROSS-REFERENCE TO RELATED APPLICATIONS

This application claims the benefit of U.S. Provisional Application No. 61/948,186, filed Mar. 5, 2014, the contents of which are incorporated herein by reference in its entirety.

REFERENCE TO THE SEQUENCE LISTING

The Sequence Listing submitted concurrently herewith in computer readable form (CRF) via EFS-Web as file name PC72098A_SEQLIST_ST25.txt is incorporated herein by reference. The electronic copy of the Sequence Listing was created on Mar. 1, 2015, with a size of 69,421 bytes.

BACKGROUND OF THE INVENTION

Hemophilia A (HA) is an inherited bleeding disorder caused by mutations in the gene encoding clotting Factor VIII (FVIII). Because the gene is carried on the X chromosome, the disorder occurs almost exclusively in males with an incidence of approximately 1 in 5000 male births. Untreated, HA can result in uncontrolled bleeding resulting in death. Even if affected individuals survive bleeding episodes, bleeding into the joints can cause incapacitating joint damage, and spontaneous intracerebral bleeding can result in disabling neurological impairment.

Before the advent of FVIII replacement therapies, the disorder was highly lethal with most affected boys dying before the age of 20 from spontaneous bleeding or bleeding caused by trauma. After the discovery of plasma cryoprecipitate, containing FVIII and other clotting factors, and development of plasma-derived preparations of FVIII, the life expectancy and quality of life of HA patients improved dramatically. Although the number and severity of bleeding episodes was reduced by treatment with these products, viral contamination of the plasma supply with HIV and hepatitis viruses eventually caused devastating illnesses of their own. Eventually, the discovery of the FVIII gene and development of recombinantly produced FVIII preparations essentially eliminated the risk of viral contamination of FVIII replacement therapy.

Despite the availability of abundant supplies of recombinant FVIII for nearly two decades, replacement therapy for many HA patients remains sub-optimal. Due to the short half-life of FVIII (about 8-12 hours), severely affected HA patients require FVIII replacement every other day to maintain sufficient FVIII concentration to prophylactically prevent spontaneous bleeding. Although FVIII can be administered less frequently to stop bleeding caused by trauma, such on demand therapy is not effective to prevent spontaneous bleeding into the joints or brain which can also cause death or severe disability. Unfortunately, the frequent FVIII infusions required for prophylactic therapy is accompanied by its own problems. First, the therapy is very expensive. Second, it is associated with side effects such as septic arthritis. Third, it often requires placement of a central venous access device, which can be a source of infection and thrombosis. Fourth, patient compliance is difficult. And, fifth, frequent infusions of FVIII can cause development of antibody inhibitors to the clotting factor.

In light of the challenges associated with providing optimal prophylactic FVIII replacement therapy, there is a need in the art for ways of extending FVIII half-life after infusion. By increasing FVIII half-life, HA patients could administer the drug less frequently than is currently possible while maintaining sufficient FVIII concentration to prevent spontaneous bleeding.

Previous strategies to increase FVIII half-life have only achieved modest increases compared to wild type FVIII, but such improvements are not sufficient. Accordingly, there is a particular need in the art for new forms of FVIII having sufficiently long half-life that patients could maintain prophylaxis against spontaneous bleeding by administering the drug less frequently than is now possible.

SUMMARY OF THE INVENTION

As described further below, applicants have invented novel FVIII variants having improved properties. Among other uses, these variants can be used for attaching moieties such as biocompatible polymers to increase circulatory half-life compared to unmodified FVIII. The FVIII variants of the disclosure are therefore expected to be useful in improved methods of treating HA.

Accordingly, the present disclosure provides a modified FVIII protein comprising at least one cysteine substitution mutation at a position corresponding to one or more of the following amino acids of SEQ ID NO:1: 59, 239, 333, 336, 379, 481, 484, 486, 488, 489, 490, 492, 493, 495, 496, 497, 499, 500, 501, 507, 555, 562, 568, 571, 582, 1680, 1778, 1793, 1794, 1797, 1798, 1799, 1800, 1801, 1806, 1810, 1811, 1814, 1816, 1818, 1891, 2035, 2068, 2092, 2093, 2094, 2095, 2118, 2125, 2183, 2186, 2191, 2196, 2204, 2206, and 2212.

In some embodiments, the modified FVIII proteins further includes at least one additional substitution mutation other than cysteine selected from the group R336A, R562A, K1968A, and Y1680F.

Other embodiments include nucleic acids encoding the modified FVIII proteins of the disclosure, which may be cloned into expression vectors and then used to transfect or transform host cells for the purpose of expressing said modified FVIII proteins.

By virtue of these mutations, modified FVIII proteins of the disclosure can have improved functions compared to unmodified FVIII, such as higher expression, greater procoagulant activity, reduced immunogenicity, greater stability, reduced susceptibility to degradation, greater resistance to proteases, greater resistance to oxidation, improved ability to be activated by thrombin or other coagulation factors, improved ability to combine with other coagulation factors and components into the tenase complex, increased association or binding to vWF, improved shelf-life, reduced binding by inhibitory antibodies, reduced interaction with the low density lipoprotein receptor related protein, reduced interaction with low density lipoprotein receptor, reduced interaction with cell surface heparin sulphate proteoglycans, increased circulatory half-life, and improved pharmacokinetics.

In other embodiments, the modified FVIII proteins of the disclosure can have a moiety which may include a biocompatible polymer attached, for example, to a substituted cysteine, or elsewhere, directly or via a linker. Moieties and linkers can be attached covalently, such as to the cysteine thiol group, and in some embodiments through a reactive group in the moiety. Examples of moieties include a small organic molecule, macromolecule, antibody, antibody fragment, antigen binding domain, antibody Fc region, protein of immunologic origin, protein of immunologic function, intact clotting factor, functional fragment of a clotting factor, enzyme, nucleic acid, DNA, RNA, organometallic compound, lipid, fatty acyl chain, phospholipid, glycolipid, protein, peptide, amino acid, carbohydrate, monosaccharide, disaccharide, hydrophobic compound, hydrophilic compound, organic acid, and an organic base.

According to some embodiments, the moiety is a biocompatible polymer, such as polyethylene glycol (PEG), hydroxyalkyl starch, hydroxyethyl starch (HES), polysialic acid (PSA), a zwitterionic brush polymer, and a polyphosphorylcholine branched polymer. Biocompatible polymers can be attached, for example, to a substituted cysteine in FVIII or elsewhere in FVIII, directly or via a linker. Biocompatible polymers or linkers can be attached covalently to FVIII, such as to a cysteine thiol group, and in some embodiments via a reactive group in the polymer or linker, which in some embodiments is an electrophile and in other embodiments is a nucleophile.

As a result of attaching moieties, including for example, a biocompatible polymer, the circulatory half-life of modified FVIII can be increased, for example, at least about 2 times, 5 times, 10 times or even more, compared to unmodified FVIII.

Other embodiments include methods of treating or preventing uncontrolled bleeding in subjects suffering from a deficiency of FVIII activity by administering an effective dose of a composition containing a modified FVIII protein of the disclosure to which is attached a moiety, including for example, a biocompatible polymer. In some embodiments, the biocompatible polymer is polyethylene glycol (PEG), hydroxyalkyl starch, hydroxyethyl starch (HES), polysialic acid (PSA), a zwitterionic brush polymer, and a polyphosphorylcholine branched polymer, but other biocompatible polymers can be effective.

As a result of increasing the circulatory half-life of modified FVIII proteins, it is possible to achieve prophylaxis with substantially reduced frequency of administration. Thus, for example, effective prophylaxis against uncontrolled bleeding may be achieved with administrations occurring not more frequently than once per every 3 days, 4 days, 5 days, 6 days, 7 days, 8 days, 9 days, 10 days, 11 days, 12 days, 13 days, 2 weeks, and 3 weeks, or even longer periods.

BRIEF DESCRIPTION OF THE DRAWINGS

FIG. 1 provides the amino acid sequence of the single chain form of mature human FVIII, including the B domain (SEQ ID NO:1). The mature protein lacks a 19 amino acid signal sequence present in full length FVIII that is removed prior to secretion. The amino acids constituting that portion of the B domain missing from the B domain deleted version of FVIII illustrated in FIG. 2 are underlined. Positions of cysteine substitution mutations of the disclosure are identified by bold and underlined font. Unless otherwise indicated, numbering of FVIII amino acids described herein is based on their position in SEQ ID NO:1.

FIG. 2 provides the amino acid sequence of the single chain form of a mature partially B domain deleted version of FVIII (BDD FVIII) (SEQ ID NO:2) into which the cysteine substitutions of the disclosure were introduced and tested as described in the Examples. The mature protein lacks a 19 amino acid signal sequence removed prior to secretion. As in FIG. 1, positions of cysteine substitution mutations of the disclosure are identified by bold and underlined font.

FIG. 3A and FIG. 3B respectively provide the amino acid sequences of the heavy and light chains for the two-chain form of the BDD FVIII illustrated in FIG. 2. In certain cells expressing the single chain form of the protein, intracellular processing cleaves the protein into a heavy chain shown in FIG. 3A (SEQ ID NO:3) and a light chain shown in FIG. 3B (SEQ ID NO:4). The chains are held together non-covalently.

DETAILED DESCRIPTION

Hemophilia A

Figure 4:
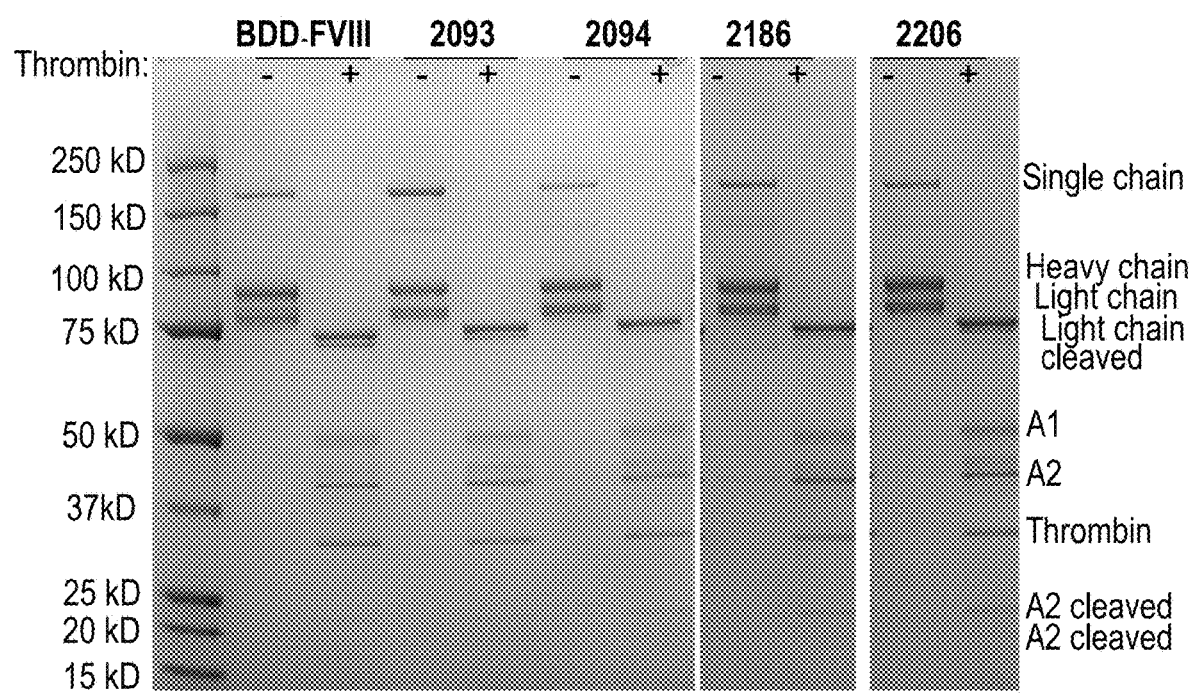
FIG. 4 provides the results of an experiment to test thrombin cleavage of selected FVIII muteins containing cysteine substitution mutations and unmutated BDD FVIII. The image is of a silver stained denaturing SDS polyacrylamide gel showing the protein bands corresponding to different proteolytic cleavage products. On the left is a protein molecular weight marker. BDD FVIII stands for B domain deleted FVIII, the positive control. The numbers (2093, 2094, 2186, and 2206) identify the position of the cysteine substitution relative to mature human FVIII of SEQ ID NO:1 (also Table 1 and FIG. 1). The plus sign (+) indicates that thrombin was added to the reaction. The minus sign (−) indicates no thrombin added. When no thrombin was added, FVIII proteins resolved to show uncleaved single chain form as well as the heavy and light chains that when non-covalently bound constitute the inactive heterodimeric form of the protein. After incubation with thrombin, the single chain and heavy and light chains disappear having been converted to expected lower molecular weight cleavage products (indicated as light chain cleaved, A1, A2, and two bands corresponding to A2 cleaved. A band corresponding to thrombin is also present.

Hemophilia A (HA) is a genetic disorder characterized by a deficiency in functional clotting Factor VIII (FVIII). Numerous mutations have been characterized that result in too little normal FVIII being produced, or that result in production of an altered protein with diminished or no activity. A list of exemplary mutations may be found at the website <http://www.uniprot.org/uniprot/P00451>. The incidence of HA in the general population is about 1 in 5000. Because it is an X-linked recessive disorder, HA mostly affects males.

Disease severity is a function of how much functional FVIII is present. In severe HA FVIII concentrations are less than 1% of normal. Patients with severe HA can suffer spontaneous bleeding. In moderate HA FVIII concentration is about 1-5% of normal. Patients with moderate HA may experience bleeding after mild trauma. Finally, in mild HA FVIII concentrations are about 5-25% normal. White et al., Thromb Haemost 85:560 (2001), which is incorporated by reference. Patients with mild HA may experience greater than normal bleeding with surgery or after experiencing major trauma. Depending on severity, HA may manifest itself with excessive uncontrolled bleeding, spontaneous or injury-induced bleeding into the brain, which can be fatal, bleeding into the joints (hemarthrosis), which can be debilitating, and soft tissue hematomas.

Factor VIII (FVIII)

Wild type FVIII precursor is a glycoprotein 2351 amino acids long, including a 19 amino acid long signal peptide.

Mature uncleaved FVIII is a single chain protein 2332 amino acids long. The amino acid sequence of mature human FVIII (lacking the signal peptide) is set forth in FIG. 1 (SEQ ID NO:1). Unless otherwise noted, this sequence serves as the reference for all numbering of amino acid residues used herein. The nucleic acid sequence encoding human FVIII is provided as SEQ ID NO:6, in which nucleotides 172-7227 encode full length FVIII including the signal peptide. Sequence analysis demonstrates that FVIII contains three so-called A domains, a B domain, and two so-called C domains. The A domains are weakly homologous to each other (about 30%) and to the A domains found in coagulation Factor V (FV) and in ceruloplasmin. The C domains are structurally related to the C domains of FV, whereas the B domain has no known homology to any other protein. FVIII additionally includes so-called acidic regions, which are short spacer regions containing Asp and Glu residues, positioned after domains A1, A2 and B. The domain structure of mature FVIII can be represented as A1-a1-A2-a2-B-a3-A3-C1-C2, where A1, A2 and A3 are the A domains, B is the B domain, C1 and C2 are the C domains and a1, a2 and a3 are the acidic regions.

With reference to FIG. 1, the FVIII domains in some embodiments correspond to the following amino acid ranges: A1 domain (1-336); a1 acidic region (337-372); A2 domain (373-710); a2 acid region (711-740); B domain (741-1648); a3 acidic region (1649-1689); A3 domain (1690-2019); C1 domain (2020-2172); C2 domain (2173-2332).

After expression in liver (in hepatocytes or sinusoidal cells), and possibly spleen, lung and kidney, mature FVIII is translocated into the endoplasmic reticulum (ER) where it undergoes N-linked glycosylation, predominantly in the A1 and B domains. The protein then travels to the Golgi apparatus where it is further modified. Among the modifications occurring within the Golgi, N-linked oligosaccharides are converted to more complex carbohydrate structures. In addition, FVIII undergoes O-linked glycosylation and sulfation at specific tyrosine residues in acidic regions. Sulfation at certain sites reportedly can affect function of FVIII as a cofactor for thrombosis or binding to von Willebrand Factor (vWF). Fay, P. J., Blood Reviews 18:1-15 (2004), which is incorporated by reference.

Before secretion from cells, mature FVIII undergoes intracellular cleavage within the Golgi to form the circulating inactive two-chain complex comprising a FVIII heavy chain (about MW 200 kD, consisting of A1-a1-A2-a2-B) and FVIII light chain (about MW 73 kD, consisting of a3-A3-C1-C2) non-covalently bound to each other. Cleavage occurs at the junction between the B and A3 domains, and at various sites within the B domain. Because cleavage within the B domain is heterogeneous, the resulting size of the heavy chain, which includes the A1 and A2 domains, is variable depending on how much B domain is removed by cleavage. Interestingly, the B domain is not required for the procoagulant activity of FVIII. By contrast, the size of the light chain, which includes A3, C1 and C2 domains is typically constant. Although heterodimeric FVIII includes two polypeptide chains (heavy and light), amino acid numbering in each refers to the numbering of amino acid residues in the mature single-chain FVIII protein sequence of SEQ ID NO:1. The heavy and light chains bind each other non-covalently through a metal ion-dependent linkage. Presence of a copper ion has been found to substantially increase inter-chain binding, but other ions, such as $Ca^{+2}$ and $Mn^{+2}$ may also influence FVIII activity.

In circulation, heterodimeric FVIII tightly binds non-covalently with another protein, von Willebrand Factor (vWF), which influences FVIII in at least two ways. First, vWF may prevent premature binding of FVIII to activated Factor IX (FIXa) and lipid membrane in the tenase complex, where FVIII acts as a FIXa cofactor. And second, vWF protects FVIII from proteolytic inactivation thereby increasing its circulatory half-life. Lenting et al, Blood. 92(11): 3983-96 (1998); Lenting et al, J. Thromb. Haemost. 5(7): 1353-60 (2007); each of which are incorporated by reference. In particular, binding by vWF may protect FVIII against cleavage by the membrane-dependent proteases activated protein C (APC) and activated Factor X (FXa). Two peptide regions in FVIII are implicated in vWF binding, one at the amino-terminal end of the intact light chain and one at the carboxy-terminal end (residues 2303-2332). Cleavage of the FVIII light chain at Arg 1689, which occurs during activation, markedly reduces vWF binding, permitting activated FVIII (FVIIIa) to participate in the tenase complex.

Circulating FVIII is activated by thrombin cleavage in the heavy chain at Arg 372 (at the a1-A2 junction) and Arg 740 (at the a2-B junction) and near the amino-terminus of the light chain at Arg 1689 to form a heterotrimer of A1-a1 (about 50 kDa), A2-a2 (about 43 kDa) and A3-C1-C2 (about 73 kDa) (amino acid numbering is with respect to mature single chain FVIII protein sequence of SEQ ID NO:1). FXa also activates FVIII, cleaving at Arg 336, Arg 372 and Arg 740, but thrombin is likely the physiologically relevant activator. After activation, FVIIIa dissociates from vWF and can be incorporated in the tenase (Xase) complex with activated Factor IX (FIXa), calcium, and phospholipid where FVIIIa functions as a cofactor for FIXa, enhancing the ability of FIXa to cleave and activate FX, forming FXa, which in turn can generate thrombin. Thrombin then cleaves fibrinogen to form fibrin monomers which then polymerize. Thrombin also activates Factor XIII (forming FXIIIa) which crosslinks fibrin polymers, stabilizing them and rendering them insoluble.

Inactivation of FVIIIa is believed to occur by several mechanisms. For example, several enzymes, including APC, FXa, FIXa and plasmin can cleave the heavy chain at position Arg 336, preceding the carboxy-terminal acidic region of the A1 domain. This cleavage releases a1 causing the A2 domain to disassociate more rapidly from the FVIIIa heterotrimer resulting in inactivation. APC can also cleave at position Arg 562 which results in loss of FIXa binding to the A2 domain, which may further destabilize the activated heterotrimer. Interestingly, spontaneous dissociation of the A2 domain from A1 and A3-C1-C2 may also result in inactivation, which may be accelerated by binding of the A2 domain to the LDL receptor related protein. Studies have also shown that interaction between FVIII and low density lipoprotein-receptor-related protein (LRP) may contribute to uptake and transport of FVIII to intracellular degradation pathways. Heparin sulphate proteoglycans (HSPG) may facilitate interaction between FVIII and LRP. LRP binds to the A2 domain in activated FVIII (Arg 484-Phe 509) and to at least three sites within the FVIII light chain (Lys 1804-Phe 1838, Lys 2065-Lys 2092, and Ser 2173-Tyr 2332). Interaction with the light chain regions, however, is completely inhibited by vWF, suggesting another mechanism by which vWF can protect FVIII from clearance.

Additional information about FVIII biology can be found in the references Fay, Blood Reviews, 18:1-15 (2004); Fay, Int. J. Hema., 83:103-8 (2006); Lenting, et al., Blood, 92(11):3983-96 (1998); and Lenting, et al., Haemophilia, 16:6-15 (2010), each of which is incorporated by reference.

As used herein, the term Factor VIII (or FVIII) refers to a protein or polypeptide having at least some procoagulant activity of wild type FVIII (whether obtained from plasma or made recombinantly) or, if initially inactive, can acquire such activity after being activated, for example and without limitation, by proteolytic cleavage. FVIII activity includes the ability to at least partially complement the procoagulant function of endogenous FVIII absent from Hemophilia A plasma or normal plasma immunodepleted of FVIII. FVIII activity also includes serving (once activated, for example, by thrombin or another protease forming FVIIIa) as a cofactor for FIXa in the tenase complex to catalyze the conversion of FX to FXa. Other procoagulant activities are possible. Assays for testing whether a protein has FVIII activity are familiar to those of ordinary skill in the art. Non-limiting examples of such assays include the single stage assay based on measuring activated partial thromboplastin time (aPTT) and the two-stage chromogenic assay. Other assays for detecting and measuring FVIII activity are possible.

FVIII includes full length FVIII (i.e., possessing a signal peptide sequence) from human or other species (for example and without limitation chimpanzee, pig, dog, rat and mouse), chimeric versions of FVIII constructed by combining one or more FVIII domains present in human FVIII with domains present in FVIII proteins from other species, and mature FVIII lacking the signal peptide sequence found in full length FVIII. A non-limiting example of mature human FVIII protein is the amino acid sequence of SEQ ID NO:1 (illustrated in FIG. 1). FVIII also includes full length FVIII lacking the methionine (Met) residue normally present at the amino terminus, mature FVIII possessing a Met at the amino terminus, or full-length or mature FVIII lacking the tyrosine (Tyr) normally found at the carboxy terminus of the protein. FVIII also includes Factor VIIIa, Factor VIII:C, and Factor VIII in association with von Willebrand factor (vWF) or FVIII disassociated from vWF.

FVIII additionally includes FVIII proteins from which the B domain has been completely or partially deleted, so-called B domain deleted FVIII (BDD FVIII). Complete deletion would remove amino acids 741-1648 as shown in FIG. 1. A non-limiting example of a human partial B domain deleted FVIII protein is the amino acid sequence of SEQ ID NO:2 (illustrated in FIG. 2), which is the amino acid sequence of the drug REFACTOR®. The nucleic acid sequence of a cDNA encoding the protein illustrated in FIG. 2 is provided in SEQ ID NO:7, which additionally encodes a 19 amino acid signal peptide from the full length FVIII protein at the amino-terminus and a 12 amino acid spacer and FLAG epitope at the carboxy-terminus.

The BDD embodiment of FIG. 2 includes 3 amino acids from the B domain amino-terminus (corresponding to amino acid positions 741 to 743 in SEQ ID NO:1) and 11 amino acids from the B domain carboxy-terminus (corresponding to amino acid positions 1638 to 1648 in SEQ ID NO:1) together forming the sequence SFSQNPPVLKRHQR (SEQ ID NO:5) corresponding to amino acid positions 741 to 754 in SEQ ID NO:2 and SEQ ID NO:3. Thus, this embodiment lacks amino acids 744-1637 as shown in FIG. 1. According to other non-limiting embodiments of BDD FVIII, as shown in FIG. 1, deletions may start with any of amino acids 741, 742, 743, 744, 745, 746, 747, 748, 749, 750, 751, 752, 753, 754, 755, and end at any of amino acids 1634, 1635, 1636, 1637, 1638, 1639, 1640, 1641, 1642, 1643, 1644, 1645, 1646, 1647, or 1648. In certain embodiments, B domain deleted FVIII lacks amino acids 740-1633, 741-1634, 742-1635, 743-1636, 744-1637, 745-1638, 746-1639, 747-1640, 748-1641, 749-1642, 750-1643, 751-1644, 747-1638, 771-1666, 868-1562, 982-1562, 760-1639, 797-1562, 741-1646, 747-1560, 741-1648, 816-1598, 741-1648, as shown in FIG. 1. Other partial B domain deleted embodiments are also possible, including some in which certain B domain amino acids are replaced with a peptide linker or non-peptide chemical linker.

Although the embodiments of FIG. 1 and FIG. 2 are shown as single chain polypeptides, it should be understood that FVIII as used herein also includes inactive heterodimers that can result from proteolytic cleavage of the single chain form (intracellularly after expression or by some other means), as well as the active (e.g., FVIIIa) heterotrimeric or other activated forms of the these proteins resulting from extracellular cleavage by thrombin, FXa or some other protease. In a non-limiting example, the BDD FVIII protein illustrated in FIG. 2 can be processed intracellularly and secreted as an inactive heterodimer comprising a heavy chain having the amino acid sequence of SEQ ID NO:3 (shown in FIG. 3A) and a light chain having the amino acid sequence of SEQ ID NO:4 (shown in FIG. 3B). In some embodiments, the heavy chain only, the light chain only, or both the heavy and the light chains in the heterodimer are truncated by one or more amino acids compared to the corresponding amino acid sequences of SEQ ID NO:3 and SEQ ID NO:4 respectively. Subunits within inactive FVIII heterodimers or activated FVIIIa heterotrimers can be held together non-covalently, as occurs naturally, or through peptide or non-peptide linkers added using recombinant or chemical means.

In other embodiments, FVIII includes proteins having FVIII activity and an amino acid sequence at least 60%, 70%, 80%, 85%, 90%, 95%, 98%, or 99% identical to the amino acid sequence of SEQ ID NO:1 or SEQ ID NO:2. Percentage amino acid sequence identity can readily be determined using the Basic Local Alignment Search Tool (BLAST) algorithm as implemented at the website of the National Center for Biotechnology Information (<http://blast.ncbi.nlm.nih.gov/Blast.cgi>), or some other sequence comparison algorithm familiar to those of ordinary skill in the art. In other embodiments, FVIII includes proteins having FVIII activity and a heavy chain with an amino acid sequence at least 60%, 70%, 80%, 85%, 90%, 95%, 98%, or 99% identical to the amino acid sequence of SEQ ID NO:3 and/or a light chain with an amino acid sequence at least 60%, 70%, 80%, 85%, 90%, 95%, 98%, or 99% identical to the amino acid sequence of SEQ ID NO:4.

As used herein, the term FVIII includes fragments of FVIII having FVIII activity and deletion mutations (including but not limited to that of the B domain) of FVIII having FVIII activity. FVIII also encompasses fusion proteins having FVIII activity, which can be constructed by fusing in frame at least one peptide or polypeptide to the amino-terminus and/or carboxy terminus of the FVIII protein (or fragment or deletion thereof), or by inserting at least one peptide or polypeptide in frame within the FVIII amino acid sequence at a location that does not abolish FVIII activity.

FVIII also encompasses naturally or non-naturally occurring variants or mutants of FVIII, including FVIII proteins comprising one or more amino acid substitutions, deletions or additions, each as compared to the wild type sequence. The amino acids can be the standard amino acids (alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine), or non-standard amino acids, such as pyrolysine, selenocysteine, ornithine or others.

FVIII also encompasses one or more types of chemical derivatives or modifications of FVIII. Chemical modifications include but are not limited to post-translational modifications, including for example, N-linked or O-linked glycosylation, sulfation, or phosphorylation. Chemical modifications also include non-natural modifications, such as conjugation with a biocompatible polymer of the disclosure, or conjugation with any other chemical. Chemical modifications can be made enzymatically or using non-enzymatic chemical reactants. In some embodiments, modifications can occur in cells, such as mammalian cells, such as CHO cells, expressing FVIII. These modifications can occur as a result of ordinary cellular processes as FVIII is expressed and, in some embodiments, secreted from the cells. In other embodiments, cells can be engineered to express enzymes intended to modify FVIII in specified ways. In yet other embodiments, FVIII can be chemically derivatized or modified using reagents and methods familiar to those of ordinary skill in the art.

In other embodiments, the term FVIII refers to the FVIII muteins described in greater detail below, either alone or in the context of or in combination with any other FVIII embodiment disclosed herein or that may be familiar to one of ordinary skill in the art.

Modified FVIII Proteins

The present disclosure provides muteins of FVIII (sometimes referred to as modified FVIII proteins) comprising substitutions (alone and in combination with other substitutions or mutations as described herein) of one or more amino acids present in the wild type protein with cysteine. FVIII amino acid positions that may be substituted with cysteine are listed in Table 1, where the numbering of the mutation positions is in reference to the amino acid sequence of SEQ ID NO:1, which is the amino acid sequence of mature human wild type FVIII protein (see also FIG. 1). Importantly, muteins of the disclosure should not be construed as being limited by SEQ ID NO:1. Rather, also included within the scope of the disclosure are cysteine substitutions at corresponding amino acids in other FVIII proteins (as that term is defined herein) that correspond to the positions in SEQ ID NO:1 that are specified by number in Table 1 and FIG. 1. FIG. 2, for example, shows the amino acid sequence of a particular human B-domain deleted (BDD) FVIII protein and identifies in bold underline font the cysteine substitution positions corresponding to those listed in Table 1. Those of ordinary skill in the art will readily be able to determine in the amino acid sequence of any other FVIII embodiment which positions correspond to those listed in Table 1. For example, one of ordinary skill can use computer software implementing amino acid sequence comparison algorithms, such as the Basic Local Alignment Search Tool (BLAST), or other algorithms, to compare SEQ ID NO:1 or SEQ ID NO:2 (or subsequences of these amino acid sequences) to any other FVIII protein amino acid sequence to find areas of similarity overall and correspondence between particular amino acids. The cysteine substitution mutations of the present disclosure are useful alone or as attachment sites for different kinds of moieties.

Without further modification, the cysteine substitution mutations are useful for a variety of purposes. For example, and without limitation, compared to unmutated FVIII the FVIII muteins of the present disclosure may be expressed at higher levels, have greater procoagulant activity, reduced immunogenicity, greater stability, reduced susceptibility to degradation, greater resistance to proteases (such as APC and FXa), greater resistance to oxidation, improved ability to be activated by thrombin or other coagulation factors, improved ability to combine with other coagulation factors and components into the tenase complex, increased association or binding to vWF, improved shelf-life, reduced binding by inhibitory antibodies, reduced interaction with the low density lipoprotein receptor related protein, reduced interaction with low density lipoprotein receptor, reduced interaction with cell surface heparin sulphate proteoglycans, increased circulatory half-life or have improved pharmacokinetics. Identification of FVIII muteins having these beneficial properties, and others, is within the skill of those ordinarily skilled in the art. Certain FVIII muteins having higher expression and/or greater procoagulant activity compared to unmutated BDD FVIII are identified in Table 1.

In other embodiments, the cysteine substitution mutations of the disclosure can serve as attachment sites for moieties where the combination of the FVIII mutein and moiety has improved performance or function and/or reduced side effects compared to FVIII muteins lacking the attached moieties. For example, and without limitation, compared to unmutated FVIII, FVIII muteins bearing moieties may have greater procoagulant activity, reduced immunogenicity, greater stability, reduced susceptibility to degradation, greater resistance to proteases (such as APC and FXa), greater resistance to oxidation, improved ability to be activated by thrombin or other coagulation factors, improved ability to combine with other coagulation factors and components into the tenase complex, increased association or binding to vWF, improved shelf-life, reduced binding by inhibitory antibodies, reduced interaction with the low density lipoprotein receptor related protein, reduced interaction with low density lipoprotein receptor, reduced interaction with cell surface heparin sulphate proteoglycans, increased circulatory half-life or have improved pharmacokinetics. Identification of combinations of FVIII muteins and moieties having these beneficial properties, and others, is within the skill of those ordinarily skilled in the art.

According to certain embodiments, moieties that can be attached directly or indirectly to the cysteine substitution mutations of the disclosure include, without limitation, naturally occurring or synthetic small organic molecules, macromolecules, antibodies, antibody fragments, antigen binding domains, antibody Fc regions, other proteins of immunologic origin or function, complete clotting factors, functional fragments of clotting factors, enzymes, nucleic acids, DNA, RNA, organometallic compounds, lipids, fatty acyl chains, phospholipids, glycolipids, proteins, peptides, amino acids, carbohydrates, monosaccharides, disaccharides, hydrophobic compounds, hydrophilic compounds, organic acids, organic bases, and others.

In other embodiments, moieties can be attached to the FVIII muteins of the present disclosure on sites other than the cysteine substitution mutations disclosed herein. For example, without limitation, moieties can be attached to amines exposed on the surface of the FVIII mutein, exposed glycosylation sites, exposed tyrosines, and other sites.

According to certain embodiments attaching a moiety, such as a biocompatible polymer, to one or more of the cysteine substitution mutations of the disclosure is useful for increasing circulatory half-life.

Without wishing to be bound by any particular theory of operation, it is believed that attaching a biocompatible polymer or other moiety to the cysteine mutations of the disclosure may be effective to increase circulatory half-life through a variety of mechanisms. One such mechanism includes eliminating or obscuring FVIII epitopes to which inhibitory antibodies are generated and bind. Regions of FVIII that interact with inhibitory antibodies include amino acids 66-75, 288-297, 306-315, 378-387, 484-509, 636-645, 648-657, 1779-1818, 2181-2243, and 2248-2319. Particular residues implicated in inhibitory antibody binding include 484, 487, 489, and 492. Another mechanism includes preventing FVIII interaction with the low density lipoprotein receptor related protein (LRP). Regions of FVIII that interact with LRP include amino acids 484-509, 1811-1818, and 2092-2093. Another mechanism includes preventing FVIII interaction with low density lipoprotein (LDL) receptor. Another mechanism includes preventing FVIII interaction with cell surface heparin sulphate proteoglycans (HSPG). A region of FVIII that interacts with heparins includes amino acids 558-566. Another mechanism includes eliminating or obscuring FVIII proteolytic cleavage sites, such as that of APC or other proteases. Particular FVIII amino acids that are involved in cleavage by APC include 336 and 562. Another possible mechanism is to increase or decrease binding by vWF. Other mechanisms by which attaching a biocompatible polymer to the cysteine mutations of the disclosure can increase circulatory half-life are possible, and the particular mechanism or mechanisms by which such improvement in half-life occurs is not intended to be limiting in any way.

FVIII mutations of the present disclosure are set forth in Table 1 along with data regarding expression levels and procoagulant activity compared to unmutated BDD FVIII. Expression was estimated by Western analysis using an antibody to FVIII. It is therefore possible that certain substitutions interfered with antibody binding such that actual expression levels may in some instances be greater than indicated.

Many of the cysteine substitution mutations tested demonstrated substantial levels of expression and procoagulant activity compared with unmutated BDD FVIII. In some cases, the mutations demonstrated expression levels or activity that was even greater than unmutated BDD FVIII (see, e.g., positions 495, 1806, 336, 1778 and 2093). The fact that many of the cysteine substitutions express well and possess substantial procoagulant activity is surprising because mutations in proteins are often associated with substantial or even complete abrogation of protein function. Even those cysteine mutations having low apparent expression and/or activity, however, may have sufficient expression or activity to usefully serve as procoagulants in the methods of the disclosure.

TABLE 1

| Mutation ID no. | FVIII cysteine substitutions in mature FVIII amino acid sequence (SEQ ID NO: 1) |
|---|---|
| 1 | F59C |
| 2 | N239C |
| 3 | P333C |
| 4 | R336C |
| 5 | P379C |
| 6 | T481C |
| 7 | R484C |
| 8 | L486C |
| 9 | S488C |
| 10 | R489C |
| 11 | R490C |
| 12 | P492C |
| 13 | K493C |
| 14 | V495C |
| 15 | K496C |
| 16 | H497C |
| 17 | K499C |
| 18 | D500C |

TABLE 1-continued

| Mutation ID no. | FVIII cysteine substitutions in mature FVIII amino acid sequence (SEQ ID NO: 1) |
|---|---|
| 19 | F501C |
| 20 | E507C |
| 21 | Y555C |
| 22 | R562C |
| 23 | S568C |
| 24 | R571C |
| 25 | N582C |
| 26 | Y1680C |
| 27 | Q1778C |
| 28 | E1793C |
| 29 | E1794C |
| 30 | R1797C |
| 31 | Q1798C |
| 32 | G1799C |
| 33 | A1800C |
| 34 | E1801C |
| 35 | F1806C |
| 36 | N1810C |
| 37 | E1811C |
| 38 | T1814C |
| 39 | F1816C |
| 40 | K1818C |
| 41 | F1891C |
| 42 | F2035C |
| 43 | F2068C |
| 44 | K2092C |
| 45 | F2093C |
| 46 | S2094C |
| 47 | S2095C |
| 48 | N2118C |
| 49 | V2125C |
| 50 | K2183C |
| 51 | S2186C |
| 52 | T2191C |
| 53 | F2196C |
| 54 | S2204C |
| 55 | S2206C |
| 56 | L2212C |

In certain embodiments of the disclosure, FVIII muteins comprise a single cysteine substitution mutation selected from Table 1. In related embodiments, a biocompatible polymer is conjugated to the cysteine so as to increase the circulating half-life of the FVIII so modified. In other embodiments, FVIII muteins comprise at least two cysteine substitution mutations from Table 1. In related embodiments, identical or different biocompatible polymers are conjugated to each cysteine to increase the circulating half-life of the FVIII so modified. Combinations of multiple cysteine mutations from Table 1 greater than two are also possible.

When two or more cysteine mutations from Table 1 are combined in the same FVIII mutein, they can be combined in different permutations, as explained in the following non-limiting examples where the mutation number refers to the mutation identification number in the left-most column of Table 1. Thus, in some embodiments, mutation 1 is combined with one or more of the other mutations numbered 2-56. In other embodiments, mutation 2 is combined with one or more of the other mutations numbered 1 or 3-56. In other embodiments, mutation 3 is combined with one or more of the other mutations numbered 1-2 or 4-56. In other embodiments, mutation 4 is combined with one or more of the other mutations numbered 1-3 or 5-56. In other embodiments, mutation 5 is combined with one or more of the other mutations numbered 1-4 or 6-56. In other embodiments, mutation 6 is combined with one or more of the other mutations numbered 1-5 or 7-56. In other embodiments, mutation 7 is combined with one or more of the other mutations numbered 1-6 or 8-56. In other embodiments, mutation 8 is combined with one or more of the other mutations numbered 1-7 or 9-56. In other embodiments, mutation 9 is combined with one or more of the other mutations numbered 1-8 or 10-56. In other embodiments, mutation 10 is combined with one or more of the other mutations numbered 1-9 or 11-56. In other embodiments, mutation 11 is combined with one or more of the other mutations numbered 1-10 or 12-56. In other embodiments, mutation 12 is combined with one or more of the other mutations numbered 1-11 or 13-56. In other embodiments, mutation 13 is combined with one or more of the other mutations numbered 1-12 or 14-56. In other embodiments, mutation 14 is combined with one or more of the other mutations numbered 1-13 or 15-56. In other embodiments, mutation 15 is combined with one or more of the other mutations numbered 1-14 or 16-56. In other embodiments, mutation 16 is combined with one or more of the other mutations numbered 1-15 or 17-56. In other embodiments, mutation 17 is combined with one or more of the other mutations numbered 1-16 or 18-56. In other embodiments, mutation 18 is combined with one or more of the other mutations numbered 1-17 or 19-56. In other embodiments, mutation 19 is combined with one or more of the other mutations numbered 1-18 or 20-56. In other embodiments, mutation 20 is combined with one or more of the other mutations numbered 1-19 or 21-56. In other embodiments, mutation 21 is combined with one or more of the other mutations numbered 1-20 or 22-56. In other embodiments, mutation 22 is combined with one or more of the other mutations numbered 1-21 or 23-56. In other embodiments, mutation 23 is combined with one or more of the other mutations numbered 1-22 or 24-56. In other embodiments, mutation 24 is combined with one or more of the other mutations numbered 1-23 or 25-56. In other embodiments, mutation 25 is combined with one or more of the other mutations numbered 1-24 or 26-56. In other embodiments, mutation 26 is combined with one or more of the other mutations numbered 1-25 or 27-56. In other embodiments, mutation 27 is combined with one or more of the other mutations numbered 1-26 or 28-56. In other embodiments, mutation 28 is combined with one or more of the other mutations numbered 1-27 or 29-56. In other embodiments, mutation 29 is combined with one or more of the other mutations numbered 1-28 or 30-56. In other embodiments, mutation 30 is combined with one or more of the other mutations numbered 1-29 or 31-56. In other embodiments, mutation 31 is combined with one or more of the other mutations numbered 1-30 or 32-56. In other embodiments, mutation 32 is combined with one or more of the other mutations numbered 1-31 or 33-56. In other embodiments, mutation 33 is combined with one or more of the other mutations numbered 1-32 or 34-56. In other embodiments, mutation 34 is combined with one or more of the other mutations numbered 1-33 or 35-56. In other embodiments, mutation 35 is combined with one or more of the other mutations numbered 1-34 or 36-56. In other embodiments, mutation 36 is combined with one or more of the other mutations numbered 1-35 or 37-56. In other embodiments, mutation 37 is combined with one or more of the other mutations numbered 1-36 or 38-56. In other embodiments, mutation 38 is combined with one or more of the other mutations numbered 1-37 or 39-56. In other embodiments, mutation 39 is combined with one or more of the other mutations numbered 1-38 or 40-56. In other embodiments, mutation 40 is combined with one or more of the other mutations numbered 1-39 or 41-56. In other embodiments, mutation 41 is combined with one or more of the other mutations numbered 1-40 or 42-56. In other embodiments, mutation 42 is combined with one or more of the other mutations numbered 1-41 or 43-56. In other embodiments, mutation 43 is combined with one or more of the other mutations numbered 1-42 or 44-56. In other embodiments, mutation 44 is combined with one or more of the other mutations numbered 1-43 or 45-56. In other embodiments, mutation 45 is combined with one or more of the other mutations numbered 1-44 or 46-56. In other embodiments, mutation 46 is combined with one or more of the other mutations numbered 1-45 or 47-56. In other embodiments, mutation 47 is combined with one or more of the other mutations numbered 1-46 or 48-56. In other embodiments, mutation 48 is combined with one or more of the other mutations numbered 1-47 or 49-56. In other embodiments, mutation 49 is combined with one or more of the other mutations numbered 1-48 or 50-56. In other embodiments, mutation 50 is combined with one or more of the other mutations numbered 1-49 or 51-56. In other embodiments, mutation 51 is combined with one or more of the other mutations numbered 1-50 or 52-56. In other embodiments, mutation 52 is combined with one or more of the other mutations numbered 1-51 or 53-56. In other embodiments, mutation 53 is combined with one or more of the other mutations numbered 1-52 or 54-56. In other embodiments, mutation 54 is combined with one or more of the other mutations numbered 1-53 or 55-56. In other embodiments, mutation 55 is combined with one or more of the other mutations numbered 1-54 or 56. In other embodiments, mutation 56 is combined with one or more of the other mutations numbered 1-55.

In other embodiments, one or more of the cysteine mutations from Table 1 can be combined in a FVIII mutein with substitutions at different positions with amino acids other than cysteine. Thus, in certain embodiments, one or more of the cysteine mutations from Table 1 can be combined with one or more substitutions at other positions that reduce or eliminate binding by inhibitory antibodies, that reduce or eliminate interaction of FVIII with LRP, reduce or eliminate interaction of FVIII with LDL receptor, reduce or eliminate FVIII interaction with heparin or HSPGs, or that prevent cleavage of FVIII by APC or other proteases responsible for the short circulatory half-life of FVIII.

According to certain embodiments, any one or more of the cysteine mutations from Table 1 can be combined in FVIII with one or more substitution mutations selected from the group consisting of Y1680F, R336A, R562A, and K1968A. The Y1680F substitution is expected to abolish vWF binding, the R336A and R562A substitutions are expected to interfere with proteolytic cleavage of FVIII by APC or FXa, and the K1968A substitution is expected to increase the stability of activated FVIII. Thus, according to certain non-limiting exemplary embodiments, FVIII muteins comprise or consist of the following combinations of two mutations in FVIII (referring to the amino acid numbering of SEQ ID NO:1): K493C+R336A, K496C+R336A, G1799C+R336A, S2094C+R336A, S2186C+R336A, S2204C+R336A, S2206C+R336A, K493C+Y1680F, K496C+Y1680F, G1799C+Y1680F, S2094C+Y1680F, S2186C+Y1680F, S2204C+Y1680F, and S2206C+Y1680F. According to yet further non-limiting exemplary embodiments, FVIII muteins comprise or consist of the following combinations of three mutations in FVIII (referring to the amino acid numbering of SEQ ID NO:1): K493C+R336A+Y1680F, K496C+R336A+Y1680F, G1799C+R336A+Y1680F, S2094C+R336A+Y1680F, S2186C+R336A+

Y1680F, S2204C+R336A+Y1680F, and S2206C+R336A+Y1680F. Additional combinations of substitution mutations in FVIII are also possible.

Mutations in FVIII, such as without limitation those listed in Table 1, can be made using site directed mutagenesis and other techniques familiar to those of ordinary skill in the art, and confirmed by sequencing.

Using tools and techniques of molecular biology familiar to those of ordinary skill in the art, nucleic acids encoding the FVIII muteins of the disclosure can be introduced into a variety of prokaryotic or eukaryotic expression vectors known in the art. Expression vectors can then be introduced into prokaryotic or eukaryotic host cells for eventual expression of the FVIII muteins. Suitable host cells are familiar to those of ordinary skill in the art and include without limitation mammalian cell lines, insect cell lines, plant cell lines, fungal cells (such as yeasts), and bacterial cells (such as *E. coli.*). Use of other host cells is also possible. Exemplary mammalian cell lines that can serve as host cells for expression of FVIII muteins includes CHO cells, COS-1 cells, BHK cells and HEK293 cells. Use of other mammalian cell lines as hosts is also possible. Host cells can be transiently or stably transfected or transformed with nucleic acids encoding the FVIII muteins of the disclosure, optionally inserted in expression vectors. In some embodiments, expression from such vectors can be constitutive or inducible.

Host cells can be grown under conditions supporting expression of the FVIII muteins of the disclosure. Muteins so produced can be purified from the host cells and/or growth media using techniques familiar to those of ordinary skill in the art. Thereafter, the purified FVIII muteins of the present disclosure can be treated chemically to attach one or more types of biocompatible polymers. The resulting conjugates can then be tested to determine whether the presence of the biocompatible polymer in the conjugates increases circulatory half-life of the modified FVIII mutein. Methods for measuring circulatory half-life of the conjugates are familiar to those of ordinary skill in the art.

In some embodiments, a conjugate of a FVIII mutein and a biocompatible polymer of the disclosure has a circulatory half-life that is increased by at least about 20%, 30%, 40%, 50%, 60%, 70%, 80%, 90%, 100%, 150%, 200%, 300%, 400%, 500%, 600%, 700%, 800%, 900%, 1000%, 1500%, 2000% or more compared to the unmutated FVIII protein used to generate the mutein or the unconjugated mutein lacking the biopolymer. In other embodiments, the circulatory half-life of a conjugate of a FVIII mutein and a biocompatible polymer of the disclosure is increased about 1.5 to 20 fold, 1.5 to 15 fold, 1.5 to 10 fold, 1.5 to 9 fold, 1.5 to 8 fold, 1.5 to 7 fold, 1.5 to 6 fold, 1.5 to 5 fold, 1.5 to 4 fold, 1.5 to 3 fold, or 1.5 to 2 fold compared to the unmutated FVIII protein used to generate the mutein or the unconjugated mutein lacking the biopolymer. In yet other embodiments, the circulatory half-life of a conjugate of a FVIII mutein and a biocompatible polymer of the disclosure is increased about 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5, 6, 7, 8, 9, 10 times or more compared to the unmutated FVIII protein used to generate the mutein or the unconjugated mutein lacking the biopolymer. In some embodiments, the circulatory half-life of a conjugate of a FVIII mutein and a biocompatible polymer of the disclosure is at least about 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, 65 hours, 70 hours, 75 hours, 80 hours, 90 hours, 100 hours, 110 hours, 120 hours, 130 hours, 140 hours, 150 hours, one week, two weeks, three weeks, or more compared to the unmutated FVIII protein used to generate the mutein or the unconjugated mutein lacking the biopolymer. In any of the foregoing embodiments, the FVIII mutein can comprise any one or more of the cysteine substitution mutations identified in Table 1 and the biocompatible polymer to which said mutein is conjugated can be a polyethylene glycol (PEG), a hydroxyalkyl starch, such as hydroxyethyl starch (HES), or another biocompatible polymer.

Factor VIII Activity

The activity, or potency, of FVIII muteins and conjugates thereof in a patient sample can be measured using a variety of bioassays known in the art, including the one-stage method, the two-stage method and the chromogenic method, which is based on the two-stage method. Morfini et al, J Thomb Haemost 1:2283-9 (2003); Mikaelsson et al, Semin Thromb Hemost 28:257-64 (2002); Mackie et al, Int J Lab Hematol 35(1):1-13 (2013); Over, J., Scand J Haematol, 33(Suppl. 41):13-24 (1984); Gallimore et al, Blood Rev 5:117-27 (1991); Barrowcliffe et al, Semin Thromb Hemost 28(3):247-56 (2002); Barrowcliffe, T W, Scand J Haematol 33(Suppl 41):25-38 (1984); Rosen et al in Triplett D A, ed. Advances in Coagulation Testing, Skokie, Ill.: College of American Pathologists, 255-260 (1986); each of which is incorporated by reference.

In one embodiment, FVIII activity can be measured using the one-stage assay. The one-stage assay measures the ability of a patient plasma sample to shorten the activated partial thromboplastin time (aPTT) of FVIII deficient plasma confirmed to contain adequate von Willebrand factor. The depleted plasma is obtained either from a patient with Hemophilia A or by immunodepletion of FVIII. The FVIII deficient plasma and test sample are preincubated with the aPTT reagent which contains a contact activator (e.g., ellagic acid, kaolin, silica, cellite) and phospholipid. Calcium chloride is added and time to fibrin clot formation is measured. FVIII concentration in the test sample is assumed to be the rate-limiting determinant of the clotting time. The result is compared with a standard curve generated from samples containing known FVIII activities (e.g., serial dilutions of a standard reference plasma) and the relative FVIII activity in the test sample is calculated.

In another embodiment, FVIII activity can be measured in a patient sample using the two-stage FVIII-clotting assay. In the first stage of the assay, FXa and prothrombinase are produced using a reaction mixture containing excess phospholipid, calcium, Factor V (from bovine serum), and clotted human serum from a patient sample as a source of FIXa and FX. Alumina hydroxide is used to adsorb prothrombin and other activated and vitamin K dependent factors to prevent clotting. The amount of functional FVIII in the sample determines the rate of FXa generation. In the second stage of the assay, pooled normal plasma is added as a source of prothrombin and fibrinogen. Clotting time is inversely proportional to the amount of FVIII in the test sample, which can be calculated by comparison to a standard curve generated using normal human plasma or other positive control.

According to another embodiment FVIII activity can be measured using a chromogenic assay which also consists of two stages. In the first stage, a test sample obtained from a patient is added to a reaction mixture containing thrombin or prothrombin, FIXa, FX, calcium, and phospholipid to produce FVIIIa, which works in concert with FIXa to activate FX. Production of FXa is assumed to be proportional to the amount of functional FVIII present in the sample. In the second stage FXa activity is measured. A chromogenic FXa peptide substrate is added and incubated for a predetermined time, after which the amount of chromogen produced is detected photometrically at the wavelength characteristic for the chromogen (e.g., 405 nm for p-nitroaniline). Chromogen concentration is assumed to be proportional to FXa activity and to FVIII activity in the test sample. FVIII activity can then be calculated by comparison to a standard curve generated using normal human plasma or other positive control.

FVIII activity can also be measured using a Thrombin Generation Assay (TGA) or using thromboelastography (TEG). TGA measures the initiation phase, activation phase and inactivation phase of thrombin generation as a function of FVIII activity. Varadi et al., Haemophilia 10 (Suppl. 2):17-21 (2004); Hemker, et al., Pathophysiol Haemost Thromb 33:4-15 (2003); each of which is incorporated by reference. Thrombin generation can be determined using the Calibrated Automated Thrombography (CAT) system (Thrombinoscope BV, Maastricht, Netherlands) and TGA reagent. TEG, and a related methodology called rotational thromboelastogram (ROTEM), measures the visco-elastic properties of whole blood clot formation under low shear stress though time. Young, et al., Blood 121(11):1944-50 (2013); Ganter, et al., Anesth Analg 106(5):1366-75 (2008), which is incorporated by reference.

The assays described above can also be modified to permit comparative testing of the activity of the different FVIII muteins and conjugates of the disclosure. For example, instead of testing patient samples, plasma from Hemophilia A patients, or normal human plasma depleted of FVIII using antibodies, can be spiked with different amounts of FVIII muteins or conjugates thereof to be tested and the assays carried out as otherwise described.

Biocompatible Polymers

Biocompatible polymers are selected so that the conjugate resulting from the combination of a FVIII mutein and biocompatible polymer exhibits increased circulatory half-life compared to the same FVIII mutein lacking the biocompatible polymer. At the same time, however, the presence of the biocompatible polymer should not unacceptably increase immunogenicity of the modified FVIII mutein, nor have unacceptably high toxicity or side effects, nor unacceptably reduce the function of the modified mutein as a procoagulant. Methods for measuring circulatory half-life and assessing immunogenicity, toxicity, side effects, and procoagulant properties of FVIII muteins modified by the addition of a biocompatible polymer are within the knowledge of the ordinarily skilled artisan.

Biocompatible polymers useful for attaching to FVIII muteins of the present disclosure to increase circulatory half-life include linear and branched polymers. Exemplary biocompatible polymers include but are not limited to polyalkylene glycols, polyethylene glycol (PEG), methoxypolyethylene glycol (mPEG), polypropylene glycol (PPG), copolymers of ethylene glycol and propylene glycol, polybutylene glycols (PBG), PEG-glycidyl ethers (Epox-PEG), PEG-oxycarbonylimidazole (CDI-PEG), polypeptides, polysaccharides, polyethers, polyamines, polycarboxylic acids, polysialic acid, polyethylene imine, polyacrylic acid, polyoxyethylated polyol, polyolefinic alcohol, polyvinylpyrrolidone, polyhydroxypropylmethacrylamide, poly (alpha)-hydroxy acid, polyvinyl alcohol (PVA), polyphosphazene, polyoxazoline, poly-N-acryloylmorpholine, polyacryloylmorpholine, 2-(methacryloyloxy)ethyl phosphorylcholine (mPC) polymers, dextrans, colominic acids, biotin derivatives, polycarboxylates, polyethylene-co-maleic acid anhydride, polystyrene-co-malic acid anhydride, heparin, albumin, celluloses, hydrolysates of chitosan, starches, glycogen, agaroses, guar gum, pullulan, inulin, xanthan gum, carrageenan, pectin, and alginic acid hydrolysates. Others are possible.

Polyethylene Glycol (PEG)

In certain embodiments, a biocompatible polymer useful for attaching to FVIII muteins of the present disclosure is polyethylene glycol, abbreviated PEG. As used herein, PEG includes any water soluble poly(ethylene oxide). In some embodiments, PEG comprises the structure —(OCH$_2$CH$_2$)$_n$— where n=2 to 4000. PEG also includes —CH$_2$CH$_2$—O(CH$_2$CH$_2$O)$_n$—CH$_2$CH$_2$— and —(OCH$_2$CH$_2$)$_n$O—. PEG also refers to polymers comprising more than 50% OCH$_2$CH$_2$-repeating subunits and less than 50% of other types of subunits. PEG includes without limitation PEG polymers of varied structures, including without limitation, branched PEG, linear PEG, forked PEG and multi-armed PEG (star-PEG) configurations.

PEG may include various terminal or end capping groups, such as without limitation a hydroxyl group, an alkoxy group, a $C_1$-$C_{20}$ alkoxy group, a substituted alkoxy group, alkenoxy group, substituted alkenoxy group, alkynoxy group, substituted alkynoxy group, aryloxy group, and substituted aryloxy group. In some embodiments, PEG is methoxypolyethylene glycol (mPEG).

PEG includes PEG polymers of any molecular weight PEG. According to certain non-limiting exemplary embodiments, PEG polymers can range from 1 kD to 100 kD, 2 kD to 80 kD, 3 kD to 70 kD, 4 kD to 60 kD, 5 kD to 50 kD, and 5 kD to 40 kD. Other ranges are possible.

Hydroxyalkyl Starch

In certain embodiments, the biocompatible polymer is hydroxyalkyl starch (HAS), which is a derivative of starch. Starches are carbohydrate polymers of many glucose subunits (also called units or monomers) joined to each other via glycosidic bonds. Starches may be linear or branched depending on the types of glycosidic bonds that are present. Specific examples of starches are amylose, which is predominantly linear although may have a few branches, amylopectin and glycogen, both of which have many more branch points than amylose. Amylose can also adopt a helical structure.

In amylose, most or all of the glucose subunits are connected to each other via α-1,4-glycosidic bonds and relatively few or no glucose subunits are connected via α-1,6-glycosidic bonds which create branch points permitting new chains of glucose subunits connected via α-1,4-glycosidic bonds to form off the main chain. By contrast, amylopectin and glycogen comprise glucose subunits linked to each other via α-1,4-glycosidic bonds as well as α-1,6-glycosidic bonds resulting in many more branches compared to amylose. In amylopectin, branching occurs at α-1,6-glycosidic bonds occurring about every 20 to 30 glucose units. Glycogen is even more branched, with branching occurring at α-1,6-glycosidic bonds occurring about every 8 to 12 glucose units. Starches can comprise a wide ranging number of glucose subunits, numbering from the dozens to many thousands. In some non-limiting embodiments, starches can comprise about 10-300,000 glucose subunits, about 50 to 200,000 glucose subunits, about 50 to 100,000 glucose subunits, about 50 to 50,000 glucose subunits, about 100 to 10,000 glucose subunits, and other ranges.

Hydroxyalkyl starch can be made from any type of starch, including without limitation amylose, amylopectin or glycogen, as well as any other type of starch known in the art. Starches from which hydroxyalkyl starches can be prepared include, but are not limited to, cereal starches and potato starches. Cereal starches include, but are not limited to, rice starches, wheat starches such as einkorn starches, spelt starches, soft wheat starches, emmer starches, durum wheat starches, or kamut starches, corn starches, rye starches, oat starches, barley starches, triticale starches, spelt starches, and millet starches such as sorghum starches or teff starches. Starches from which hydroxyalkyl starches are prepared desirably have a high content of amylopectin relative to amylose. The amylopectin content of these starches can be, for example, at least 70%, 75%, 80%, 85%, 90%, or 95% by weight, or be up to 96%, 97%, 98%, 99%, or 100% by weight. Exemplary starches having an especially high amylopectin content include certain potato starches such as waxy potato starches which can be extracted from essentially amylose-free potatoes that are either traditionally cultivated (e.g., the natural variety Eliane) or genetically modified amylopectin potato varieties, and starches of waxy varieties of cereals such as waxy corn or waxy rice.

Hydroxyalkyl starch can comprise any number of glucose subunits. For example, in some embodiments, hydroxyalkyl starch can include at least about 10, 20, 30, 40, 50, 60, 70, 80, 90, 100, 110, 120, 130, 140, 150, 160, 170, 180, 190, 200, 300, 400, 500, 600, 700, 800, 900, 1000, 1100, 1200, 1300, 1400, 1500, 2000, 3000, or more glucose subunits, and ranges between any of the foregoing numbers of glucose subunits. According to certain other embodiments, hydroxyalkyl starch contains from 1 to 2000, 5 to 1000, 10 to 500, 20 to 250, 50 to 200, or 75 to 150 glucose subunits. Other ranges are also possible.

Without limitation, hydroxyalkyl starch includes starches wherein the glucose subunits are linked to each other via α-1,4-glycosidic bonds only, in which case the starch will be completely unbranched, or a combination of α-1,4-glycosidic bonds and α-1,6-glycosidic bonds, in which case the starch will exhibit some degree of branching. Thus, hydroxyalkyl starch can demonstrate any degree of branching, from no branching to very highly branched. The degree of branching can be expressed as the ratio of the average number of α-1,4-glycosidic bonds to the average number of α-1,6-glycosidic bonds in a starch. In some embodiments, this ratio can be about 1000:1, 500:1, 400:1, 300:1, 200:1, 100:1, 90:1, 80:1, 70:1, 60:1, 50:1, 40:1, 30:1, 38:1, 37:1, 36:1, 35:1, 34:1, 33:1, 32:1, 31:1, 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, or 4:1. For amylopectin, the branching ratio ranges from about 30:1 to about 20:1, whereas for glycogen, the branching ratio ranges from about 12:1 to about 8:1. Due to their branched structure, the hydroxyalkyl starches of the disclosure have a plurality of terminal glucose monomers. In some embodiments, the number of terminal glucose monomers ranges from 2 to about 3, 4, 5, 6, 7, 8, 9, 10, 20, 30, 40, 50, 60, 70, 80, 90, 100, 150, 200, 250, 300, 350, 400, 450, 500, or more.

Hydroxyalkyl starch is a derivative of starch comprising substitution at any one or more of the hydroxyl groups of the $C_2$, $C_3$ or $C_6$ carbon atoms of any one or more of the saccharide units in the starch with at least one hydroxyalkyl group. According to certain non-limiting embodiments, hydroxyalkyl starches of the disclosure include those having the following structure:

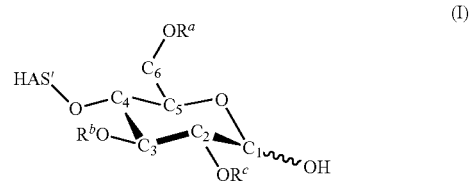

Depicted in formula (I) is the terminal saccharide unit at the reducing end of the starch molecule in the non-oxidized, hemiacetal form which may, depending on solvent or other conditions, be in equilibrium with the aldehyde form. In reference to formula (I) the abbreviations HAS' and HAS" refer to one or more additional saccharide units that, with the terminal saccharide unit, are present in the same starch molecule. In formula (I), $R^b$ and $R^c$ are each —[(CR$^1$R$^2$)$_m$O]$_n$—H, being the same or different from each other, and $R^a$ is either —[(CR$^1$R$^2$)$_m$O]$_n$—H (in which case it can be the same or different as $R^b$ and/or $R^c$) or HAS". In $R^a$, $R^b$ and $R^c$, $R^1$ and $R^2$ are independently —H or an alkyl group having 1 to 4 carbon atoms, m is independently 2 to 4, and n is independently 0 to 6, with $R^1$ and $R^2$ being the same or different from each other. When $R^a$ is —[(CR$^1$R$^2$)$_m$O]$_n$—H, HAS' is present representing additional saccharide unit(s) of the starch molecule. When $R^a$ is HAS", HAS' is also present, both HAS' and HAS" representing additional saccharide unit(s) of the starch molecule.

In some non-limiting embodiments of the disclosure, the hydroxyalkyl starch is hydroxyethyl starch (HES). Without limitation, HES can be defined using formula (I) in which $R^b$ and $R^c$ are each —(CH$_2$—CH$_2$—O)$_n$—H, being the same or different from each other, and $R^a$ is either —(CH$_2$—CH$_2$—O)$_n$—H (in which case it can be the same or different as $R^b$ and/or $R^c$) or HAS". In $R^a$, $R^b$ and $R^c$, n is independently 0 to 6. When $R^a$ is —(CH$_2$—CH$_2$—O)$_n$—H, HAS' is present representing additional saccharide unit(s) of the starch molecule. When $R^a$ is HAS", HAS' is also present, both HAS' and HAS" representing additional saccharide unit(s) of the starch molecule.

In some non-limiting embodiments of HES, HAS' is present, $R^b$ and $R^c$ are independently —H or —CH$_2$—CH$_2$—OH, and $R^a$ is independently —H, —CH$_2$—CH$_2$—OH, or HAS", HAS' and HAS" representing additional saccharide unit(s) of the starch molecule.

HAS or HES, as defined herein, are not limited to starch derivatives where only the terminal saccharide unit is derivatized by hydroxyalkyl groups, such as the groups —[(CR$^1$R$^2$)$_m$O]$_n$—H or —(CH$_2$—CH$_2$—O)$_n$—H described with respect to formula (I). Rather, HAS or HES of the disclosure include derivatized starch molecules where at least one hydroxy group present anywhere in the starch, whether in the reducing end terminal saccharide unit or some other saccharide unit in the starch, is modified with a hydroxyalkyl group, such as —[(CR$^1$R$^2$)$_m$O]$_n$—H in the case of HAS, or —(CH$_2$—CH$_2$—O)$_n$—H in the case of HES.

In certain embodiments of HAS or HES, hydroxyalkyl groups contain one hydroxyl group. In other embodiments, hydroxyalkyl groups can contain 2, 3, 4, 5, 6 or more hydroxyl groups. In yet other embodiments of HAS or HES, all hydroxyalkyl groups in the starch have the same number hydroxyl groups, for example one hydroxyl group, or hydroxyalkyl groups in the starch have different numbers of hydroxyl groups. According to some embodiments of HAS or HES, hydroxyalkyl groups may be monosubstituted or polysubstituted with heteroatoms or groups in addition to hydroxyl.

In addition, HAS or HES, as defined herein, are not limited to starch derivatives where each derivatized saccharide unit (whether the terminal residue at the reducing end or others) has the same substitutions of hydroxyalkyl moieties, but rather includes starch derivatives where substituted saccharides have distinct and different patterns of substitutions and substitutions with differently structured hydroxyalkyl moieties. According to certain embodiments, substitution with a hydroxyalkyl moiety occurs at the hydroxyl group bonded to any one or more of the $C_2$, $C_3$ or $C_6$ carbon atoms of any one or more of the saccharide units in the starch, but substitution could occur at other hydroxyl groups as well. Typically, a plurality of saccharide units will be substituted with at least one hydroxyalkyl group. In such embodiments, the substituted hydroxyl groups may be substituted with the same type or different types of hydroxyalkyl groups, such as those identified below.

In some embodiments, hydroxyalkyl starch is an ether derivative of starch. According to other embodiments, hydroxyalkyl starch includes derivatives of starch in which any one or more of the hydroxyl groups of the $C_2$, $C_3$ or $C_6$ carbon atoms of any one or more of the saccharide units in the starch is esterified. Without limitation, such esterified derivatives include unsubstituted mono- or dicarboxylic acids with 2-12 carbon atoms, 2-6 carbon atoms, or substituted derivatives thereof. In some embodiments, the ester derivatives are unsubstituted monocarboxylic acids with 2-6 carbon atoms. For other embodiments, the saccharide units are esterified with acetic acid, propionic acid, butyric acid and other mono- or dicarboxylic acids. In some embodiments esterified with dicarboxylic acids, the second carboxy group of the dicarboxylic acid is also esterified. In other embodiments containing mono- or dicarboxylic acids, the mono- or dicarboxylic acids are monosubstituted or polysubstituted. In non-limiting examples, the mono- or dicarboxylic acids are substituted with a halogen, such as fluorine, or an aryl group.

As used herein, the term alkyl appearing in the term hydroxyalkyl refers to a hydrocarbon chain, and may contain any number of carbon atoms, such as 1 to 20, 1 to 19, 1 to 18, 1 to 17, 1 to 16, 1 to 15, 1 to 14, 1 to 13, 1 to 12, 1 to 10, 1 to 9, 1 to 8, 1 to 7, 1 to 6, 1 to 5, 1 to 4, 2 to 10, 2 to 9, 2 to 8, 2 to 7, 2 to 6, 2 to 5, 2 to 4, or 1, 2, 3, 4, 5, 6, 7, 8, 9, 10, 11, 12, 13, 14, 15, 16, 17, 18, 19 or 20, or more carbon atoms. Such hydrocarbon chains may be saturated, partially unsaturated, or unsaturated, and may be linear (i.e., straight chain), branched or cyclic. Exemplary alkyl groups include but are not limited to methyl, ethyl, propyl, butyl (e.g., n-butyl, i-butyl, and t-butyl), pentyl, 1-methylbutyl, 1-ethylpropyl, 3-methylpentyl.

Alkyl can also refer to cycloalkyl as well as cycloalkylene-containing alkyl groups. Cycloalkyl refers to a saturated or unsaturated cyclic hydrocarbon chain, including bridged, fused, or spiro cyclic compounds, and may include 3 to about 12 carbon atoms, such as 3 to about 8 carbon atoms. Cycloalkylene refers to a cycloalkyl group that is inserted into an alkyl chain by bonding of the chain at any two carbons in the cyclic ring system.

In some embodiments, the alkyl moiety of the hydroxyalkyl group can itself be further substituted with any atom or group of atoms compatible with the biological function of FVIII and that does not cause unacceptable immunogenicity, toxicity or other negative side effects. Alkyl groups can be substituted in any position by one or more substituents, for example by 1, 2, 3, 4, 5 or 6 substituents. If two or more substituents are present, each substituent may be the same as or different from the at least one other substituent. Non-limiting examples of atoms or groups of atoms that may be used as substituents to modify hydroxyalkyl groups of the disclosure include hydroxyl group, alkyl group, $C_{3-8}$ cycloalkyl group (e.g., cyclopropyl or cyclobutyl groups), halogens (e.g., fluorine, chlorine, bromine, or iodine atoms), cyano group, alkoxy group (e.g., methoxy, ethoxy, or propyloxy groups), phenyl group, substituted phenyl group (on which ring substituents may be positioned at one or more of the ortho, meta, or para positions), aryl group, substituted aryl group, heteroaryl group, substituted heteroaryl group, heterocycle group or substituted heterocycle group.

Aryl means one or more aromatic rings, each of 5 or 6 core carbon atoms. Aryl includes multiple aryl rings that may be fused, as in naphthyl, or unfused, as in biphenyl. Aryl rings may also be fused or unfused with one or more cyclic hydrocarbon, heteroaryl, or heterocyclic rings. Heteroaryl is an aryl group containing from one to four heteroatoms, such as sulfur, oxygen, or nitrogen, or a combination thereof. Heteroaryl rings may also be fused with one or more cyclic hydrocarbon, heterocyclic, aryl, or heteroaryl rings. Heterocycle means one or more rings of 5-12 atoms, such as 5-7 atoms, that may be saturated, unsaturated, or partially unsaturated, with or without aromatic character, and having at least one ring atom that is not carbon. Exemplary heteroatoms include sulfur, oxygen, and nitrogen.

In certain non-limiting embodiments, the hydroxyalkyl group of the disclosure is selected from among hydroxyhexyl, hydroxypentyl, hydroxybutyl, hydroxypropyl (including 1-hydroxypropyl, 2-hydroxypropyl, 3-hydroxypropyl, 1-hydroxyisopropyl and 2-hydroxyisopropyl), hydroxyethyl (including 1-hydroxyethyl and 2-hydroxyethyl), as well as hydroxymethyl groups. In some other embodiments, just one type of these hydroxyalkyl groups is present in a hydroxyalkyl starch, whereas in other embodiments, two or more types of these hydroxyalkyl groups are present in a hydroxyalkyl starch.

In some embodiments, the hydroxyalkyl starch is hydroxyethyl starch (HES) in which the starch is amylose, amylopectin or glycogen modified by substitution at one or more glucose hydroxyl groups with a hydroxyethyl group, which may be 1-hydroxyethyl and/or the 2-hydroxyethyl group. Thus, in some HES embodiments, all hydroxyethyl groups are 1-hydroxyethyl, whereas in other HES embodiments, all hydroxyethyl groups are 2-hydroxyethyl. In some other HES embodiments, hydroxyethyl groups include both 1-hydroxyethyl and 2-hydroxyethyl, in equal proportions to each other, or in different proportions to each other.

Hydroxyalkyl starches, such as hydroxyethyl starch, can be characterized in different ways. One way to characterize HAS, such as HES, is by the molecular weight of the carbohydrate polymers. As will be familiar to one of ordinary skill in the art of polymer chemistry, molecular weight can be defined and calculated in at least two ways. According to one embodiment, molecular weight is expressed as the number average molecular weight, abbreviated Mn. In another embodiment, molecular weight is expressed as the weight average molecular weight, abbreviated Mw. Additional detail regarding how these measures differ and how to calculate Mn and Mw are found, for example, in WO 2014/147173, which is incorporated by reference.

In some embodiments, the molecular weight of HAS, such as HES, expressed as number average molecular weight or as weight average molecular weight, is about 1 kilo Daltons (kDa), 2 kDa, 3 kDa, 4 kDa, 5 kDa, 6 kDa, 7 kDa, 8 kDa, 9 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 100 kDa, 105 kDa, 110 kDa, 115 kDa, 120 kDa, 125 kDa, 130 kDa, 135 kDa, 140 kDa, 145 kDa, 150 kDa, 155 kDa, 160 kDa, 165 kDa, 170 kDa, 175 kDa, 180 kDa, 185 kDa, 190 kDa, 195 kDa, 200 kDa, 210 kDa, 220 kDa, 230 kDa, 240 kDa, 250 kDa, 260 kDa, 270 kDa, 280 kDa, 290 kDa, 300 kDa, 350 kDa, 400 kDa, 450 kDa, 500 kDa, 550 kDa, 600 kDa, 650 kDa, 700 kDa, 750 kDa, 800 kDa, 850 kDa, 900 kDa, 1000 kDa, or higher, and ranges among and between these values. In other embodiments, HAS, such as HES, has a molecular weight (Mn or Mw) ranging from about 500 Da to about 300 kDa, about 1 kDa to about 200 kDa, about 2 kDa to about 100 kDa, about 5 kDa to about 50 kDa, or about 10 kDa to about 40 kDa. Other ranges are also possible.

Hydroxyalkyl starch, such as hydroxyethyl starch, can be monodisperse or polydisperse. Monodispersity means that the HAS, such as HES, is of uniform size, or very small deviation from the mean. Polydispersity means that the HAS, such as HES, is non-uniform, or has a relatively large deviation from the mean. In some embodiments, the deviation is about 1%, 2%, 3%, 4%, 5%, 6%, 7%, 8%, 9%, 10%, 11%, 12%, 13%, 14%, 15%, 20%, 25%, or 30% of the mean molecular weight. In other embodiments, the deviation can be expressed as plus or minus (±) 10 Daltons (Da), 50 Da, 100 Da, 150 Da, 200 Da, 250 Da, 300 Da, 350 Da, 400 Da, 450 Da, 500 Da, 650 Da, 700 Da, 750 Da, 800 Da, 850 Da, 900 Da, 950 Da, 1,000 Da, 2,000 Da, 3,000 Da, 4,000 Da, 5,000 Da, 6,000 Da, 7,000 Da, 8,000 Da, 9,000 Da, 10,000 Da, 11,000 Da, 12,000 Da, 13,000 Da, 14,000 Da, 15,000 Da, 20,000 Da, 25,000 Da, 30,000 Da, 40,000 Da, 45,000 Da, 50,000 Da, 55,000 Da, 60,000 Da, 65,000 Da, 70,000 Da, 75,000 Da, 80,000 Da, 85,000 Da, 90,000 Da, 95,000 Da, or 100,000 Da, from the mean molecular weight.

Another way to characterize HAS, such as HES, is the degree of molar substitution (MS), which is the average number of hydroxyalkyl groups, such as hydroxyethyl groups, per glucose monomer. In some embodiments, the molar substitution is about 0.10, 0.20, 0.30, 0.40, 0.50, 0.60, 0.70, 0.80, 0.90, 1.00, 1.10, 1.30, 1.40, 1.50, 1.60, 1.70, 1.80, 1.90, 2.00, 2.10, 2.20, 2.30, 2.40, 2.50, 2.60, 2.70, 2.80, 2.90, or 3.00 hydroxyethyl groups per glucose, and ranges among and between these values. In some embodiments, the degree of molar substitution may vary from the mean by about 1%, 2%, 3%, 4%, 5%, 6%, 7%, 8%, 9%, 10%, 11%, 12%, 13%, 14%, 15%, 20%, 25%, 30%, 35%, 40%, 50%, 55%, 60%, or more.

Yet another way to characterize HAS, such as HES, is to express the ratio at which the average glucose subunit in the polymer is substituted at the C2 and C6 positions, i.e., the C2/C6 ratio. In some embodiments, the C2/C6 ratio is about 0.001, 0.01, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 5.5, 6.0, 6.5, 7.0, 7.5, 8.0, 8.5, 9.0, 9.5, 10.0, 100, 1000, or more, and ranges among and between these values.

The characteristics of mean molecular weight, degree of molar substitution and C2/C6 ratio can each be varied independently in particular preparations of hydroxyalkyl starch, such as hydroxyethyl starch, according to knowledge of those ordinarily skilled in the art. Non-limiting examples of HES embodiments characterized according to specific combinations of molecular weight and molar substitution include Mn~500 kDa and MS ranging from 0.5 to 1.5, such as 0.5, 0.6, 0.7, 0.8, 0.9, 1.0, 1.1, 1.2, 1.3, 1.4, or 1.5; Mn~200 kDa and MS ranging from 0.5 to 1.5, such as 0.5, 0.6, 0.7, 0.8, 0.9, 1.0, 1.1, 1.2, 1.3, 1.4, or 1.5; Mn~135 kDa and MS ranging from 0.5 to 1.5, such as 0.5, 0.6, 0.7, 0.8, 0.9, 1.0, 1.1, 1.2, 1.3, 1.4, or 1.5; Mn~100 kDa and MS ranging from 0.5 to 1.5, such as 0.5, 0.6, 0.7, 0.8, 0.9, 1.0, 1.1, 1.2, 1.3, 1.4, or 1.5; Mn~65 kDa and MS ranging from 0.5 to 1.5, such as 0.5, 0.6, 0.7, 0.8, 0.9, 1.0, 1.1, 1.2, 1.3, 1.4, or 1.5. According to other non-limiting examples, each of the foregoing HES embodiments can additionally be characterized as having a C2/C6 ratio in the range of 1 to 50, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, 45, 46, 47, 48, 49, or 50. In some embodiments, HES conjugated to a FVIII mutein of the disclosure has a single set of characteristics (i.e., unique combination of molecular weight, molar substitution, and optionally C2/C6 ratio), whereas in other embodiments, HES with two or more sets of characteristics can be conjugated to the FVIII muteins of the disclosure. Techniques for determining the mean molecular weight, molar substitution and C2/C6 ratio are familiar to those of ordinary skill in the art.

Polysialic Acid and Other Polymers

In some other embodiments of biocompatible polymers, a biocompatible polymer is polysialic acid (PSA) including, without limitation, α-2,8-linked polysialic acid. The properties of such polymers are discussed further in G. Gregoriadis, et al., Improving the therapeutic efficiency of peptides and proteins: a role for polysialic acids, Int. J. Pharmaceutics, 300, 125-130 (2005), which is incorporated by reference. In certain non-limiting embodiments, PSA includes from 2 to about 80 sialic acid subunits. Other sizes are also possible. In some embodiments, PSA can be homopolymeric, consisting of sialic acid subunits linked only by α-2,8-linkages, whereas in other embodiments, PSA can be heteropolymeric, for example comprising sialic acid subunits linked by alternating α-2,8-linkages and α-2,9-linkages.

In yet other embodiments, a biocompatible polymer is a zwitterionic brush polymer, for example and without limitation, a poly-phosphorylcholine branched polymer. The properties of such polymers are discussed further in M. Chen et al., Lubrication at Physiological Pressures by Polyzwitterionic Brushes, Science 323, 1698-1701 (2009), which is incorporated by reference.

Conjugates of FVIII Muteins and Biocompatible Polymers

The disclosure provides conjugates comprising a mutein of FVIII and a biocompatible polymer. In certain embodiments, the FVIII muteins are FVIII proteins comprising one or more of the cysteine substitutions disclosed herein and the biocompatible polymer is polyethylene glycol (PEG) or hydroxyalkyl starch (HAS), for example hydroxyethyl starch (HES), or some other biocompatible polymer. According to some embodiments, the biocompatible polymer is covalently coupled to the thiol sulfur atom of the one or more substituted cysteines of a mutein of the disclosure. In some embodiments, the linkage is a direct one whereas in other embodiments the biocompatible polymer is attached indirectly through a spacer and/or a linker interposed between the thiol sulfur and the polymer, in which case the mutein and polymer are each bonded directly to the spacer and/or linker.

Linkers, also called cross-linkers, are molecules bearing one or more chemical reactive groups for attachment at certain sites on a biocompatible polymer, and/or to a mutein of the disclosure, for example to a thiol of a substituted cysteine. As will be appreciated by those of ordinary skill, after reactions have been carried out to effect attachment of a linker to a polymer, to a mutein, or to both a polymer and mutein, one or more atoms from the linker may remain as part of the modified polymer, modified mutein, or conjugate comprising the attached polymer and mutein. Linkers can optionally include a spacer which is an additional atom or atoms serving to separate reactive groups in a bifunctional (or higher, e.g., trifunctional) linker, or that separate a reactive group of a linker from an attachment site on a polymer or mutein, or that separate a polymer and mutein in a conjugate. Spacers can be any length and contain their own functional groups.

Conjugates can be made according to the knowledge of those ordinarily skilled in the art. In some embodiments, a biocompatible polymer is coupled to a linker with a reactive group capable of attaching to the thiol sulfur of a substituted cysteine. In a subsequent step, the polymer-linker combination is coupled to the cysteine. In other embodiments, a mutein is coupled to a linker via a cysteine thiol group where the linker has a reactive group capable of attaching to corresponding group of the polymer. In a subsequent step, the mutein-linker combination is coupled to the polymer. In some embodiments, a reactive group is first created chemically at a predetermined site on the polymer to enable coupling between the group and a linker in a subsequent reaction.

In some embodiments, the linker is bifunctional, meaning it has two reactive groups and optionally a spacer between them. One of the reactive groups is capable of reacting with a corresponding group on a polymer whereas the other reactive group is capable of reacting with the thiol of the substituted cysteine of a mutein. The bifunctional linker can be reacted with the polymer first, followed by reaction of the polymer-linker combination with the mutein. Alternatively, the bifunctional linker can be reacted with the mutein first, followed by reaction of the mutein-linker with the polymer. In some embodiments reaction conditions may be chosen so that the polymer, bifunctional linker and mutein can be reacted with each other simultaneously to form a conjugate. In some embodiments, a reactive group is first created chemically at a predetermined site on the polymer to enable coupling between the group and a linker in a subsequent reaction. In some embodiments, bifunctional linkers are homobifunctional, possessing two of the same type of reactive group. In other embodiments, bifunctional linkers are heterobifunctional, possessing different reactive groups. Use of linkers with more than two reactive groups is also possible, although use of protecting groups to prevent unwanted side reactions at certain reactive groups may be desirable.

In some embodiments, linkers and spacers can be designed with physiologically cleavable linkages. A physiologically cleavable linkage is one that reacts with water (i.e., is hydrolyzed) under physiological conditions, the rate depending on the particular atoms, bonds, substituents if present and conditions. Non-limiting examples include esters (e.g., carboxylate ester, phosphate ester, carbonate ester, orthoester, thiolester), carbamate, sulfate, phosphate anhydride, acetal, ketal, acyloxyalkyl ether, imine, hydrazone, amide, urethane, peptide and oligonucleotide linkages. Linkers and spacers can also be designed with enzymatically cleavable linkages, such as groups that can be recognized and cleaved by esterases, proteases, phosphatases, nucleases, and other enzymes. Linkers or spacers can be designed to include specific amino acid sequences cleavable by proteases recognizing such sites.

Methods and reagents for synthesizing linkers with particular reactive groups are within the knowledge of those ordinarily skilled in the art, as are methods and reagents for reacting polymers, linkers and muteins to form conjugates of the disclosure. For example, in some embodiments, before a FVIII mutein is reacted with a linker or polymer-linker combination, the cysteine thiol is first reduced using a reducing agent such as DTT, TCEP, or another suitable reducing agent familiar to those of ordinary skill in the art. In addition, potentially reactive side groups of a mutein (for example, a thiol of a native cysteine residue), polymer or linker, can be protected to prevent unwanted side reactions from occurring during later reaction steps required to produce the desired conjugate. Later, after the conjugate or a desired intermediate has been produced, such protecting groups can be removed according the knowledge of those ordinarily skilled in the art.

Typically, though not necessarily, conjugates are purified away from leaving groups and other impurities from the chemical reaction or reactions used to make modified polymers and/or muteins, as well as the final conjugate product. Non-limiting examples of a purification step include gel filtration, ultrafiltration, dialysis, and precipitation, but other methods can be used as well, such as ion exchange chromatography, immunoaffinity chromatography (e.g., with antibodies against FVIII), or other purification methods. In some embodiments, additional purification steps may be used, for example, to purify desired intermediates from undesired reactants before proceeding to the next reaction in a multistep reaction scheme for making conjugates of the disclosure.

According to certain non-limiting embodiments, a thiol reactive polymer useful for conjugating to a substituted cysteine can be produced by reacting a polymer having an electrophilic reactive group with a linker having a nucleophilic reactive group (for reacting with the polymer's electrophile) and a thiol reactive group (for reacting with the substituted cysteine's thiol). The polymer-electrophile can be represented by the formula POLY-$W_{0,1}$-E, where POLY stands for a polymer such as PEG, HAS or HES, W stands for a spacer, which can be absent (0) or present (1), and E stands for an electrophile, i.e., electrophilic reactive group. The linker can be represented by the formula NU-Y-T, where NU stands for a nucleophile, Y stands for a group, moiety, or spacer interposed between NU and T, and T stands for a thiol-reactive group, or protected thiol (i.e., —S with additional atoms). After reacting the electrophilically active polymer with the linker, the resulting thiol reactive polymer can be represented by the formula POLY-$W_{0,1}$-X-Y-T, where POLY, W, Y and T are defined as before, and X stands for the moiety formed by the reaction between the electrophile (E) and nucleophile (NU), not including any leaving group or groups that may have been formed during the reaction. Once synthesized, the thiol reactive polymer can be reacted with a FVIII mutein comprising a substituted cysteine (represented by the formula S-FVIII, where S is the cysteine thiol and FVIII stands for the remainder of the Factor VIII mutein) to produce a conjugate of the polymer and mutein. The conjugate can be represented by the formula POLY-$W_{0,1}$-X-Y-Z-FVIII, where POLY, W and Y are defined as before, and Z stands for the moiety formed by the reaction between the thiol reactive group of the polymer, T, and the mutein's cysteine thiol, S, not including any leaving group(s).

In other embodiments, the position of electrophile and nucleophile can be reversed, such that the nucleophile is initially associated with the polymer (represented as POLY-$W_{0,1}$-NU) and the electrophile is associated with the linker (represented as E-Y-T). In these embodiments, reaction of the nucleophilically active polymer with the linker can yield a similar thiol-reactive polymer as before (represented as POLY-$W_{0,1}$-X-Y-T), but where X results from reaction of the differently situated nucleophile and electrophile.

Electrophile refers to an ion, atom, or collection of atoms that may be ionic, having an electrophilic center, i.e., a center that is electron seeking and capable of reacting with a nucleophile. In some embodiments, the electrophile is naturally present as part of the polymer without further modification. In other embodiments, the electrophile is added by chemically modifying the polymer, optionally including a spacer W. Where the electrophile is naturally part of the polymer, then no spacer is present.

Exemplary, non-limiting electrophiles include carboxylic acid or an activated carboxylic acid derivative, amide, carboxylic acid ester, carbonate ester, carbonic acid, acid halide, activated esters (e.g., N-hydroxysuccinimidyl (NHS) ester or 1-hydroxybenzotriazolyl ester), active carbonates (e.g. N-hydroxysuccinimidyl carbonate, para-nitrophenylcarbonate, and 1-hydroxybenzotriazolyl carbonate), acetal, hemi-acetal, aldehyde, aldehyde hydrate, active anhydrides such as acid anhydrides, aryl halide, ketone, isocyanate, isothiocyanate, imidoester, pentafluorophenyl (PFP), and others.

The spacer W, when present, can in certain non-limiting embodiments be $C_1$-$C_{10}$ alkyl (such as a methylene group), $C_1$-$C_{10}$ substituted alkyl, linear lower alkyl, branched lower alkyl, or other groups, including non-alkyl groups.

Nucleophile refers to an ion or atom or collection of atoms that may be ionic, having a nucleophilic center, i.e., a center that is seeking an electrophilic center and capable of reacting with an electrophile. In some embodiments, the nucleophile NU can be amino (primary, secondary or other), hydroxy, thiol, imino, or thioester groups, or others known to those of ordinary skill in the art.

According to certain non-limiting embodiments, NU can be one of the following groups: $CH_3$—NH—, $CH_3$—$CH_2$—NH—, $CH_3$—$CH_2$—$CH_2$—NH—, $(CH_3)_2$—CH—NH—, $H_2N$—, $H_2N$—O—, $H_2N$—NH—, $H_2N$—NH—(C=O)—, $H_2N$—NH—(C=O)—NH—, $H_2N$—NH—(C=O)—O— and $H_2N$—NH—$SO_2$—.

Group Y may be linear, branched or some other configuration. In some embodiments, Y groups can be alkyl (branched or non-branched), substituted alkyl, alkenyl, substituted alkenyl, alkylaryl, substituted alkylaryl, arylalkyl, substituted arylalkyl, aryl, substituted aryl, heteroaryl group, substituted heteroaryl group, cycloalkyl, substituted cycloalkyl, alkylenecycloalkyl, substituted alkylenecycloalkyl, alkylene, substituted alkylene, cycloalkylene, or substituted cycloalkylene, and may include such groups as methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), 2-methylpropyl, and other groups as well.

The term "substituted" in the context of group Y refers to replacement of some atom, usually but not necessarily H, with a heteroatom or group. Groups (such as alkyl, etc.) can be substituted with multiple substituents, for example, 1, 2, 3, 4, 5 or 6 substituents. If two or more substituents are present, each substituent may be the same as or different from the at least one other substituent. Non-limiting examples of substituents includes groups such as alkyl, aryl, alkenyl, alkynyl, fluorine, hydroxyl, alkylcarbonyloxy, arylcarbonyloxy, alkoxycarbonyloxy, aryloxycarbonyloxy, carboxyl, alkoxycarbonyl, aminocarbonyl, alkylaminocarbonyl, dialkylaminocarbonyl, alkoxy, phosphate, phosphonato, phosphinato, tertiary amino, acylamino, including alkylcarbonylamino, arylcarbonylamino, carbamoyl, ureido, nitro, alkylthio, arylthio, amide, sulfate, alkylsulfinyl, sulfonate, sulfonamido, trifluoromethyl, cyano, azido, carboxymethylcarbamoyl (i.e., the group —C(=O)(—NH—$CH_2$—COOH)), cycloalkyl (e.g., cyclopentyl or cyclohexyl), heterocycloalkyl (e.g., morpholino, piperazinyl or piperidinyl), alkylaryl, arylalkyl and heteroaryl, examples of the latter of which include but are not limited to benzodioxolyl, pyrrolyl, furanyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, benzoxazolyl, benzodioxazolyl, benzothiazolyl, benzoimidazolyl, benzothiophenyl, methylenedioxyphenyl, napthyridinyl, quinolinyl, isoquinolinyl, indolyl, benzofuranyl, purinyl, benzofuranyl, deazapurinyl, and indolizinyl groups.

If linear, Y can be different lengths, for example, ranging from about 1 to about 20 atoms, from about 2 to about 15 atoms, from about 2 to about 10 atoms, from about 1 to about 6 atoms, or some other length, including longer than 20 atoms.

Non-limiting examples of Y groups include the following structures: —$CH_2$—, —$CH_2$—$CH_2$—, —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH_2$—$CH_2$—$CH_2$—$CH_2$—$CH_2$—$CH_2$—, —$CH_2$—$CH_2$—$CH_2$—$CH_2$—$CH_2$—$CH_2$—$CH_2$—, —$CH_2$—$CH_2$—$CH_2$—$CH_2$—$CH_2$—$CH_2$—$CH_2$—$CH_2$—, —$CH_2$—$CH_2$—$CH_2$— $CH_2$—$CH_2$—$CH_2$—$CH_2$—$CH_2$—, —$CH_2$—$CH_2$—$CH_2$—$CH_2$—$CH_2$—$CH_2$—$CH_2$—$CH_2$—$CH_2$—, —$CH_2$—$CH_2$—$CH_2$— $CH_2$—$CH_2$—$CH_2$—$CH_2$—$CH_2$—$CH_2$—$CH_2$—, —CH($CH_3$)—, —CH($CH_3$)—$CH_2$—, —$CH_2$—CH($CH_3$)—, —CH($CH_3$)—$CH_2$—$CH_2$—, —$CH_2$—CH($CH_3$)—$CH_2$—, —$CH_2$—$CH_2$—CH($CH_3$)—, —CH($CH_3$)—$CH_2$—$CH_2$—$CH_2$—, —$CH_2$—CH($CH_3$)—$CH_2$—$CH_2$—, —$CH_2$—$CH_2$—CH($CH_3$)—$CH_2$—, —$CH_2$—$CH_2$—$CH_2$—CH($CH_3$)—, —CH($CH_3$)—$CH_2$—$CH_2$—$CH_2$—$CH_2$—, —$CH_2$—CH($CH_3$)—$CH_2$—$CH_2$—$CH_2$—, —$CH_2$—$CH_2$—CH($CH_3$)—$CH_2$—$CH_2$—, —$CH_2$—$CH_2$—$CH_2$—CH($CH_3$)—$CH_2$—, —$CH_2$—$CH_2$—$CH_2$—$CH_2$—CH($CH_3$)—, —CH($CH_3$)— CH($CH_3$)—, —CH($CH_3$)— $CH_2$—CH($CH_3$)—$CH_2$—, —$CH_2$—$CH_2$—CH($CH_3$)—$CH_2$—$CH_2$—, —$CH_2$—$CH_2$—$CH_2$—CH($CH_3$)—$CH_2$—$CH_2$—, —$CH_2$—$CH_2$—$CH_2$—$CH_2$—CH($CH_3$)—$CH_2$—, —$CH_2$—$CH_2$—$CH_2$—$CH_2$—$CH_2$—CH($CH_3$)—$CH_2$—, —$CH_2$—$CH_2$—$CH_2$—$CH_2$—$CH_2$—$CH_2$—CH($CH_3$)—, —$CH_2$—C($CH_3$)_2$—$CH_2$—, —CH($CH_3$)—CH($CH_3$)—, —C($CH_3$)_2$—C($CH_3$)_2$—, —CH($CH_2OH$)—$CH_2$—, —CH($CH_2OH$)—$CH_2$—$CH_2$—, —CH($CONH_2$)—$CH_2$—, —CH($COOH$)—$CH_2$—, —CH($COOH$)—$CH_2$—$CH_2$—, —CH($COOH$)—$CH_2$—$CH_2$—$CH_2$—, —CH($CONH_2$)—C($CH_3$)_2$—, —CH($CONH_2$)—$CH_2$—$CH_2$—$CH_2$—$CH_2$—, —$CH_2$—CH(OH)—$CH_2$—, —$CH_2$— CH(OH)—CH(OH)—$CH_2$— and —CH(COOH)—C($CH_3$)_2$—, —$CH_2$—$CH_2$—O—$CH_2$—$CH_2$—O—$CH_2$—$CH_2$—, —$CH_2$—$CH_2$—O—$CH_2$—$CH_2$—O—$CH_2$—$CH_2$—, —CH(COOH)—$CH_2$—$CH_2$—C(=O)NH—CH—C(=O)(—NH—$CH_2$—COOH)—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —C(O)—NH—$CH_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—CH$_2$—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—C(O)—NH—CH$_2$—CH$_2$—NH—, —CH$_2$—CH$_2$—C(O)—NH—CH$_2$—CH$_2$—NH—C(O)—, —CH$_2$—CH$_2$—C(O)—NH—CH$_2$—CH$_2$—NH—C(O)—CH$_2$—, a cycloalkylene group, or a substituted cycloalkylene group, —CH$_2$—CH$_2$—CH$_2$—C(O)—NH—CH$_2$—CH$_2$—NH—C(O)—CH$_2$—CH$_2$—, —(CH$_2$)$_{1,2,3,4,5}$—NH—C(O)—CH$_2$CH$_2$—, and combinations of two or more of any of the foregoing.

Group T stands for thiol-reactive groups or protected thiol, i.e., thiol coupled with a protecting group. Non-limiting examples of thiol-reactive groups include maleimide, vinyl sulfone, vinylsulfide, pyridyl disulfide, orthopyridyl disulfide, haloacetyl groups (e.g., containing an iodoacetyl or bromoacetyl group), iodoacetamide, thiol (—SH), thiolate (—S—), TNB-thiol, aziridine, oxirane, acryloyl derivatives, and arylating agents. Maleimide groups and haloacetyl groups react specifically with thiol groups to form stable thioether linkages. Pyridyl disulfides react with thiol groups to form disulfide bonds. Other thiol-reactive groups are possible.

In some embodiments, a thiol protecting group forms with —S a thioether. Non-limiting examples include alkyl thioethers, benzyl thioethers, allyl thioethers, triarylmethyl thioethers (e.g., including a trityl (Trt) group, such as —S-Trt). In other embodiments, a protecting group forms with —S a disulfide. Non-limiting examples include S-sulfonates (e.g., —S—SO$_3^-$, —S—SO$_2$-aryl and —S—SO$_2$-alkyl), S-tert-butyl (e.g., —S—S-tBu), S-(2-aminoethyl), S-2-pyridyl (e.g., —S—S-(2-pyridyl)), and linkers that are symmetrical disulfides where each half of the linker serves as protecting group for the other. Additional non-limiting examples of thiol protecting groups include monothio acetals, dithio acetals, aminothio acetals, thioesters, thiocarbonates, thiocarbamates, and sulfenyl derivatives. Some non-limiting examples of linkers with protected thiols include the following: H$_2$N—CH$_2$—CH$_2$—S-Trt; H$_2$N—CH$_2$—CH$_2$—CH$_2$—S-Trt; H$_2$N—CH$_2$—CH$_2$—CH$_2$—CH$_2$—S-Trt; H$_2$N—CH$_2$—CH$_2$—CH$_2$—CH$_2$—CH$_2$—S-Trt; H$_2$N—CH$_2$—CH$_2$—S—S-tBu; H$_2$N—CH$_2$—CH$_2$—CH$_2$—S—S-tBu; H$_2$N—CH$_2$—CH$_2$—CH$_2$—CH$_2$—S—S-tBu; H$_2$N—CH(COOH)—CH$_2$—S-Trt; H$_2$N—CH(COOH)—C(CH$_3$)$_2$—S-Trt; H$_2$N—CH$_2$—CH$_2$—S—S—CH$_2$—CH$_2$—NH$_2$; H$_2$N—CH(COOH)—CH$_2$—C(═O)NH—CH—[C(═O)(—NH—CH$_2$—COOH)]—CH$_2$—S—S—CH$_2$—CH—[C(═O)(—NH—CH$_2$—COOH)]—NH—C(═O)—CH$_2$—CH$_2$—CH(COOH)—NH$_2$; and H$_2$N—CH(COOH)—CH$_2$—S—S—CH$_2$—CH(COOH)—NH$_2$.

When a linker with a protected thiol is employed to produce at thiol-reactive polymer, the protecting group must be removed to activate the polymer before it can be reacted with a thiol of a substituted cysteine. Reagents and conditions for deprotecting a thiol based on the nature of the protecting group is within the knowledge of the skilled artisan. According to a non-limiting example, a thiol protected by a disulfide can be activated by a reducing agent, such as sodium borohydride, dithiothreitol (DTT), dithioerythritol (DTE), or a phosphine, such as TCEP.

In some embodiments, the linker is a symmetrical disulfide having two identical nucleophilic groups for reaction with the electrophilic group of the polymer. Exemplary symmetrical linkers possess a central disulfide (—S—S—) bond where the sulfur atoms are each connected to identical Y groups and then nucleophiles NU. Non-limiting examples of symmetrical linkers are cystamine and cysteamine, but many others are possible. Reaction of an electrophilically active polymer with a symmetrical disulfide linker such as cystamine results in formation of a symmetrical disulfide polymer having identical polymer segments extending from each of the sulfur atoms of a central disulfide linkage. This arrangement can be represented by the formula POLY-W$_{0,1}$-X-Y—S—S—Y-X-W$_{0,1}$-POLY, where —S—S— indicates the central disulfide bond and the other variable s are as defined above. Due to the symmetry of the resulting disulfide polymer, cleavage with a reducing agent such as dithiothreitol results in formation of two moles of the corresponding thiol-reactive polymer derivative.

Based on the structure of the particular reactive groups E and NU, other reagents used and the reaction conditions chosen, one of ordinary skill in the art can readily determine the structure of the resulting X group. Similarly, based on a linker's thiol-reactive group, reagents used, and reaction conditions chosen, one of ordinary skill can readily determine the structure of the resulting Z group.

In some non-limiting embodiments, X can be an amide, e.g., —C(═O)—NH—, a urethane, e.g., —O—C(O)—NH—, —(CH$_3$)—N—, —(CH$_3$—CH$_2$)—N—, —(CH$_3$—CH$_2$—CH$_2$)—N—, —((CH$_3$)$_2$—CH)—N—, —HN—, —HN—O—, —HN—NH—, —HN—NH—(C═O)—, —HN—NH—(C═O)—NH—, —HN—NH—(C═O)—O— and —HN—NH—SO$_2$—. In yet other embodiments, X can be represented as —C(═O)G-, where G is heteroatom or group such as —O, —NH, —S, or —NR, where R is lower alkyl.

In some embodiments where the polymer is HAS or HES, the terminal glucose moiety at the reducing end of the polymer is coupled to a linker. In these embodiments, the C$_1$ carbon in the terminal glucose can serve as an electrophile for reaction with the nucleophile of the linker. However, in other embodiments, the reducing end terminal glucose residue may be derivatized so that a different electrophilic group is available for reaction, or in yet other embodiments, the reducing end terminal glucose residue may be derivatized so that a nucleophilic group is present that can then be reacted with a corresponding electrophilic group of a linker.

In some embodiments the reducing end terminal glucose residue is used in its unoxidized state (for example at carbon C$_1$) for coupling with a linker, while in other embodiments, the reducing end terminal glucose is used in its oxidized state (for example at carbon C$_1$) for coupling with a linker. In some embodiments, oxidation of the reducing end terminal glucose residue results in a lactone or carboxylic acid whereby carbon C$_1$ of the glucose residue is part of a carbonyl group. Oxidation can be carried out using reagents and reaction conditions familiar to those of ordinary skill in the art, for example using an alkaline iodine solution as described in WO 2005/014050, which is incorporated by reference.

In some embodiments, a bifunctional linker comprising at least one amine group can be reacted with the oxidized reducing end of a HAS or HES polymer to form an amide. Non-limiting exemplary embodiments of such linkers include 1,8-diamino octane, 1,7-diamino heptane, 1,6-diamino hexane, 1,5-diamino pentane, 1,4-diamino butane, 1,3-diamino propane, and 1,2-diamino ethane. Other embodiments include diaminopolyethyleneglycol according to the formula $H_2N-(CH_2-CH_2-O)_n-CH_2-CH_2-NH_2$, where n can be 1, 2, 3, 4, 5, or a higher integer. Where, as in these examples, the second functional group is also an amine, the polymer-linker combination can be reacted with a monohalogen-substituted acetic acid, for example, bromoacetic acid, chloroacetic acid or iodoacetic acid, and an activating agent, such as 1-ethyl-3-(3-dimethylaminopropyl) carbodiimide (EDC), to generate a thiol reactive haloacetamide derivative that can then be coupled to a thiol of a substituted cysteine to form a thioether linkage. This reaction scheme is explained in additional detail in WO 2005/014050.

In another embodiment described further in WO 2005/014050, the polymer-linker combination formed from HAS or HES and a diamino linker can be reacted with a second bifunctional linker comprising a reactive ester group and a maleimide group. A non-limiting example of a reactive ester is succinimide ester and non-limiting example of a bifunctional linker comprising a reactive ester and maleimide is N-(α-maleimidoacetoxy)succinimide ester. The resulting derivative of HAS or HES can then be reacted with the thiol of a substituted cysteine forming a thioether linkage.

In some embodiments, a thiol reactive polymer, such as those described above, can be reacted with a second compound that is also thiol reactive. Examples of such second thiol-reactive compounds include $CH_2=CH-S(O)_2-CH=CH_2$, as described in WO 2014/147173 which is incorporated by reference, and the genus of compounds represented by formula (III) as described in WO 2014/147175, which is incorporated by reference. After coupling the polymer derivative with the second compound, the thiol reactive group of said second compound can be reacted with the thiol of the substituted cysteine, thereby forming a conjugate of polymer and FVIII mutein.

Following is a non-exhaustive and non-limiting list of linkers containing reactive groups capable of reacting with the thiol group of a substituted cysteine of the muteins of the disclosure: 1,11-Bis-Maleimidotriethyleneglycol; 1,4-Bis-Maleimidobutane; 1,4-Bis-Maleimmidyl-2,3-dihydroxy-butane; 1,8-Bis-Maleimidodiethylene-glycol; 2-{2-[2-(2-[pyrid-2-yl]-disulfanyl-ethoxy)-ethoxy]-ethyl-disulfanyl}-pyridine; 2-[N2-(4-Azido-2,3,5,6-tetrafluorobenzoyl)-N6-(6-biotinamidocaproyl)-L-lysinyl]ethylmethanethiosulfate; 2-{N2-[N6-(4-Azido-2,3,5,6-tetrafluorobenzoyl)-N6-(6-biotinamidocaproyl)-L-lysinyl]}ethylmethanethiosulfate; 2-pyridyldithiol-tetraoxaoctatriacontane-N-hydroxysuccinimide; 2-pyridyldithio-tetraoxatetradecane-N-hydroxysuccinimide; 3-(2-Pyridyldithio)propionylhydrazide; 4-(4-N-Maleimidophenyl)-butyric acid hydrazide.HCl; 4-(N-Maleimidomethyl)-cyclohexane-1-carboxyl-hydrazide HCl ½ dioxane; 4-Succinimidyloxycarbonyl-methyl-α-(2-pyridyldithio)toluene; Bis-Maleimidoethane; Bis-Maleimidohexane; Cystamine; Cysteamine; Dithiobis-maleimidoethane; Divinyl sulfone; m-Maleimidobenzoyl-N-hydroxysuccinimide ester; m-Maleimidobenzoyl-N-hydroxysulfosuccinimide ester; N-(2-amino-ethyl)-3-maleimido-propionamide; N-(β-Maleimidopropionic acid) hydrazide.TFA; N-(β-Maleimidopropyloxy)succinimide ester; N-(p-Maleimidophenyl)isocyanate; N-(α-Maleimidoacetoxy)-succinimide ester; N-(γ-Maleimidobutryloxy)sulfosuccinimide ester; N-(γ-Maleimidobutyryloxy)succinimide ester; N-(ε-Maleimidocaproic acid)hydrazide; N-(ε-Maleimidocaproyloxy)succinimide ester; N-(ε-Maleimidocaproyloxy)sulfosuccinimide ester; N-(κ-Maleimidoundecanoic acid)hydrazide; N-(κ-Maleimidoundecanoyloxy)sulfosuccinimide ester; N,N'-Bis(vinylsulfonylacetyl)ethylenediamine; NHS-PEG$_{12}$-Maleimide; NHS-PEG$_{24}$-Maleimide; NHS-PEG$_2$-Maleimide; NHS-PEG$_4$-Maleimide; NHS-PEG$_6$-Maleimide; NHS-PEG$_8$-Maleimide; N-Succinimidyl 3-(2-pyridyldithio)propionate; N-Succinimidyl iodoacetate; N-Succinimidyl S-acetylthio-acetate; N-Succinimidyl S-acetylthio-propionate; N-Succinimidyl(4-iodoacetyl) aminobenzoate; N-Succinimidyl-(4-vinylsulfonyl)benzoate; N-γ-Maleimidobutryloxy-sulfosuccinimide ester; N-γ-Maleimidobutyryloxy-succinimide ester; N-ε-Maleimidocaproic acid; Succinimdyl 3-(bromoacetamido)propionate; Succinimidyl 4-(N-maleimidomethyl)cyclohexane-1-carboxy-(6-amidocaproate); Succinimidyl 4-(N-maleimidomethyl) cyclohexane-1-carboxylate; Succinimidyl 4-(p-maleimidophenyl)butyrate; Succinimidyl 6-(3'-[2-pyridyldithio]propionamido)hexanoate; Succinimidyl-6-(β-maleimidopropionamido)hexanoate; Sulfo-NHS-(2-6-[Biotinamido]-2-(p-azidobezamido); Sulfosuccinimidyl 4-(N-maleimidomethyl)cyclohexane-1-carboxylate; Sulfosuccinimidyl 4-(p-maleimidophenyl)butyrate; Sulfosuccinimidyl 6-(3'-[2-pyridyldithio]propionamido)hexanoate; Sulfosuccinimidyl 6-(α-methyl-α-[2-pyridyldithio]-toluamido) hexanoate; Sulfosuccinimidyl(4-iodo-acetyl)aminobenzoate; Tris-(2-Maleimidoethyl)amine; $H_2N-CH_2-CH_2-SH$; $H_2N-CH_2-CH_2-CH_2-SH$; $H_2N-CH_2-CH_2-CH_2-CH_2-SH$; $H_2N-CH_2-CH_2-CH_2-CH_2-CH_2-SH$; $H_2N-CH(COOH)-CH_2-SH$; $H_2N-CH(COOH)-C(CH_3)_2-SH$; $H_2N-CH(CH_2OH)-CH_2-SH$; $H_2N-CH(CH_2OH)-CH_2-CH_2-SH$; $H_2N-CH(CONH_2)-C(CH_3)_2-SH$; $H_2N-CH(CONH_2)-CH_2-SH$; $H_2N-CH(COOH)-CH_2-CH_2-SH$; $H_2N-CH_2-CH_2-O-CH_2-CH_2-SH$; $H_2N-CH_2-CH_2-O-CH_2-CH_2-O-CH_2-CH_2-SH$; $H_2N-CH_2-CH_2-O-CH_2-CH_2-O-CH_2-CH_2-O-CH_2-CH_2-SH$; $H_2N-CH(COOH)-CH_2-CH_2-C(=O)NH-CH-C(=O)(-NH-CH_2-COOH)-CH_2-SH$; $H_2N-O-CH_2-CH_2-SH$; $H_2N-O-CH_2-CH_2-CH_2-SH$; $H_2N-O-CH_2-CH_2-CH_2-CH_2-SH$; $H_2N-O-CH_2-CH_2-CH_2-CH_2-CH_2-SH$; $H_2N-O-CH(COOH)-CH_2-SH$; $H_2N-O-CH(COOH)-C(CH_3)_2-SH$; $H_2N-O-CH(CH_2OH)-CH_2-SH$; $H_2N-O-CH(CH_2OH)-CH_2-CH_2-SH$; $H_2N-O-CH(CONH_2)-C(CH_3)_2-SH$; $H_2N-NH-CH_2-CH_2-SH$; $H_2N-NH-CH_2-CH_2-CH_2-SH$; $H_2N-NH-CH_2-CH_2-CH_2-CH_2-SH$; $H_2N-NH-CH_2-CH_2-CH_2-CH_2-CH_2-SH$; $H_2N-NH-CH(COOH)-CH_2-SH$; $H_2N-NH-CH(COOH)-C(CH_3)_2-SH$; $H_2N-NH-CH(CH_2OH)-CH_2-SH$; $H_2N-NH-CH(CH_2OH)-CH_2-CH_2-SH$; $H_2N-NH-CH(CONH_2)-C(CH_3)_2-SH$; $H_2N-NH-C(=O)-CH_2-SH$; $H_2N-NH-C(=O)-CH_2-CH_2-SH$; $H_2N-NH-C(=O)-CH_2-CH_2-CH_2-SH$; $H_2N-NH-C(=O)-CH_2-CH_2-CH_2-CH_2-SH$; $H_2N-NH-C(=O)-CH_2-CH_2-CH_2-CH_2-CH_2-SH$; $H_2N-NH-C(=O)-CH(COOH)-CH_2-SH$; $H_2N-NH-C(=O)-CH(COOH)-C(CH_3)_2-SH$;

H₂N—NH—C(=O)—CH(CH₂OH)—CH₂—SH; H₂N—NH—C(=O)—CH(CH₂OH)—CH₂—CH₂—SH; and H₂N—NH—C(=O)—CH(CON H₂)—C(CH₃)₂—SH.

Additional information about certain of linkers listed above may be found in the Thermo Scientific Crosslinking Technical Handbook (2012), which is incorporated by reference.

The linkers listed above (and others not expressly disclosed) may be used to attach a biocompatible polymer to a cysteine substitution mutein of the disclosure. As will be appreciated by one of ordinary skill in the art, certain of these linkers are homobifunctional, comprising reactive groups that react exclusively or predominantly with thiol. Where a biocompatible polymer includes a thiol, these linkers may be used directly without modifying the polymer to link the polymer and mutein using methods and reagents familiar to those of ordinary skill in the art. However, where a polymer naturally lacks a thiol, or lacks a thiol at a desired location in the polymer, one may be created chemically, again using methods and reagents familiar to those of ordinary skill in the art. Certain of the foregoing linkers are heterobifunctional, comprising a reactive group specific for thiol, and at least one other reactive group that is non-reactive with thiol, or that substantially favors reaction with a different functional group than thiol, for example an amine group, or a carboxyl group. Where a biocompatible polymer includes one of these other groups (e.g., —NH₂ or —COOH), these linkers may be used directly without modifying the polymer to link the polymer and mutein using methods and reagents familiar to those of ordinary skill in the art. However, where a polymer naturally lacks one of these groups, or lacks one of these groups at a desired location in the polymer, such groups may be created chemically using methods and reagents familiar to those of ordinary skill in the art.

Additional linkers and methods, conditions and reagents for carrying out reactions to join linkers with bioactive polymers, such as PEG, HAS and HES, and cysteine thiol groups are disclosed in U.S. Pat. Nos. 7,910,661 and 7,863,421, which are incorporated by reference, and international patent application publication nos. WO 2002/080979, WO 2003/070772, WO 2004/024761, WO 2005/014050, WO 2014/147173 and WO 2014/147175, which are incorporated by reference. Further information and details regarding conjugating linkers to thiol groups may be found in G. T., Hermanson, Bioconjugate Techniques, 3$^{rd}$ Ed., Academic Press (ISBN 978-0-12-382239-0), and Chalker, J. M., et al., Chemical Modification of Proteins at Cysteine: Opportunities in Chemistry and Biology, Chem. Asian J., 4:630-640 (2009), each of which is incorporated by reference.

Compositions

The present disclosure also provides compositions comprising FVIII muteins conjugated with a biocompatible polymer for administration to subjects suffering from a deficiency of FVIII activity. Such compositions may further comprise a pharmaceutically acceptable carrier, vehicle, excipients, or stabilizers. These may include, without limitation, solvents, dispersion media, coatings, antibacterial and antifungal agents, bulking agents, wetting agents, emulsifiers, antioxidants, chelating agents, metal ions, proteins, preservatives, pH buffers, zwitterions (e.g., an amino acid such as betaine, taurine, arginine, glycine, lysine and histidine), absorption delaying agents, and the like that are physiologically compatible. Some examples of pharmaceutically acceptable carriers include without limitation water, saline, phosphate buffered saline, dextrose, glycerol, ethanol and the like, as well as combinations thereof.

According to other embodiments, compositions may further include agents for maintaining isotonic balance between the composition and bodily fluids, including without limitation sugars, polyalcohols such as mannitol, sorbitol, or sodium chloride.

A composition for use according to the invention may be in any suitable form for administration to a subject, including without limitation as liquid solutions (e.g., injectable and infusible solutions). The form depends on the intended mode of administration and therapeutic application. In certain embodiments, the mode of administration is parenteral (e.g., intravenous, subcutaneous, intraperitoneal, intramuscular).

Therapeutic compositions are typically sterile and stable under the conditions of manufacture and storage. Compositions can be formulated as a solution, microemulsion, dispersion, liposome, or other ordered structure suitable to high drug concentration. Sterile injectable solutions can be prepared by incorporating conjugates of FVIII muteins and biocompatible polymers in the required amount in an appropriate solvent with one or a combination of ingredients enumerated above, followed by filtered sterilization.

Dispersions are prepared by incorporating the active compound into a sterile vehicle containing a basic dispersion medium and other desired ingredients, for example, from among those enumerated above.

In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In some non-limiting embodiments of the FVIII conjugates of the disclosure, a pharmaceutical composition comprising such conjugates can additionally comprise sucrose, calcium chloride dihydrate, L-histidine, polysorbate 80 and sodium chloride. In some embodiments, these compositions can be supplied in a premixed aqueous solution, or as a lyophilized cake ready for reconstitution with sterile water or with a saline solution, for example, one containing 0.9% (w/v) of sodium chloride.

Methods of Treatment or Prevention

FVIII muteins, conjugates of such muteins with biocompatible polymers, and compositions comprising such muteins or conjugates are useful for treating or preventing bleeding in subjects. Thus, in some embodiments, a FVIII mutein of the disclosure or conjugate of a mutein and a biocompatible polymer are administered in a therapeutically effective amount to a subject in need of treatment for bleeding. In other embodiments, a FVIII mutein of the disclosure or conjugate of a mutein and a biocompatible polymer are administered in a prophylactically effective amount to a subject in need of prophylaxis for bleeding. What constitutes a therapeutically or prophylactically effective amount can be determined according to the knowledge of those ordinarily skilled in the art.

In some embodiments treatment is intended to reduce the amount of bleeding and/or time that bleeding continues before stopping where bleeding has already commenced, for example due to trauma or spontaneous bleeding, for example into joints, muscles or the brain, or other tissues. In some embodiments, prevention is intended to reduce or stop bleeding before it begins. In some embodiments, administration of a mutein or conjugate of the disclosure is provided before a procedure, such as a dental procedure, or surgery (elective or non-elective) where there is a substantial risk that bleeding will occur. In other embodiments, prophylactic administration is provided to reduce or stop bleeding that would occur unexpectedly due, for example, to an accident or spontaneous bleeding.

In some embodiments, subjects in need of treatment or prophylaxis have a deficiency of FVIII activity. In some embodiments, subjects in need of treatment or prophylaxis have hemophilia, for example Hemophilia A (HA). In some subjects, the hemophilia is caused by a genetic mutation (hereditary or spontaneous), while in other subjects it is acquired, for example, due to production of autoantibodies against FVIII. In some embodiments, subjects in need of treatment or prophylaxis have mild, moderate or severe Hemophilia A. In some embodiments, subjects in need of treatment or prophylaxis are pediatric or adult human patients with Hemophilia A.

In some embodiments, treatment or prophylaxis of a subject with a mutein or conjugate of the disclosure is provided in combination with a different drug intended to treat or prevent bleeding. Non-limiting examples of such drugs include desmopressin (such as DDAVP or desmopressin acetate) and aminocaproic acid. Administration of a composition comprising a mutein or conjugate of the disclosure to a subject can occur before, contemporaneously with, or after administration of the other drug or drugs intended to help treat or prevent bleeding. In some embodiments, the mutein or conjugate of the disclosure can be combined with such other drug in the same composition for more convenient dosing, or in different compositions.

Determination of Plasma Half-Life

Plasma half-life and other pharmacokinetic properties of any mutein or conjugate of the disclosure can be determined after administration to a subject using methods familiar to those of ordinary skill in the art. For example, a composition comprising a predetermined amount of a mutein or conjugate thereof with a biocompatible polymer of the disclosure can be administered to a subject with Hemophilia A. Often, the administration is made after a washout period of some time, e.g., 72 hours, to permit any previous dose of Factor VIII replacement therapy to be eliminated. Then, at predetermined times, a blood sample is taken, plasma isolated, and the plasma samples tested for FVIII activity. Non-limiting exemplary times for taking blood samples after administration are 0.25 hours, 0.5 hr, 1 hr, 3 hr, 6 hr, 9 hr, 24 hr, 28 hr, 32 hr and 48 hr, although other time points are possible as long as they, according to the judgment of those ordinarily skilled in the art, permit sampling of plasma FVIII activity over a sufficient span of time and at close enough intervals. Non-limiting examples of assays for testing FVIII activity include the aPTT assay and chromogenic assay, but use of other assays is also possible as explained elsewhere herein, or as would be familiar to those of ordinary skill in the art.

After FVIII activity as a function of time is determined, plasma half-life ($t_{1/2}$) of the FVIII mutein or conjugate thereof administered at the beginning of the experiment can readily be determined using statistical methods such as regression analysis or other statistical methods familiar to those of ordinary skill in the art. In addition, other pharmacokinetic values, such as area under the curve (AUC), can be estimated using other mathematical techniques applied to the data. Publications explaining in greater detail how $t_{1/2}$ and other PK values can be calculated include Bjorkman, et al., J. Thomb. Haemo., 8:730-6 (2010); Bjorkman, et al., Blood, 119(2):612-8 (2012); Morfini, et al., Thromb. Haemost., 66(3):384-6 (1991); Lee, et al., Scientific and Standardization Committee Communication, posted on ISTH website Mar. 21, 2001, downloaded from www.isth.org/resource/group/d4a6f49a-f4ec-450f-9e0f-7be9f0c2ab2e/official_communications/fviiipharmaco.pdf on Feb. 23, 2015; and Vlot, et al., Thromb. Haemost., 83:65-9 (2000), each of which is incorporated by reference.

In some embodiments, plasma half-life in non-human animals, such as monkeys, mice or rats, can be determined using similar techniques as those described above, and the results scaled to predict corresponding plasma half-life in human subjects. The scaling factors to be employed are familiar to those of ordinary skill in the art.

Dosing and Frequency of Administration

Identifying suitable dosages to treat or prevent uncontrolled bleeding in subjects with Hemophilia A (or other deficiency of FVIII activity) with FVIII muteins and conjugates thereof with biocompatible polymers will depend on a variety of factors. Some of these factors are drug-dependent, including without limitation mutein or conjugate half-life, specific activity and side effects, if any. Other factors are subject-dependent, including subject age, body mass, site and severity of bleeding, if any, severity of hemophilia, and general health. Other factors may be relevant as well.

By convention in the art, one International Unit (IU) of FVIII activity is equivalent to the FVIII activity in one milliliter of normal human plasma. Thus, once the activity of a purified preparation of a FVIII mutein or conjugate thereof is determined using an art-recognized method, one of ordinary skill in the art can readily calculate the amount of the FVIII mutein required to formulate a pharmaceutical composition containing some predefined level of FVIII activity expressed in IUs, or concentration expressed in IUs per volume (if liquid) or mass (if solid, e.g., powder). Once so formulated, healthcare providers or patients can then administer an amount of the composition calculated to deliver a desired amount of FVIII activity for treatment or prophylaxis.

Exemplary non-limiting dosages include 0.001 IU/kg, 0.01 IU/kg, 0.1 IU/kg, 0.5 IU/kg, 1 IU/kg, 2 IU/kg, 3 IU/kg, 4 IU/kg, 5 IU/kg, 6 IU/kg, 7 IU/kg, 8 IU/kg, 9 IU/kg, 10 IU/kg, 15 IU/kg, 20 IU/kg, 25 IU/kg, 30 IU/kg, 35 IU/kg, 40 IU/kg, 45 IU/kg, 50 IU/kg, 100 IU/kg, 150 IU/kg, 200 IU/kg, 250 IU/kg, 300 IU/kg, 350 IU/kg, 400 IU/kg, 450 IU/kg, 500 IU/kg, or 1000 IU/kg, where IU/kg is International Units/kilogram of subject body mass. Other dosages are also possible, as are ranges between and among the foregoing values.

FVIII muteins of the disclosure and conjugates thereof with biocompatible polymers having extended half-lives may be administered to subjects at intervals sufficient to maintain any desired level of therapeutic or prophylactic effect. The necessary frequency of administration will depend on a variety of drug and subject specific factors, including those influencing the choice of dosage. Methods for determining the necessary frequency of administration to achieve a desired level of therapeutic or prophylactic efficacy are within the knowledge of those of ordinary skill in the art.

In certain embodiments, conjugates of FVIII muteins and biocompatible polymers are administered to a subject suffering from a deficiency of FVIII activity 5 times per day, 4 times per day, 3 times per day, 2 times per day, once per day, once per 2 days, once per 3 days, once per 4 days, once per 5 days, once per 6 days, once per 7 days, once per 8 days, once per 9 days, once per 10 days, once per 11 days, once per 12 days, once per 13 days, once per 14 days, once per 15 days, once per 16 days, once per 17 days, once per 18 days, once per 19 days, once per 20 days, once per 21 days, once per 22 days, once per 23 days, once per 24 days, once per 25 days, once per 26 days, once per 27 days, once per 28 days, once weekly, once per 2 weeks, once per 3 weeks, once per 4 weeks, once per 5 weeks, once per 6 weeks, once per 7 weeks, once per 8 weeks, or even longer.

The optimal dose and frequency of administration of a pharmaceutical composition comprising a FVIII mutein or conjugate thereof of the disclosure for treating or preventing uncontrolled bleeding in a subject can be determined according to the knowledge of those ordinarily skill in the art. For example, a starting dose can be administered based on upon information such as the severity of the subject's hemophilia, and the subject's age and body mass, or other factors. Blood samples can then be taken at various times thereafter to test FVIII activity in the plasma. If the care provider determines that too low or too high FVIII activity is present, the dose and/or frequency of administration can be changed and the subject's plasma then retested until the amount of FVIII activity is deemed optimal to control the subject's condition.

All publications, patents, patent applications and other documents cited in this application are hereby incorporated by reference in their entireties for all purposes to the same extent as if each individual publication, patent, patent application or other document was individually indicated to be incorporated by reference for all purposes.

EXAMPLES

Example 1: Construction of FVIII Mutein Expression Vectors and Transient Transfection Using standard molecular biology techniques, cysteine substitution mutations were introduced into cDNAs encoding human B domain deleted Factor VIII (BDD FVIII) having the amino acid sequence of SEQ ID NO:2 (FIG. 2). The substitution positions are identified in Table 1 in which the numbers correspond to the positions in the amino acid sequence of mature human FVIII shown in FIG. 1 (SEQ ID NO:1). The same positions are also highlighted in the amino acid sequences shown in FIG. 1 and FIG. 2 using bold and underline font. For transient expression, single cysteine substitutions were introduced into a cDNA encoding BDD FVIII with a spacer and FLAG tag epitope at the carboxy-terminus (SEQ ID NO:7). Later a subset of single cysteine substitutions and combinations with substitutions at positions 336 and/or 1680 were stably transfected using a cDNA without the spacer and FLAG tag (SEQ ID NO:8).

After verifying the sequence of the substitutions, cDNAs encoding the various cysteine substitution muteins were cloned into a mammalian expression vector using an Infusion Dry-Down Kit (Clontech Laboratories, Mountain View, Calif.). Expression vector plasmids were transfected into COS-1 cells as follows. TransiT (Mirus Bio) was diluted (40 µl) in 2 ml Opti-Mem (Life Technologies), vortexed and incubated at room temperature for 15 minutes. Plasmid DNA (16 µg) was added to the mixture and incubated at room temperature for 15 minutes. The 2 ml TransiT/DNA/Opti-MEM mixture was added to a COS-1 cells in a P100 tissue culture plate containing 8 ml of growth medium in the presence of 10% fetal calf serum and incubated overnight at 37° C. in 5% $CO_2$. Transfection medium was removed and the cells were carefully rinsed with 10 ml of cell growth medium. To each plate 10 ml of medium containing penicillin/streptomycin and glutamine was added and incubated at 34° C. or 37° C. in 5% $CO_2$. Seventy-two hours later conditioned medium was harvested, centrifuged to remove cellular debris and reserved for further characterization of transiently expressed FVIII muteins.

Example 2: Quantitation of Transiently Expressed FVIII Muteins

Expression of FVIII muteins from the transiently transfected cell culture supernatants was analyzed by Western blot. First, proteins in samples of supernatants were separated by SDS-PAGE and then blotted to membranes. FVIII was detected using a specific anti-FVIII antibody. Supernatants from COS-1 cells transiently transfected with an expression vector encoding unmutated B domain deleted (BDD) FVIII were included as controls. Apparent expression levels of FVIII muteins compared to unmutated BDD FVIII were estimated by eye and scored as follows: (−) much lower or undetectable compared to control; (+) lower compared to control; (++) same as control; (+++) greater compared to control. The results of expression analysis are set forth in Table 2, column 2. Because substitution with certain cysteines could have altered the epitope of the antibody used to detect expressed protein, it is possible that the actual protein expression level is greater than or less than the apparent expression level.

Example 3: Activity of Transiently Expressed FVIII Muteins

Activity of control unmutated BDD FVIII and the FVIII muteins identified in Table 1 was tested using an activated partial thromboplastin time (aPTT) assay. Cell culture supernatants containing the transiently expressed FVIII muteins were diluted and 50 µl added to 50 µl of aPTT reagent (ACTIN® FSL, Siemens) and 50 µl of FVIII deficient plasma (George King Bio-Medical, Inc., Overland Park Kans.) and incubated for 3 minutes at 37° C. The reaction was initiated immediately with the addition of 50 µl of 25 mM calcium chloride. The time to clot was measured using a StarT4 coagulation instrument (Diagnostica Stago, Parsippany, N.J.). Standard curves were prepared by dilution of pooled normal plasma (FACT, George King Bio-Medical, Inc.). One international unit (IU) of FVIII activity was defined as that amount measured in 1 ml of normal human pooled plasma. Activity of the FVIII muteins was compared to that of unmutated BDD FVIII and expressed as a percentage of the activity of the positive control. The activity of the muteins is set forth in Table 2, column 3. Presence of a FLAG tag at the carboxy-terminus of the unmutated BDD FVIII light chain did not affect its activity.

TABLE 2

| Cysteine substitution mutation | Transient expression level | Percent FVIII activity |
| --- | --- | --- |
| F59C | − | 13% |
| N239C | − | 4% |
| P333C | + | 22% |
| R336C | ++ | 137% |
| P379C | ++ | 28% |
| T481C | ++ | 70% |
| R484C | ++ | 75% |
| L486C | ++ | 20% |
| S488C | + | 25% |
| R489C | + | 28% |

TABLE 2-continued

| Cysteine substitution mutation | Transient expression level | Percent FVIII activity |
|---|---|---|
| R490C | − | 17% |
| P492C | + | 21% |
| K493C | ++ | 50% |
| V495C | +++ | 100% |
| K496C | ++ | 65% |
| H497C | ++ | 76% |
| K499C | + | 18% |
| D500C | − | 18% |
| F501C | ++ | 94% |
| E507C | ++ | 66% |
| Y555C | ++ | 60% |
| R562C | ++ | 39% |
| S568C | + | 49% |
| R571C | + | 46% |
| N582C | − | 7% |
| Y1680C | + | 27% |
| Q1778C | ++ | 105% |
| E1793C | ++ | 48% |
| E1794C | ++ | 75% |
| R1797C | ++ | 42% |
| Q1798C | ++ | 66% |
| G1799C | ++ | 77% |
| A1800C | + | 53% |
| E1801C | ++ | 31% |
| F1806C | +++ | 61% |
| N1810C | + | 21% |
| E1811C | ++ | 67% |
| T1814C | + | 27% |
| F1816C | ++ | 26% |
| K1818C | − | 8% |
| F1891C | + | 48% |
| F2035C | ++ | 55% |
| F2068C | ++ | 74% |
| K2092C | + | 33% |
| F2093C | ++ | 137% |
| S2094C | ++ | 95% |
| S2095C | ++ | 71% |
| N2118C | + | 38% |
| V2125C | − | 21% |
| K2183C | ++ | 63% |
| S2186C | ++ | 64% |
| T2191C | ++ | 20% |
| F2196C | ++ | 59% |
| S2204C | − | 52% |
| S2206C | ++ | 57% |
| L2212C | ++ | 15% |

Example 4: Production of Stably Transfected CHO Pools Expressing Active FVIII Muteins To produce cells stably expressing FVIII muteins, expression vectors for certain of the muteins described in Example 1 were transfected into CHO host cells by electroporation or using polycationic lipid transfection techniques. Two days later, media conditions were changed to select transfected cells and eliminate untransfected cells by growth in media lacking nucleotides. Growth of selected cells was appreciable by about 10-14 days after selection began. CHO pools stably expressing FVIII muteins were then used to produce conditioned media. Media containing expressed FVIII muteins was harvested 7 or 8 days post seeding so that cell viability did not fall below 50%. Cells were removed from media by centrifugation or filtration. Conditioned media from stably transfected CHO cells was then tested for FVIII activity as in Example 3. Results are shown in Table 3.

TABLE 3

| Cysteine substitution mutation | FVIII activity (mIU/ml) in CHO pool media |
|---|---|
| 481 | 322 |
| 484 | 864 |
| 493 | 1561 |
| 495 | 748 |
| 496 | 780 |
| 497 | 457 |
| 507 | 370 |
| 555 | 1081 |
| 562 | 1534 |
| 568 | 254 |
| 1778 | 15899 |
| 1794 | 241 |
| 1798 | 490 |
| 1799 | 1703 |
| 1800 | 1185 |
| 1806 | 1206 |
| 1811 | 1285 |
| 2035 | 698 |
| 2068 | 502 |
| 2093 | 20190 |
| 2094 | 8024 |
| 2095 | 2576 |
| 2183 | 5924 |
| 2186 | 8947 |
| 2196 | 700 |
| 2204 | 1853 |
| 2206 | 1974 |

Example 5: Purification of FVIII Muteins

Conditioned media from stably transfected CHO cells expressing FVIII muteins was harvested and polysorbate 80 added to a final concentration of 0.05%. Media was then passed through an anion exchange column, washed at pH 7.0 in the presence of $CaCl_2$, and bound protein step eluted with 1 M NaCl. Fractions containing FVIII were pooled and passed through an immunoaffinity column using an antibody to FVIII (Eriksson et al., Semin Hematol. 38(2 Suppl 4):24-31 (2001), which is incorporated by reference). After elution of bound protein, FVIII muteins were further purified on MonoQ resin (GE) column with a linear NaCl gradient at pH 6.25 in the presence of $CaCl_2$ and 0.1% polysorbate 80. Purified proteins were then dialyzed into buffer at pH 7.0 and protein concentration determined.

Example 6: Thrombin Cleavage of Selected FVIII Muteins

Purified B domain deleted FVIII (BDD FVIII) and selected FVIII muteins (1.25 µg each) were incubated with or without 1 U/mL of a thrombin (Haematologic Technologies, Essex Junction, Vt.) in 150 mM NaCl, 2 mM $CaCl_2$, 20 mM Tris-HCL, and 5% glycerol, at pH 7.5. Reactions were incubated at 37° C. for 30 minutes after which the reactions were stopped by adding D-phenylalanyl-L-prolyl-L-arginine chloromethyl ketone (PPACK) to a final concentration of 351 nM. Enyzmatic reaction products were then analyzed by denaturing SDS-polyacrylamide gel electrophoresis on a 4-20% bis-tris gel (Invitrogen) and visualized by silver staining. The results are shown in FIG. 4. Thrombin digestion of the muteins and control produced the expected cleavage fragments.

Example 7: PEGylation of Selected FVIII Muteins and Effect on Activity

Selected purified FVIII muteins were treated with a reducing agent to remove the cap from the substituted cysteine and then reacted with a thiol-reactive PEG derivative to create the conjugates. In the reduction step, 100 µg/ml of the FVIII mutein was treated with 50 molar equivalents of tris (2-carboxyethyl)phosphine (TCEP) for 1 hour at 4° C. after which TCEP and released cap were removed using a desalting column (Zeba Spin 7K MWCO from Thermo Scientific). Uncapped muteins were then incubated at 4° C. for at least 30 minutes to allow any native disulfide bonds reduced in the previous step to reoxidize. Uncapped muteins were then treated with 10 molar equivalents of maleimide-PEG 60K (SUNBRIGHT® GL2-600MA, NOF Corp.) at 4° C. overnight in buffer containing 19 mM histidine, 310 mM NaCl, 3.4 mM $CaCl_2$, and 0.02% polysorbate 80.

The extent of PEGylation was determined using a LabChip GXII (Perkin Elmer). In a typical experiment, 500 ng of PEGylated FVIII reaction mixture was denatured, reduced and run on the LabChip. Protein was then detected with a fluorescent dye and data output as an electropherogram allowing quantification of the extent of PEGylation. The extent of PEGylation was expressed as a percentage of the starting amount of protein for each FVIII mutein and is shown in Table 4, column 2.

FVIII activity of the PEGylated muteins was measured using the aPTT assay as described in Example 3. Activity after PEGylation was calculated as the percent activity relative to the activity of each mutein before PEGylation and is shown in Table 4, column 3. The specific activity for three PEGylated muteins comprising the S2094C mutation was also determined. Activity was measured by two methods, including the aPTT assay described in Example 3 and a chromogenic FVIII activity assay according to the manufacturer's instructions (DiaPharma). Results are shown in Table 5.

TABLE 4

| Cysteine substitution mutation | Percent PEGylation | Percent FVIII activity after PEGylation |
| --- | --- | --- |
| R484C | 0 | 106 |
| K493C | 73 | 119 |
| K496C | 33 | 104 |
| Y555C | 6 | 109 |
| R562C | 8 | 113 |
| Q1778C | 1 | 103 |
| G1799C | 13 | 113 |
| F1806C | 12 | 114 |
| F2035C | 27 | 102 |
| F2093C | 70 | 49 |
| S2094C | 41 | 81 |
| S2095C | 20 | 92 |
| K2183C | 4 | 112 |
| S2186C | 21 | 88 |
| F2196C | 14 | 92 |
| S2204C | 38 | 92 |
| S2206C | 9 | 78 |
| S2094C + R336A | 45 | 85 |
| S2094C + R336A + Y1680F | 47 | 82 |
| S2094C + Y1680F | 38 | 88 |
| BDD FVIII | 2 | 111 |

TABLE 5

| PEGylated (PEG 60K) FVIII mutein | Specific activity aPTT assay (IU/mg) | Specific activity chromogenic assay (IU/mg) |
| --- | --- | --- |
| S2094C | 1240 | 3900 |
| S2094C + R336A | 1380 | 4300 |

TABLE 5-continued

| PEGylated (PEG 60K) FVIII mutein | Specific activity aPTT assay (IU/mg) | Specific activity chromogenic assay (IU/mg) |
| --- | --- | --- |
| S2094C + Y1680F | 1180 | 4000 |
| S2094C + R336A + Y1680F | 1050 | 4175 |

Example 9: In Vivo Clotting Activity of PEGylated FVIII Muteins

PEGylated FVIII muteins were tested for their ability to control severe bleeding in male hemophilic mice genetically null for FVIII (strain B6;129S-F8tm1Kaz/J) at different times after administration. Bi, et al., Nat Genet 10:119-21 (1995), which is incorporated by reference. The muteins tested were S2094C, S2094C+R336A, and S2094C+R336A+Y1680F, in each case conjugated with PEG 60K on the cysteine substituted at position 2094.

Mice were anesthetized with isoflurane and placed on a heated platform. Tails were immersed for 5 minutes in 50 mL phosphate buffered saline (PBS) warmed to 37° C. and then removed from the PBS. Mice were then intravenously administered saline, a single dose of unmutated BDD FVIII or one of three PEGylated FVIII muteins (200 IU/kg based on activity measured by the aPTT assay). Ten animals were used for saline, and three to five animals were used in each treatment group. At 5 minutes, 24 hours and 48 hours after dosing, the animal's tails were transected 3 mm from the end and placed for 10 minutes into a tube containing PBS warmed to 37° C. For animals given saline, tail transection was performed 5 min after administration. The collection tube was then centrifuged and the pelleted erythrocytes resuspended in 5 ml lysis buffer (8.3 g/L ammonium chloride, 1.0 g/L potassium bicarbonate, and 0.037 g/L EDTA). Light absorbance of the samples was measured spectroscopically at 575 nm and total blood loss calculated from a standard curve. The experiment using BDD FVIII was performed separately from the experiment using the PEGylated FVIII muteins. Results from saline control experiments conducted at different times were combined.

Figure 5:
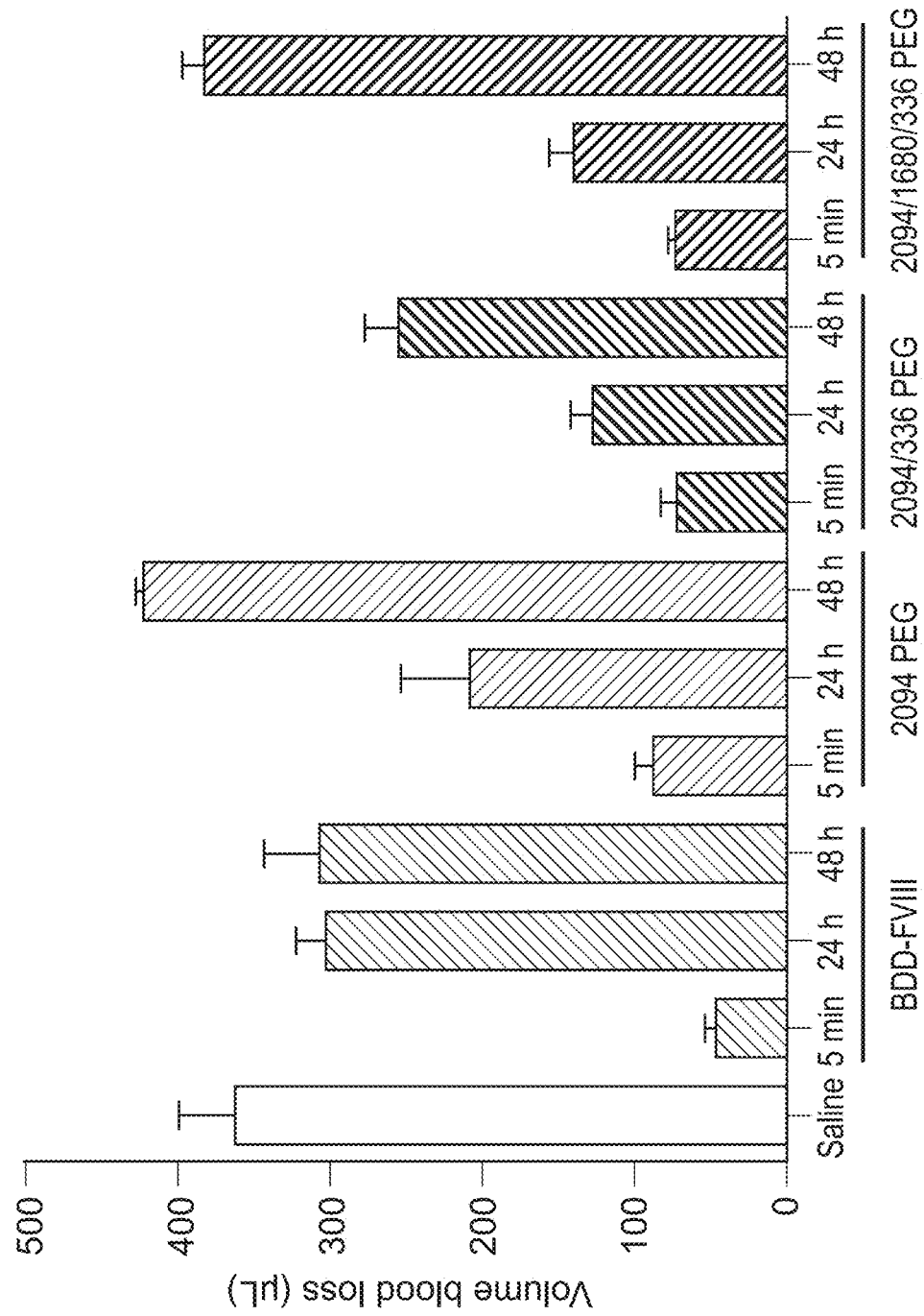
FIG. 5 provides data comparing the in vivo procoagulant effect of unmodified BDD FVIII with that of three PEGylated FVIII muteins comprising a cysteine substitution at position 2094. Mice phenotypic for Hemophilia A were administered BDD FVIII or one of the muteins. At 5 min, 24 hr and 48 hr thereafter, the distal ends of the tails were transected and the total blood loss over 10 minutes determined. Compared to unmodified BDD FVIII, the duration of the procoagulant effect of each of the muteins was longer.

Results from the experiments are shown in FIG. 5. Data is the average ±SEM. After dosing hemophilic mice with BDD FVIII, blood loss was substantially reduced compared to negative control at the 5 min time point, but the procoagulant effect disappeared by 24 hours. In contrast, for each of the three PEGylated muteins tested, procoagulant effect in the hemophilic mice was evident 24 hours after dosing, and in one case (2094+336), the effect was evident 48 hours after dosing. Thus, the duration of action of each of the PEGylated muteins was substantially longer compared to unmodified BDD FVIII. The data demonstrates that compared to unmodified FVIII, it is possible to substantially extend the half-life of FVIII by conjugating a biocompatible polymer to a cysteine substitution mutation of the disclosure.

Example 10: Pharmacokinetics of FVIII Muteins in Hemophilic Mice

Purified FVIII muteins are administered to Hemophilia A mice via the tail vein. Unmutated BDD FVIII is also tested as a control. At different times after administering FVIII, mice are anesthetized and blood drawn into sodium citrate. Plasma is prepared by centrifuging the blood at 2500 g for 10 minutes. Plasma is then used in one or more assays, e.g., the aPTT assay or chromogenic assay, to measure plasma FVIII clotting activity. Plasma FVIII protein levels are determined by a FVIII specific ELISA using a FVIII specific monoclonal antibody. By comparing plasma FVIII activity and protein concentrations as a function of time after FVIII administration, it is possible to calculate the circulatory half-life of the FVIII muteins in comparison to unmutated BDD FVIII.

Additional embodiments of the disclosure include and encompass:

1. A modified FVIII protein comprising at least one cysteine substitution mutation at an amino acid corresponding to a position in the amino acid sequence of SEQ ID NO:1 selected from the group of amino acid positions consisting of: 59, 239, 333, 336, 379, 481, 484, 486, 488, 489, 490, 492, 493, 495, 496, 497, 499, 500, 501, 507, 555, 562, 568, 571, 582, 1680, 1778, 1793, 1794, 1797, 1798, 1799, 1800, 1801, 1806, 1810, 1811, 1814, 1816, 1818, 1891, 2035, 2068, 2092, 2093, 2094, 2095, 2118, 2125, 2183, 2186, 2191, 2196, 2204, 2206, and 2212.

2. The modified FVIII protein of embodiment 1, wherein the cysteine substitution mutation occurs at position 59.

3. The modified FVIII protein of embodiment 1, wherein the cysteine substitution mutation occurs at position 239.

4. The modified FVIII protein of embodiment 1, wherein the cysteine substitution mutation occurs at position 333.

5. The modified FVIII protein of embodiment 1, wherein the cysteine substitution mutation occurs at position 336.

6. The modified FVIII protein of embodiment 1, wherein the cysteine substitution mutation occurs at position 379.

7. The modified FVIII protein of embodiment 1, wherein the cysteine substitution mutation occurs at position 481.

8. The modified FVIII protein of embodiment 1, wherein the cysteine substitution mutation occurs at position 484.

9. The modified FVIII protein of embodiment 1, wherein the cysteine substitution mutation occurs at position 486.

10. The modified FVIII protein of embodiment 1, wherein the cysteine substitution mutation occurs at position 488.

11. The modified FVIII protein of embodiment 1, wherein the cysteine substitution mutation occurs at position 489.

12. The modified FVIII protein of embodiment 1, wherein the cysteine substitution mutation occurs at position 490.

13. The modified FVIII protein of embodiment 1, wherein the cysteine substitution mutation occurs at position 492.

14. The modified FVIII protein of embodiment 1, wherein the cysteine substitution mutation occurs at position 493.

15. The modified FVIII protein of embodiment 1, wherein the cysteine substitution mutation occurs at position 495.

16. The modified FVIII protein of embodiment 1, wherein the cysteine substitution mutation occurs at position 496.

17. The modified FVIII protein of embodiment 1, wherein the cysteine substitution mutation occurs at position 497.

18. The modified FVIII protein of embodiment 1, wherein the cysteine substitution mutation occurs at position 499.

19. The modified FVIII protein of embodiment 1, wherein the cysteine substitution mutation occurs at position 500.

20. The modified FVIII protein of embodiment 1, wherein the cysteine substitution mutation occurs at position 501.

21. The modified FVIII protein of embodiment 1, wherein the cysteine substitution mutation occurs at position 507.

22. The modified FVIII protein of embodiment 1, wherein the cysteine substitution mutation occurs at position 555.

23. The modified FVIII protein of embodiment 1, wherein the cysteine substitution mutation occurs at position 562.

24. The modified FVIII protein of embodiment 1, wherein the cysteine substitution mutation occurs at position 568.

25. The modified FVIII protein of embodiment 1, wherein the cysteine substitution mutation occurs at position 571.

26. The modified FVIII protein of embodiment 1, wherein the cysteine substitution mutation occurs at position 582.

27. The modified FVIII protein of embodiment 1, wherein the cysteine substitution mutation occurs at position 1680.

28. The modified FVIII protein of embodiment 1, wherein the cysteine substitution mutation occurs at position 1778.

29. The modified FVIII protein of embodiment 1, wherein the cysteine substitution mutation occurs at position 1793.

30. The modified FVIII protein of embodiment 1, wherein the cysteine substitution mutation occurs at position 1794.

31. The modified FVIII protein of embodiment 1, wherein the cysteine substitution mutation occurs at position 1797.

32. The modified FVIII protein of embodiment 1, wherein the cysteine substitution mutation occurs at position 1798.

33. The modified FVIII protein of embodiment 1, wherein the cysteine substitution mutation occurs at position 1799.

34. The modified FVIII protein of embodiment 1, wherein the cysteine substitution mutation occurs at position 1800.

35. The modified FVIII protein of embodiment 1, wherein the cysteine substitution mutation occurs at position 1801.

36. The modified FVIII protein of embodiment 1, wherein the cysteine substitution mutation occurs at position 1806.

37. The modified FVIII protein of embodiment 1, wherein the cysteine substitution mutation occurs at position 1810.

38. The modified FVIII protein of embodiment 1, wherein the cysteine substitution mutation occurs at position 1811.

39. The modified FVIII protein of embodiment 1, wherein the cysteine substitution mutation occurs at position 1814.

40. The modified FVIII protein of embodiment 1, wherein the cysteine substitution mutation occurs at position 1816.

41. The modified FVIII protein of embodiment 1, wherein the cysteine substitution mutation occurs at position 1818.

42. The modified FVIII protein of embodiment 1, wherein the cysteine substitution mutation occurs at position 1891.

43. The modified FVIII protein of embodiment 1, wherein the cysteine substitution mutation occurs at position 2035.

44. The modified FVIII protein of embodiment 1, wherein the cysteine substitution mutation occurs at position 2068.

45. The modified FVIII protein of embodiment 1, wherein the cysteine substitution mutation occurs at position 2092.

46. The modified FVIII protein of embodiment 1, wherein the cysteine substitution mutation occurs at position 2093.

47. The modified FVIII protein of embodiment 1, wherein the cysteine substitution mutation occurs at position 2094.

48. The modified FVIII protein of embodiment 1, wherein the cysteine substitution mutation occurs at position 2095.

49. The modified FVIII protein of embodiment 1, wherein the cysteine substitution mutation occurs at position 2118.

50. The modified FVIII protein of embodiment 1, wherein the cysteine substitution mutation occurs at position 2125.

51. The modified FVIII protein of embodiment 1, wherein the cysteine substitution mutation occurs at position 2183.

52. The modified FVIII protein of embodiment 1, wherein the cysteine substitution mutation occurs at position 2186.

53. The modified FVIII protein of embodiment 1, wherein the cysteine substitution mutation occurs at position 2191.

54. The modified FVIII protein of embodiment 1, wherein the cysteine substitution mutation occurs at position 2196.

55. The modified FVIII protein of embodiment 1, wherein the cysteine substitution mutation occurs at position 2204.

56. The modified FVIII protein of embodiment 1, wherein the cysteine substitution mutation occurs at position 2206.

57. The modified FVIII protein of embodiment 1, wherein the cysteine substitution mutation occurs at position 2212.

58. The modified FVIII protein of embodiment 1, wherein said FVIII protein further comprises at least one additional substitution mutation at an amino acid corresponding to position 336, 562, 1680 or 1968 in the amino acid sequence of SEQ ID NO:1 selected from the group of substitutions consisting of: R336A, R562A, Y1680F and K1968A.

59. The modified FVIII protein of embodiment 58, wherein the cysteine substitution mutation occurs at position 493 and is combined with the substitution mutation R336A.

60. The modified FVIII protein of embodiment 58, wherein the cysteine substitution mutation occurs at position 496 and is combined with the substitution mutation R336A.

61. The modified FVIII protein of embodiment 58, wherein the cysteine substitution mutation occurs at position 1799 and is combined with the substitution mutation R336A.

62. The modified FVIII protein of embodiment 58, wherein the cysteine substitution mutation occurs at position 2094 and is combined with the substitution mutation R336A.

63. The modified FVIII protein of embodiment 58, wherein the cysteine substitution mutation occurs at position 2186 and is combined with the substitution mutation R336A.

64. The modified FVIII protein of embodiment 58, wherein the cysteine substitution mutation occurs at position 2204 and is combined with the substitution mutation R336A.

65. The modified FVIII protein of embodiment 58, wherein the cysteine substitution mutation occurs at position 2206 and is combined with the substitution mutation R336A.

66. The modified FVIII protein of embodiment 58, wherein the cysteine substitution mutation occurs at position 493 and is combined with the substitution mutation Y1680F.

67. The modified FVIII protein of embodiment 58, wherein the cysteine substitution mutation occurs at position 496 and is combined with the substitution mutation Y1680F.

68. The modified FVIII protein of embodiment 58, wherein the cysteine substitution mutation occurs at position 1799 and is combined with the substitution mutation Y1680F.

69. The modified FVIII protein of embodiment 58, wherein the cysteine substitution mutation occurs at position 2094 and is combined with the substitution mutation Y1680F.

70. The modified FVIII protein of embodiment 58, wherein the cysteine substitution mutation occurs at position 2186 and is combined with the substitution mutation Y1680F.

71. The modified FVIII protein of embodiment 58, wherein the cysteine substitution mutation occurs at position 2204 and is combined with the substitution mutation Y1680F.

72. The modified FVIII protein of embodiment 58, wherein the cysteine substitution mutation occurs at position 2206 and is combined with the substitution mutation Y1680F.

73. The modified FVIII protein of embodiment 58, wherein the cysteine substitution mutation occurs at position 493 and is combined with the substitution mutations R336A and Y1680F.

74. The modified FVIII protein of embodiment 58, wherein the cysteine substitution mutation occurs at position 496 and is combined with the substitution mutations R336A and Y1680F.

75. The modified FVIII protein of embodiment 58, wherein the cysteine substitution mutation occurs at position 1799 and is combined with the substitution mutations R336A and Y1680F.

76. The modified FVIII protein of embodiment 58, wherein the cysteine substitution mutation occurs at position 2094 and is combined with the substitution mutations R336A and Y1680F.

77. The modified FVIII protein of embodiment 58, wherein the cysteine substitution mutation occurs at position 2186 and is combined with the substitution mutations R336A and Y1680F.

78. The modified FVIII protein of embodiment 58, wherein the cysteine substitution mutation occurs at position 2204 and is combined with the substitution mutations R336A and Y1680F.

79. The modified FVIII protein of embodiment 58, wherein the cysteine substitution mutation occurs at position 2206 and is combined with the substitution mutations R336A and Y1680F.

80. The modified FVIII protein of any one of embodiments 1-79, wherein compared to unmodified FVIII said modified FVIII has a functional attribute selected from the group consisting of: higher expression, greater procoagulant activity, reduced immunogenicity, greater stability, reduced susceptibility to degradation, greater resistance to proteases, greater resistance to oxidation, improved ability to be activated by thrombin or other coagulation factors, improved ability to combine with other coagulation factors and components into the tenase complex, increased association or binding to vWF, improved shelf-life, reduced binding by inhibitory antibodies, reduced interaction with the low density lipoprotein receptor related protein, reduced interaction with low density lipoprotein receptor, reduced interaction with cell surface heparin sulphate proteoglycans, increased circulatory half-life, and improved pharmacokinetics.

81. The modified FVIII protein of any one of embodiments 1-79 further comprising a moiety.

82. The modified FVIII protein of embodiment 81, wherein said moiety is selected from the group consisting of: small organic molecule, macromolecule, antibody, antibody fragment, antigen binding domain, antibody Fc region, protein of immunologic origin, protein of immunologic function, intact clotting factor, functional fragment of a clotting factor, enzyme, nucleic acid, DNA, RNA, organometallic compound, lipid, fatty acyl chain, phospholipid, glycolipid, protein, peptide, amino acid, carbohydrate, monosaccharide, disaccharide, hydrophobic compound, hydrophilic compound, organic acid, and organic base.

83. The modified FVIII protein of embodiment 81, wherein said moiety is attached to said cysteine.

84. The modified FVIII protein of embodiment 83, wherein said moiety is attached to said cysteine covalently.

85. The modified FVIII protein of embodiment 84, wherein said moiety is covalently attached via the thiol of said cysteine.

86. The modified FVIII protein of embodiment 84, wherein said moiety is covalently attached via a reactive group.

87. The modified FVIII protein of embodiment 84, wherein said moiety further comprises a linker.

88. The modified FVIII protein of any one of embodiments 1-79, further comprising a biocompatible polymer attached directly or indirectly to said cysteine.

89. The modified FVIII protein of embodiment 88, further comprising a linker between said cysteine and said biocompatible polymer.

90. The modified FVIII protein of embodiment 88, wherein said biocompatible polymer is selected from the group consisting of: polyethylene glycol (PEG), hydroxyalkyl starch, hydroxyethyl starch (HES), polysialic acid (PSA), a zwitterionic brush polymer, and a poly-phosphorylcholine branched polymer.

91. The modified FVIII protein of embodiment 88, wherein said modified FVIII protein has an increased circulatory half-life compared to unmodified FVIII protein.

92. The modified FVIII protein of embodiment 91, wherein the circulatory half-life of said modified FVIII protein is increased at least about 2 times compared to unmodified FVIII protein.

93. The modified FVIII protein of embodiment 91, wherein the circulatory half-life of said modified FVIII protein is increased at least about 5 times compared to unmodified FVIII protein.
94. The modified FVIII protein of embodiment 91, wherein the circulatory half-life of said modified FVIII protein is increased at least about 10 times compared to unmodified FVIII protein.
95. A composition comprising the modified FVIII protein of embodiment 88 and a pharmaceutically acceptable excipient.
96. A nucleic acid encoding the modified FVIII protein of any one of embodiments 1-79.
97. A host cell comprising the nucleic acid of embodiment 96 operatively linked to a genetic regulatory sequence.
98. A method of treating bleeding in a subject having a deficiency of FVIII activity comprising the step of administering a therapeutically effective dose of a composition comprising the modified FVIII protein of embodiment 88.
99. The method of embodiment 98, wherein said subject has hemophilia A.
100. A method of preventing bleeding in a subject having a deficiency of FVIII activity comprising the step of administering a prophylactically effective dose of a composition comprising the modified FVIII protein of embodiment 88.
101. The method of embodiment 100, wherein said subject has hemophilia A.
102. The method of embodiment 100, wherein said step of administering said modified FVIII protein occurs not more often than a period selected from the group consisting of: 3 days, 4 days, 5 days, 6 days, 7 days, 8 days, 9 days, 10 days, 11 days, 12 days, 13 days, 2 weeks, and 3 weeks.
103. A method of preparing a conjugate comprising a cysteine-substituted FVIII protein and a biocompatible polymer comprising the steps of:

reacting under suitable conditions a thiol-reactive polymer having the formula POLY-$W_{0,1}$-X—Y-T with a cysteine substituted FVIII protein to form a conjugate having the formula POLY-$W_{0,1}$-X-Y-Z-FVIII,
where POLY is a biocompatible polymer, W is a spacer, X is a group formed by the reaction of an electrophile and a nucleophile, Y is a moiety, T is a thiol-reactive group or a protected thiol, Z is a group formed by the reaction of T and a thiol in a substituted cysteine, and FVIII is the remainder of FVIII protein.
104. The method of embodiment 103, where the thiol-reactive polymer, POLY-$W_{0,1}$-X-Y-T, is formed by reacting under suitable conditions an electrophilically active polymer having the formula POLY-$W_{0,1}$-E and a nucleophilically active molecule having the formula NU-Y-T, where POLY is a biocompatible polymer, W is a spacer, E is an electrophilic group, NU is a nucleophilic group, Y is a moiety and T is a thiol-reactive group or a protected thiol.
105. The method of embodiment 103, where the thiol-reactive polymer, POLY-$W_{0,1}$-X-Y-T, is formed by reacting under suitable conditions a nucleophilically active polymer having the formula POLY-$W_{0,1}$-NU and an electrophilically active molecule having the formula E-Y-T, where POLY is a biocompatible polymer, W is a spacer, E is an electrophilic group, NU is a nucleophilic group, Y is a moiety and T is a thiol-reactive group or a protected thiol.
106. The method of embodiment 104 or 105, where said cysteine-substituted FVIII protein is the cysteine substituted FVIII protein of any one of embodiments 1 to 79.
107. The method of embodiment 103, where spacer W or moiety Y includes a physiologically cleavable linkage.
108. A conjugate comprising a cysteine-substituted FVIII protein and a biocompatible polymer prepared by the method of embodiment 103.
109. The conjugate of embodiment 108, where said cysteine-substituted FVIII protein is the cysteine substituted FVIII protein of any one of embodiments 1 to 79.

What is claimed is:

1. A modified Factor VIII (FVIII) protein comprising amino acid substitutions at one or more positions corresponding to 336, 1680, 2094, 2186, 2204, or 2206 with reference to the amino acid sequence of SEQ ID NO:1, and wherein the substitutions are selected from the group consisting of:

a) S2094C, R336A and Y1680F;
b) S2186C, R336A and Y1680F;
c) S2204C, R336A and Y1680F;
d) S2206C, R336A and Y1680F;
e) S2094C and R336A;
f) S2186C and R336A;
g) S2204C and R336A;
h) S2206C and R336A;
i) S2094C and Y1680F;
j) S2186C and Y1680F;
k) S2204C and Y1680F;

l) S2206C and Y1680F;
m) S2094C;
n) S2186C;
o) S2204C; and
p) S2206C.

2. The modified FVIII protein of claim 1, wherein said FVIII protein is a single chain.

3. The modified FVIII protein of claim 1, wherein said FVIII protein is an inactive two-chain form comprising a proteolytic site of thrombin.

4. The modified FVIII protein of claim 1, wherein said FVIII protein lacks all or part of the B domain.

5. The modified FVIII protein of claim 1, wherein said FVIII protein is activated.

6. A conjugate comprising the modified FVIII protein of claim 1 and a biocompatible polymer covalently attached directly, or indirectly via a linker, to said cysteine substitution.

7. The conjugate of claim 6, wherein the conjugate further comprises a spacer.

8. The conjugate of claim 6, wherein said covalent attachment is to the sulfur atom of the thiol group of said cysteine substitution.

9. The conjugate of claim 6, wherein said biocompatible polymer is selected from the group consisting of: polyethylene glycol (PEG), hydroxyalkyl starch (HAS), polysialic acid (PSA), a zwitterionic brush polymer, and a polyphosphorylcholine branched polymer.

10. The conjugate of claim 9, wherein said biocompatible polymer is hydroxyethyl starch (HES) or polyethylene glycol (PEG).

11. The conjugate of claim 10, wherein the circulatory half-life of said modified FVIII protein is increased at least 2 times compared to unmodified FVIII protein.

12. A composition comprising the conjugate of claim 10 and a pharmaceutically acceptable excipient.

* * * * *

SEQUENCE LISTING

<160> NUMBER OF SEQ ID NOS: 8

<210> SEQ ID NO 1
<211> LENGTH: 2332
<212> TYPE: PRT
<213> ORGANISM: Homo sapiens

<400> SEQUENCE: 1

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125
```

```
Phe Pro Gly Gly Ser His Thr Tyr Val Trp Gln Val Leu Lys Glu Asn
            130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Glu Lys Thr Gln Thr Leu
            180                 185                 190
His Lys Phe Ile Leu Leu Phe Ala Val Phe Asp Glu Gly Lys Ser Trp
        195                 200                 205
His Ser Glu Thr Lys Asn Ser Leu Met Gln Asp Arg Asp Ala Ala Ser
    210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
            260                 265                 270
Gly His Thr Phe Leu Val Arg Asn His Arg Gln Ala Ser Leu Glu Ile
        275                 280                 285
Ser Pro Ile Thr Phe Leu Thr Ala Gln Thr Leu Leu Met Asp Leu Gly
    290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Pro Gln Leu Arg
                325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asp Asn Ser Pro Ser Phe
        355                 360                 365
Ile Gln Ile Arg Ser Val Ala Lys Lys His Pro Lys Thr Trp Val His
    370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
        435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
        515                 520                 525
Leu Thr Arg Tyr Tyr Ser Ser Phe Val Asn Met Glu Arg Asp Leu Ala
    530                 535                 540
```

```
Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
        580                 585                 590

Arg Phe Leu Pro Asn Pro Ala Gly Val Gln Leu Glu Asp Pro Glu Phe
    595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
        660                 665                 670

Phe Ser Gly Glu Thr Val Phe Met Ser Met Glu Asn Pro Gly Leu Trp
    675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
            725                 730                 735

Ile Glu Pro Arg Ser Phe Ser Gln Asn Ser Arg His Pro Ser Thr Arg
        740                 745                 750

Gln Lys Gln Phe Asn Ala Thr Thr Ile Pro Glu Asn Asp Ile Glu Lys
    755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
            805                 810                 815

Ser Asp Asp Pro Ser Pro Gly Ala Ile Asp Ser Asn Asn Ser Leu Ser
        820                 825                 830

Glu Met Thr His Phe Arg Pro Gln Leu His His Ser Gly Asp Met Val
    835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
        900                 905                 910

Tyr Asp Ser Gln Leu Asp Thr Thr Leu Phe Gly Lys Lys Ser Ser Pro
    915                 920                 925

Leu Thr Glu Ser Gly Gly Pro Leu Ser Leu Ser Glu Glu Asn Asn Asp
930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
```

-continued

```
                965                 970                 975
Arg Ala His Gly Pro Ala Leu Leu Thr Lys Asp Asn Ala Leu Phe Lys
                    980                 985                 990
Val Ser Ile Ser Leu Leu Lys Thr Asn Lys Thr Ser Asn Asn Ser Ala
        995                 1000                1005
Thr Asn Arg Lys Thr His Ile Asp Gly Pro Ser Leu Leu Ile Glu
    1010                1015                1020
Asn Ser Pro Ser Val Trp Gln Asn Ile Leu Glu Ser Asp Thr Glu
    1025                1030                1035
Phe Lys Lys Val Thr Pro Leu Ile His Asp Arg Met Leu Met Asp
    1040                1045                1050
Lys Asn Ala Thr Ala Leu Arg Leu Asn His Met Ser Asn Lys Thr
    1055                1060                1065
Thr Ser Ser Lys Asn Met Glu Met Val Gln Gln Lys Lys Glu Gly
    1070                1075                1080
Pro Ile Pro Pro Asp Ala Gln Asn Pro Asp Met Ser Phe Phe Lys
    1085                1090                1095
Met Leu Phe Leu Pro Glu Ser Ala Arg Trp Ile Gln Arg Thr His
    1100                1105                1110
Gly Lys Asn Ser Leu Asn Ser Gly Gln Gly Pro Ser Pro Lys Gln
    1115                1120                1125
Leu Val Ser Leu Gly Pro Glu Lys Ser Val Glu Gly Gln Asn Phe
    1130                1135                1140
Leu Ser Glu Lys Asn Lys Val Val Val Gly Lys Gly Glu Phe Thr
    1145                1150                1155
Lys Asp Val Gly Leu Lys Glu Met Val Phe Pro Ser Ser Arg Asn
    1160                1165                1170
Leu Phe Leu Thr Asn Leu Asp Asn Leu His Glu Asn Asn Thr His
    1175                1180                1185
Asn Gln Glu Lys Lys Ile Gln Glu Glu Ile Glu Lys Lys Glu Thr
    1190                1195                1200
Leu Ile Gln Glu Asn Val Val Leu Pro Gln Ile His Thr Val Thr
    1205                1210                1215
Gly Thr Lys Asn Phe Met Lys Asn Leu Phe Leu Leu Ser Thr Arg
    1220                1225                1230
Gln Asn Val Glu Gly Ser Tyr Asp Gly Ala Tyr Ala Pro Val Leu
    1235                1240                1245
Gln Asp Phe Arg Ser Leu Asn Asp Ser Thr Asn Arg Thr Lys Lys
    1250                1255                1260
His Thr Ala His Phe Ser Lys Lys Gly Glu Glu Glu Asn Leu Glu
    1265                1270                1275
Gly Leu Gly Asn Gln Thr Lys Gln Ile Val Glu Lys Tyr Ala Cys
    1280                1285                1290
Thr Thr Arg Ile Ser Pro Asn Thr Ser Gln Gln Asn Phe Val Thr
    1295                1300                1305
Gln Arg Ser Lys Arg Ala Leu Lys Gln Phe Arg Leu Pro Leu Glu
    1310                1315                1320
Glu Thr Glu Leu Glu Lys Arg Ile Ile Val Asp Asp Thr Ser Thr
    1325                1330                1335
Gln Trp Ser Lys Asn Met Lys His Leu Thr Pro Ser Thr Leu Thr
    1340                1345                1350
Gln Ile Asp Tyr Asn Glu Lys Glu Lys Gly Ala Ile Thr Gln Ser
    1355                1360                1365
```

```
Pro Leu Ser Asp Cys Leu Thr Arg Ser His Ser Ile Pro Gln Ala
    1370            1375            1380

Asn Arg Ser Pro Leu Pro Ile Ala Lys Val Ser Ser Phe Pro Ser
    1385            1390            1395

Ile Arg Pro Ile Tyr Leu Thr Arg Val Leu Phe Gln Asp Asn Ser
    1400            1405            1410

Ser His Leu Pro Ala Ala Ser Tyr Arg Lys Lys Asp Ser Gly Val
    1415            1420            1425

Gln Glu Ser Ser His Phe Leu Gln Gly Ala Lys Lys Asn Asn Leu
    1430            1435            1440

Ser Leu Ala Ile Leu Thr Leu Glu Met Thr Gly Asp Gln Arg Glu
    1445            1450            1455

Val Gly Ser Leu Gly Thr Ser Ala Thr Asn Ser Val Thr Tyr Lys
    1460            1465            1470

Lys Val Glu Asn Thr Val Leu Pro Lys Pro Asp Leu Pro Lys Thr
    1475            1480            1485

Ser Gly Lys Val Glu Leu Leu Pro Lys Val His Ile Tyr Gln Lys
    1490            1495            1500

Asp Leu Phe Pro Thr Glu Thr Ser Asn Gly Ser Pro Gly His Leu
    1505            1510            1515

Asp Leu Val Glu Gly Ser Leu Leu Gln Gly Thr Glu Gly Ala Ile
    1520            1525            1530

Lys Trp Asn Glu Ala Asn Arg Pro Gly Lys Val Pro Phe Leu Arg
    1535            1540            1545

Val Ala Thr Glu Ser Ser Ala Lys Thr Pro Ser Lys Leu Leu Asp
    1550            1555            1560

Pro Leu Ala Trp Asp Asn His Tyr Gly Thr Gln Ile Pro Lys Glu
    1565            1570            1575

Glu Trp Lys Ser Gln Glu Lys Ser Pro Glu Lys Thr Ala Phe Lys
    1580            1585            1590

Lys Lys Asp Thr Ile Leu Ser Leu Asn Ala Cys Glu Ser Asn His
    1595            1600            1605

Ala Ile Ala Ala Ile Asn Glu Gly Gln Asn Lys Pro Glu Ile Glu
    1610            1615            1620

Val Thr Trp Ala Lys Gln Gly Arg Thr Glu Arg Leu Cys Ser Gln
    1625            1630            1635

Asn Pro Pro Val Leu Lys Arg His Gln Arg Glu Ile Thr Arg Thr
    1640            1645            1650

Thr Leu Gln Ser Asp Gln Glu Glu Ile Asp Tyr Asp Asp Thr Ile
    1655            1660            1665

Ser Val Glu Met Lys Lys Glu Asp Phe Asp Ile Tyr Asp Glu Asp
    1670            1675            1680

Glu Asn Gln Ser Pro Arg Ser Phe Gln Lys Lys Thr Arg His Tyr
    1685            1690            1695

Phe Ile Ala Ala Val Glu Arg Leu Trp Asp Tyr Gly Met Ser Ser
    1700            1705            1710

Ser Pro His Val Leu Arg Asn Arg Ala Gln Ser Gly Ser Val Pro
    1715            1720            1725

Gln Phe Lys Lys Val Val Phe Gln Glu Phe Thr Asp Gly Ser Phe
    1730            1735            1740

Thr Gln Pro Leu Tyr Arg Gly Glu Leu Asn Glu His Leu Gly Leu
    1745            1750            1755
```

```
Leu Gly Pro Tyr Ile Arg Ala Glu Val Glu Asp Asn Ile Met Val
    1760            1765                1770

Thr Phe Arg Asn Gln Ala Ser Arg Pro Tyr Ser Phe Tyr Ser Ser
    1775            1780                1785

Leu Ile Ser Tyr Glu Glu Asp Gln Arg Gln Gly Ala Glu Pro Arg
    1790            1795                1800

Lys Asn Phe Val Lys Pro Asn Glu Thr Lys Thr Tyr Phe Trp Lys
    1805            1810                1815

Val Gln His His Met Ala Pro Thr Lys Asp Glu Phe Asp Cys Lys
    1820            1825                1830

Ala Trp Ala Tyr Phe Ser Asp Val Asp Leu Glu Lys Asp Val His
    1835            1840                1845

Ser Gly Leu Ile Gly Pro Leu Leu Val Cys His Thr Asn Thr Leu
    1850            1855                1860

Asn Pro Ala His Gly Arg Gln Val Thr Val Gln Glu Phe Ala Leu
    1865            1870                1875

Phe Phe Thr Ile Phe Asp Glu Thr Lys Ser Trp Tyr Phe Thr Glu
    1880            1885                1890

Asn Met Glu Arg Asn Cys Arg Ala Pro Cys Asn Ile Gln Met Glu
    1895            1900                1905

Asp Pro Thr Phe Lys Glu Asn Tyr Arg Phe His Ala Ile Asn Gly
    1910            1915                1920

Tyr Ile Met Asp Thr Leu Pro Gly Leu Val Met Ala Gln Asp Gln
    1925            1930                1935

Arg Ile Arg Trp Tyr Leu Leu Ser Met Gly Ser Asn Glu Asn Ile
    1940            1945                1950

His Ser Ile His Phe Ser Gly His Val Phe Thr Val Arg Lys Lys
    1955            1960                1965

Glu Glu Tyr Lys Met Ala Leu Tyr Asn Leu Tyr Pro Gly Val Phe
    1970            1975                1980

Glu Thr Val Glu Met Leu Pro Ser Lys Ala Gly Ile Trp Arg Val
    1985            1990                1995

Glu Cys Leu Ile Gly Glu His Leu His Ala Gly Met Ser Thr Leu
    2000            2005                2010

Phe Leu Val Tyr Ser Asn Lys Cys Gln Thr Pro Leu Gly Met Ala
    2015            2020                2025

Ser Gly His Ile Arg Asp Phe Gln Ile Thr Ala Ser Gly Gln Tyr
    2030            2035                2040

Gly Gln Trp Ala Pro Lys Leu Ala Arg Leu His Tyr Ser Gly Ser
    2045            2050                2055

Ile Asn Ala Trp Ser Thr Lys Glu Pro Phe Ser Trp Ile Lys Val
    2060            2065                2070

Asp Leu Leu Ala Pro Met Ile Ile His Gly Ile Lys Thr Gln Gly
    2075            2080                2085

Ala Arg Gln Lys Phe Ser Ser Leu Tyr Ile Ser Gln Phe Ile Ile
    2090            2095                2100

Met Tyr Ser Leu Asp Gly Lys Lys Trp Gln Thr Tyr Arg Gly Asn
    2105            2110                2115

Ser Thr Gly Thr Leu Met Val Phe Phe Gly Asn Val Asp Ser Ser
    2120            2125                2130

Gly Ile Lys His Asn Ile Phe Asn Pro Pro Ile Ile Ala Arg Tyr
    2135            2140                2145

Ile Arg Leu His Pro Thr His Tyr Ser Ile Arg Ser Thr Leu Arg
```

```
                2150                2155                2160
Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330

<210> SEQ ID NO 2
<211> LENGTH: 1438
<212> TYPE: PRT
<213> ORGANISM: Artificial Sequence
<220> FEATURE:
<223> OTHER INFORMATION: BDD FVIII

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
```

```
                       165                 170                 175
Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590
```

```
Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                    645                 650                 655

Thr Phe Lys His Lys Met Val Tyr Glu Asp Thr Leu Thr Leu Phe Pro
                    660                 665                 670

Phe Ser Gly Glu Thr Val Phe Met Ser Met Glu Asn Pro Gly Leu Trp
                    675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                    725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
            755                 760                 765

Asp Tyr Asp Asp Thr Ile Ser Val Glu Met Lys Lys Glu Asp Phe Asp
            770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                    805                 810                 815

Met Ser Ser Ser Pro His Val Leu Arg Asn Arg Ala Gln Ser Gly Ser
                    820                 825                 830

Val Pro Gln Phe Lys Lys Val Val Phe Gln Glu Phe Thr Asp Gly Ser
            835                 840                 845

Phe Thr Gln Pro Leu Tyr Arg Gly Glu Leu Asn Glu His Leu Gly Leu
            850                 855                 860

Leu Gly Pro Tyr Ile Arg Ala Glu Val Glu Asp Asn Ile Met Val Thr
865                 870                 875                 880

Phe Arg Asn Gln Ala Ser Arg Pro Tyr Ser Phe Tyr Ser Ser Leu Ile
                    885                 890                 895

Ser Tyr Glu Glu Asp Gln Arg Gln Gly Ala Glu Pro Arg Lys Asn Phe
                    900                 905                 910

Val Lys Pro Asn Glu Thr Lys Thr Tyr Phe Trp Lys Val Gln His His
            915                 920                 925

Met Ala Pro Thr Lys Asp Glu Phe Asp Cys Lys Ala Trp Ala Tyr Phe
            930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
                    965                 970                 975

Val Thr Val Gln Glu Phe Ala Leu Phe Leu Thr Ile Phe Asp Glu Thr
                    980                 985                 990

Lys Ser Trp Tyr Phe Thr Glu Asn Met Glu Arg Asn Cys Arg Ala Pro
            995                 1000                1005
```

-continued

```
Cys Asn Ile Gln Met Glu Asp Pro Thr Phe Lys Glu Asn Tyr Arg
1010                1015                1020

Phe His Ala Ile Asn Gly Tyr Ile Met Asp Thr Leu Pro Gly Leu
1025                1030                1035

Val Met Ala Gln Asp Gln Arg Ile Arg Trp Tyr Leu Leu Ser Met
1040                1045                1050

Gly Ser Asn Glu Asn Ile His Ser Ile His Phe Ser Gly His Val
1055                1060                1065

Phe Thr Val Arg Lys Lys Glu Glu Tyr Lys Met Ala Leu Tyr Asn
1070                1075                1080

Leu Tyr Pro Gly Val Phe Glu Thr Val Glu Met Leu Pro Ser Lys
1085                1090                1095

Ala Gly Ile Trp Arg Val Glu Cys Leu Ile Gly Glu His Leu His
1100                1105                1110

Ala Gly Met Ser Thr Leu Phe Leu Val Tyr Ser Asn Lys Cys Gln
1115                1120                1125

Thr Pro Leu Gly Met Ala Ser Gly His Ile Arg Asp Phe Gln Ile
1130                1135                1140

Thr Ala Ser Gly Gln Tyr Gly Gln Trp Ala Pro Lys Leu Ala Arg
1145                1150                1155

Leu His Tyr Ser Gly Ser Ile Asn Ala Trp Ser Thr Lys Glu Pro
1160                1165                1170

Phe Ser Trp Ile Lys Val Asp Leu Leu Ala Pro Met Ile Ile His
1175                1180                1185

Gly Ile Lys Thr Gln Gly Ala Arg Gln Lys Phe Ser Ser Leu Tyr
1190                1195                1200

Ile Ser Gln Phe Ile Ile Met Tyr Ser Leu Asp Gly Lys Lys Trp
1205                1210                1215

Gln Thr Tyr Arg Gly Asn Ser Thr Gly Thr Leu Met Val Phe Phe
1220                1225                1230

Gly Asn Val Asp Ser Ser Gly Ile Lys His Asn Ile Phe Asn Pro
1235                1240                1245

Pro Ile Ile Ala Arg Tyr Ile Arg Leu His Pro Thr His Tyr Ser
1250                1255                1260

Ile Arg Ser Thr Leu Arg Met Glu Leu Met Gly Cys Asp Leu Asn
1265                1270                1275

Ser Cys Ser Met Pro Leu Gly Met Glu Ser Lys Ala Ile Ser Asp
1280                1285                1290

Ala Gln Ile Thr Ala Ser Ser Tyr Phe Thr Asn Met Phe Ala Thr
1295                1300                1305

Trp Ser Pro Ser Lys Ala Arg Leu His Leu Gln Gly Arg Ser Asn
1310                1315                1320

Ala Trp Arg Pro Gln Val Asn Asn Pro Lys Glu Trp Leu Gln Val
1325                1330                1335

Asp Phe Gln Lys Thr Met Lys Val Thr Gly Val Thr Thr Gln Gly
1340                1345                1350

Val Lys Ser Leu Leu Thr Ser Met Tyr Val Lys Glu Phe Leu Ile
1355                1360                1365

Ser Ser Ser Gln Asp Gly His Gln Trp Thr Leu Phe Phe Gln Asn
1370                1375                1380

Gly Lys Val Lys Val Phe Gln Gly Asn Gln Asp Ser Phe Thr Pro
1385                1390                1395

Val Val Asn Ser Leu Asp Pro Pro Leu Leu Thr Arg Tyr Leu Arg
```

-continued

```
                1400                1405                1410

Ile His Pro Gln Ser Trp Val His Gln Ile Ala Leu Arg Met Glu
    1415                1420                1425

Val Leu Gly Cys Glu Ala Gln Asp Leu Tyr
    1430                1435

<210> SEQ ID NO 3
<211> LENGTH: 754
<212> TYPE: PRT
<213> ORGANISM: Artificial Sequence
<220> FEATURE:
<223> OTHER INFORMATION: BDD FVIII

<400> SEQUENCE: 3

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
```

```
                        325                 330                 335
Met Lys Asn Asn Glu Glu Ala Glu Asp Tyr Asp Asp Leu Thr Asp
                340                 345                 350

Ser Glu Met Asp Val Val Arg Phe Asp Asp Asn Ser Pro Ser Phe
                355                 360                 365

Ile Gln Ile Arg Ser Val Ala Lys Lys His Pro Lys Thr Trp Val His
        370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
                435                 440                 445

Leu Gly Pro Leu Leu Tyr Gly Glu Val Gly Asp Thr Leu Leu Ile Ile
                450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
                515                 520                 525

Leu Thr Arg Tyr Tyr Ser Ser Phe Val Asn Met Glu Arg Asp Leu Ala
                530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
                610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
                675                 680                 685

Ile Leu Gly Cys His Asn Ser Asp Phe Arg Asn Arg Gly Met Thr Ala
                690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
                740                 745                 750
```

Gln Arg

<210> SEQ ID NO 4
<211> LENGTH: 684
<212> TYPE: PRT
<213> ORGANISM: Artificial Sequence
<220> FEATURE:
<223> OTHER INFORMATION: BDD FVIII

<400> SEQUENCE: 4

```
Glu Ile Thr Arg Thr Thr Leu Gln Ser Asp Gln Glu Glu Ile Asp Tyr
1               5                   10                  15

Asp Asp Thr Ile Ser Val Glu Met Lys Lys Asp Phe Asp Ile Tyr
            20                  25                  30

Asp Glu Asp Glu Asn Gln Ser Pro Arg Ser Phe Gln Lys Lys Thr Arg
        35                  40                  45

His Tyr Phe Ile Ala Ala Val Glu Arg Leu Trp Asp Tyr Gly Met Ser
    50                  55                  60

Ser Ser Pro His Val Leu Arg Asn Arg Ala Gln Ser Gly Ser Val Pro
65                  70                  75                  80

Gln Phe Lys Lys Val Val Phe Gln Glu Phe Thr Asp Gly Ser Phe Thr
                85                  90                  95

Gln Pro Leu Tyr Arg Gly Glu Leu Asn Glu His Leu Gly Leu Leu Gly
            100                 105                 110

Pro Tyr Ile Arg Ala Glu Val Glu Asp Asn Ile Met Val Thr Phe Arg
        115                 120                 125

Asn Gln Ala Ser Arg Pro Tyr Ser Phe Tyr Ser Ser Leu Ile Ser Tyr
    130                 135                 140

Glu Glu Asp Gln Arg Gln Gly Ala Glu Pro Arg Lys Asn Phe Val Lys
145                 150                 155                 160

Pro Asn Glu Thr Lys Thr Tyr Phe Trp Lys Val Gln His His Met Ala
                165                 170                 175

Pro Thr Lys Asp Glu Phe Asp Cys Lys Ala Trp Ala Tyr Phe Ser Asp
            180                 185                 190

Val Asp Leu Glu Lys Asp Val His Ser Gly Leu Ile Gly Pro Leu Leu
        195                 200                 205

Val Cys His Thr Asn Thr Leu Asn Pro Ala His Gly Arg Gln Val Thr
    210                 215                 220

Val Gln Glu Phe Ala Leu Phe Leu Thr Ile Phe Asp Glu Thr Lys Ser
225                 230                 235                 240

Trp Tyr Phe Thr Glu Asn Met Glu Arg Asn Cys Arg Ala Pro Cys Asn
                245                 250                 255

Ile Gln Met Glu Asp Pro Thr Phe Lys Glu Asn Tyr Arg Phe His Ala
            260                 265                 270

Ile Asn Gly Tyr Ile Met Asp Thr Leu Pro Gly Leu Val Met Ala Gln
        275                 280                 285

Asp Gln Arg Ile Arg Trp Tyr Leu Leu Ser Met Gly Ser Asn Glu Asn
    290                 295                 300

Ile His Ser Ile His Phe Ser Gly His Val Phe Thr Val Arg Lys Lys
305                 310                 315                 320

Glu Glu Tyr Lys Met Ala Leu Tyr Asn Leu Tyr Pro Gly Val Phe Glu
                325                 330                 335

Thr Val Glu Met Leu Pro Ser Lys Ala Gly Ile Trp Arg Val Glu Cys
            340                 345                 350
```

```
Leu Ile Gly Glu His Leu His Ala Gly Met Ser Thr Leu Phe Leu Val
            355                 360                 365

Tyr Ser Asn Lys Cys Gln Thr Pro Leu Gly Met Ala Ser Gly His Ile
370                 375                 380

Arg Asp Phe Gln Ile Thr Ala Ser Gly Gln Tyr Gly Gln Trp Ala Pro
385                 390                 395                 400

Lys Leu Ala Arg Leu His Tyr Ser Gly Ser Ile Asn Ala Trp Ser Thr
            405                 410                 415

Lys Glu Pro Phe Ser Trp Ile Lys Val Asp Leu Leu Ala Pro Met Ile
            420                 425                 430

Ile His Gly Ile Lys Thr Gln Gly Ala Arg Gln Lys Phe Ser Ser Leu
            435                 440                 445

Tyr Ile Ser Gln Phe Ile Ile Met Tyr Ser Leu Asp Gly Lys Lys Trp
450                 455                 460

Gln Thr Tyr Arg Gly Asn Ser Thr Gly Thr Leu Met Val Phe Phe Gly
465                 470                 475                 480

Asn Val Asp Ser Ser Gly Ile Lys His Asn Ile Phe Asn Pro Pro Ile
            485                 490                 495

Ile Ala Arg Tyr Ile Arg Leu His Pro Thr His Tyr Ser Ile Arg Ser
            500                 505                 510

Thr Leu Arg Met Glu Leu Met Gly Cys Asp Leu Asn Ser Cys Ser Met
515                 520                 525

Pro Leu Gly Met Glu Ser Lys Ala Ile Ser Asp Ala Gln Ile Thr Ala
            530                 535                 540

Ser Ser Tyr Phe Thr Asn Met Phe Ala Thr Trp Ser Pro Ser Lys Ala
545                 550                 555                 560

Arg Leu His Leu Gln Gly Arg Ser Asn Ala Trp Arg Pro Gln Val Asn
            565                 570                 575

Asn Pro Lys Glu Trp Leu Gln Val Asp Phe Gln Lys Thr Met Lys Val
            580                 585                 590

Thr Gly Val Thr Thr Gln Gly Val Lys Ser Leu Leu Thr Ser Met Tyr
            595                 600                 605

Val Lys Glu Phe Leu Ile Ser Ser Ser Gln Asp Gly His Gln Trp Thr
610                 615                 620

Leu Phe Phe Gln Asn Gly Lys Val Lys Val Phe Gln Gly Asn Gln Asp
625                 630                 635                 640

Ser Phe Thr Pro Val Val Asn Ser Leu Asp Pro Pro Leu Leu Thr Arg
            645                 650                 655

Tyr Leu Arg Ile His Pro Gln Ser Trp Val His Gln Ile Ala Leu Arg
            660                 665                 670

Met Glu Val Leu Gly Cys Glu Ala Gln Asp Leu Tyr
            675                 680

<210> SEQ ID NO 5
<211> LENGTH: 14
<212> TYPE: PRT
<213> ORGANISM: Artificial Sequence
<220> FEATURE:
<223> OTHER INFORMATION: Partial B domain

<400> SEQUENCE: 5

Ser Phe Ser Gln Asn Pro Pro Val Leu Lys Arg His Gln Arg
1               5                   10

<210> SEQ ID NO 6
<211> LENGTH: 9048
```

```
<212> TYPE: DNA
<213> ORGANISM: Homo sapiens

<400> SEQUENCE: 6
gcttagtgct gagcacatcc agtgggtaaa gttccttaaa atgctctgca aagaaattgg      60
gacttttcat taaatcagaa attttacttt ttccctcc tgggagctaa agatatttta      120
gagaagaatt aaccttttgc ttctccagtt gaacatttgt agcaataagt catgcaaata      180
gagctctcca cctgcttctt tctgtgcctt ttgcgattct gctttagtgc caccagaaga      240
tactacctgg gtgcagtgga actgtcatgg gactatatgc aaagtgatct cggtgagctg      300
cctgtggacg caagatttcc tcctagagtg ccaaaatctt ttccattcaa cacctcagtc      360
gtgtacaaaa agactctgtt tgtagaattc acggatcacc ttttcaacat cgctaagcca      420
aggccaccct ggatgggtct gctaggtcct accatccagg ctgaggttta tgatacagtg      480
gtcattacac ttaagaacat ggcttcccat cctgtcagtc ttcatgctgt tggtgtatcc      540
tactggaaag cttctgaggg agctgaatat gatgatcaga ccagtcaaag ggagaaagaa      600
gatgataaag tcttccctgg tggaagccat acatatgtct ggcaggtcct gaaagagaat      660
ggtccaatgg cctctgaccc actgtgcctt acctactcat atctttctca tgtggacctg      720
gtaaaagact tgaattcagg cctcattgga gccctactag tatgtagaga agggagtctg      780
gccaaggaaa agacacagac cttgcacaaa tttatactac tttttgctgt atttgatgaa      840
gggaaaagtt ggcactcaga aacaaagaac tccttgatgc aggatagga tgctgcatct      900 gctcgggcct ggcctaaaat gcacacagtc aatggttatg taaacaggtc tctgccaggt      960
ctgattggat gccacaggaa atcagtctat tggcatgtga ttggaatggg caccactcct     1020
gaagtgcact caatattcct cgaaggtcac acatttcttg tgaggaacca tcgccaggcg     1080
tccttggaaa tctcgccaat aactttcctt actgctcaaa cactcttgat ggaccttgga     1140
cagtttctac tgttttgtca tatctcttcc caccaacatg atggcatgga agcttatgtc     1200
aaagtagaca gctgtccaga ggaaccccaa ctacgaatga aaaataatga agaagcggaa     1260
gactatgatg atgatcttac tgattctgaa atggatgtgg tcaggtttga tgatgacaac     1320
tctccttcct ttatccaaat tcgctcagtt gccaagaagc atcctaaaac ttgggtacat     1380
tacattgctg ctgaagagga ggactgggac tatgctccct tagtcctcgc ccccgatgac     1440
agaagttata aaagtcaata tttgaacaat ggccctcagc ggattggtag aagtacaaa     1500 aaagtccgat ttatggcata cacagatgaa acctttaaga ctcgtgaagc tattcagcat     1560
gaatcaggaa tcttgggacc tttactttat ggggaagttg agacacact gttgattata     1620 tttaagaatc aagcaagcag accatataac atctaccctc acggaatcac tgatgtccgt     1680
cctttgtatt caaggagatt accaaaaggt gtaaaacatt tgaaggattt tccaattctg     1740
ccaggagaaa tattcaaata taatggaca gtgactgtag aagatgggcc aactaaatca     1800
gatcctcggt gcctgacccg ctattactct agtttcgtta atatgagag atctagct     1860 tcaggactca ttggccctct cctcatctgc tacaaagaat ctgtagatca agaggaaac     1920 cagataatgt cagacaagag gaatgtcatc ctgttttctg tatttgatga aaccgaagc     1980 tggtacctca cagagaatat acaacgcttt ctccccaatc cagctggagt gcagcttgag     2040
gatccagagt ccaagcctc caacatcatg cacagcatca atggctatgt ttttgatagt     2100
ttgcagttgt cagtttgttt gcatgaggtg gcatactggg acattctaag cattggagca     2160
cagactgact tcctttctgt cttcttctct ggatatacct tcaaacacaa aatggtctat     2220
```

```
gaagacacac tcaccctatt cccattctca ggagaaactg tcttcatgtc gatggaaaac    2280
ccaggtctat ggattctggg gtgccacaac tcagactttc ggaacagagg catgaccgcc    2340
ttactgaagg tttctagttg tgacaagaac actggtgatt attacgagga cagttatgaa    2400
gatatttcag catacttgct gagtaaaaac aatgccattg aaccaagaag cttctcccag    2460
aattcaagac accctagcac taggcaaaag caatttaatg ccaccacaat tccagaaaat    2520
gacatagaga agactgaccc ttggtttgca cacagaacac ctatgcctaa aatacaaaat    2580
gtctcctcta gtgatttgtt gatgctcttg cgacagagtc ctactccaca tgggctatcc    2640
ttatctgatc tccaagaagc caaatatgag acttttctg atgatccatc acctggagca    2700
atagacagta ataacagcct gtctgaaatg acacacttca ggccacagct ccatcacagt    2760
ggggacatgg tatttacccc tgagtcaggc ctccaattaa gattaaatga gaaactgggg    2820
acaactgcag caacagagtt gaagaaactt gatttcaaag tttctagtac atcaaataat    2880
ctgatttcaa caattccatc agacaatttg gcagcaggta ctgataatac aagttcctta    2940 ggaccccaa gtatgccagt tcattatgat agtcaattag ataccactct atttggcaaa    3000
aagtcatctc cccttactga gtctggtgga cctctgagct tgagtgaaga aaataatgat    3060
tcaaagttgt tagaatcagg tttaatgaat agccaagaaa gttcatgggg aaaaaatgta    3120
tcgtcaacag agagtggtag gttatttaaa gggaaaagag ctcatggacc tgctttgttg    3180 actaagata atgccttatt caagttagc atctctttgt taaagacaaa caaaacttcc    3240
aataattcag caactaatag aaagactcac attgatggcc catcattatt aattgagaat    3300
agtccatcag tctggcaaaa tatattagaa agtgacactg agtttaaaaa agtgacacct    3360
ttgattcatg acagaatgct tatggacaaa aatgctacag ctttgaggct aaatcatatg    3420
tcaaataaaa ctacttcatc aaaaaacatg gaaatggtcc aacagaaaaa agagggcccc    3480
attccaccag atgcacaaaa tccagatatg tcgttctta agatgctatt cttgccagaa    3540
tcagcaaggt ggatacaaag gactcatgga agaactctc tgaactctgg gcaaggcccc    3600
agtccaaagc aattagtatc cttaggacca gaaaaatctg tggaaggtca gaatttcttg    3660
tctgagaaaa acaaagtggt agtaggaaag ggtgaattta caaggacgt aggactcaaa    3720 gagatggttt ttccaagcag cagaaaccta tttcttacta acttggataa tttacatgaa    3780
aataatacac acaatcaaga aaaaaaaatt caggaagaaa tagaaaagaa ggaaacatta    3840
atccaagaga atgtagtttt gcctcagata catacagtga ctggcactaa gaatttcatg    3900
aagaaccttt tcttactgag cactaggcaa aatgtagaag gttcatatga cggggcatat    3960
gctccagtac ttcaagattt taggtcatta aatgattcaa caaatagaac aaagaaacac    4020
acagctcatt tctcaaaaaa agggggaggaa gaaaacttgg aaggcttggg aaatcaaacc    4080
aagcaaattg tagagaaata tgcatgcacc acaaggatat ctcctaatac aagccagcag    4140
aattttgtca cgcaacgtag taagagagct ttgaaacaat tcagactccc actgaagaa    4200 acagaacttg aaaaaaggat aattgtggat gacacctcaa cccagtggtc caaaaacatg    4260
aaacatttga ccccgagcac cctcacacag atagactaca atgagaagga gaagggggcc    4320
attactcagt ctcccttatc agattgcctt acgaggagtc atagcatccc tcaagcaaat    4380
agatctccat tacccattgc aaaggtatca tcatttccat ctattagacc tatatatctg    4440
accagggtcc tattccaaga caactcttct catcttccag cagcatctta tagaaagaaa    4500
gattctgggg tccaagaaag cagtcatttc ttacaaggga ccaaaaaaaa taacctttct    4560
ttagccattc taaccttgga gatgactggt gatcaaagag aggttggctc cctggggaca    4620
```

```
agtgccacaa attcagtcac atacaagaaa gttgagaaca ctgttctccc gaaaccagac    4680
ttgcccaaaa catctggcaa agttgaattg cttccaaaag ttcacattta tcagaaggac    4740
ctattcccta cggaaactag caatgggtct cctggccatc tggatctcgt ggaagggagc    4800
cttcttcagg gaacagaggg agcgattaag tggaatgaag caaacagacc tggaaaagtt    4860 cccttctga gagtagcaac agaaagctct gcaaagactc cctccaagct attggatcct    4920
cttgcttggg ataaccacta tggtactcag ataccaaaag aagagtggaa atcccaagag    4980
aagtcaccag aaaaaacagc ttttaagaaa aaggatacca ttttgtccct gaacgcttgt    5040
gaaagcaatc atgcaatagc agcaataaat gagggacaaa ataagcccga aatagaagtc    5100
acctgggcaa agcaaggtag gactgaaagg ctgtgctctc aaaacccacc agtcttgaaa    5160
cgccatcaac gggaaataac tcgtactact cttcagtcag atcaagagga aattgactat    5220
gatgatacca tatcagttga aatgaagaag gaagattttg acatttatga tgaggatgaa    5280
aatcagagcc cccgcagctt tcaaaagaaa acacgacact atttattgc tgcagtggag    5340 aggctctggg attatgggat gagtagctcc ccacatgttc taagaaacag ggctcagagt    5400
ggcagtgtcc ctcagttcaa gaaagttgtt ttccaggaat ttactgatgg ctcctttact    5460
cagcccttat accgtggaga actaaatgaa catttgggac tcctggggcc atatataaga    5520
gcagaagttg aagataatat catggtaact ttcagaaatc aggcctctcg tccctattcc    5580
ttctattcta gccttatttc ttatgaggaa gatcagaggc aaggagcaga acctagaaaa    5640
aactttgtca gcctaatga aaccaaaact tactttggaa agtgcaaca tcatatggca    5700 cccactaaag atgagtttga ctgcaaagcc tgggcttatt tctctgatgt tgacctggaa    5760
aaagatgtgc actcaggcct gattggaccc cttctggtct gccacactaa cacactgaac    5820
cctgctcatg ggagacaagt gacagtacag gaatttgctc tgttttcac catctttgat    5880 gagaccaaaa gctggtactt cactgaaaat atggaaagaa actgcagggc tccctgcaat    5940
atccagatgg aagatcccac ttttaaagag aattatcgct tccatgcaat caatggctac    6000
ataatggata cactacctgg cttagtaatg gctcaggatc aaaggattcg atggtatctg    6060
ctcagcatgg gcagcaatga aaacatccat tctattcatt tcagtggaca tgtgttcact    6120
gtacgaaaaa aagaggagta taaaatggca ctgtacaatc tctatccagg tgttttgag    6180 acagtggaaa tgttaccatc caaagctgga atttggcggg tggaatgcct tattggcgag    6240
catctacatg ctgggatgag cacacttttt ctggtgtaca gcaataagtg tcagactccc    6300
ctgggaatgg cttctggaca cattagagat tttcagatta cagcttcagg acaatatgga    6360
cagtgggccc caaagctggc cagacttcat tattccggat caatcaatgc ctggagcacc    6420 aaggagcct tttcttggat caaggtggat ctgttggcac caatgattat tcacggcatc    6480
aagacccagg gtgcccgtca gaagttctcc agcctctaca tctctcagtt tatcatcatg    6540
tatagtcttg atgggaagaa gtggcagact tatcgaggaa attccactgg aaccttaatg    6600
gtcttctttg gcaatgtgga ttcatctggg ataaaacaca tatttttaa ccctccaatt    6660 attgctcgat acatccgttt gcacccaact cattatagca ttcgcagcac tcttcgcatg    6720
gagttgatgg gctgtgattt aaatagttgc agcatgccat gggaatgga gagtaaagca    6780 atatcagatg cacagattac tgcttcatcc tactttacca atatgtttgc cacctggtct    6840
ccttcaaaag ctcgacttca cctccaaggg aggagtaatg cctggagacc tcaggtgaat    6900
aatccaaaag agtggctgca agtggacttc cagaagacaa tgaaagtcac aggagtaact    6960
```

```
actcaggag taaaatctct gcttaccagc atgtatgtga aggagttcct catctccagc    7020
agtcaagatg gccatcagtg gactctcttt tttcagaatg gcaaagtaaa ggttttttcag   7080 ggaaatcaag actccttcac acctgtggtg aactctctag acccaccgtt actgactcgc    7140
taccttcgaa ttcaccccca gagttgggtg caccagattg ccctgaggat ggaggttctg    7200
ggctgcgagg cacaggacct ctactgaggg tggccactgc agcacctgcc actgccgtca    7260
cctctccctc ctcagctcca gggcagtgtc cctccctggc ttgccttcta cctttgtgct    7320
aaatcctagc agacactgcc ttgaagcctc ctgaattaac tatcatcagt cctgcatttc    7380
tttggtgggg ggccaggagg gtgcatccaa tttaacttaa ctcttaccta ttttctgcag    7440
ctgctcccag attactcctt ccttccaata taactaggca aaagaagtg aggagaaacc     7500 tgcatgaaag cattcttccc tgaaaagtta ggcctctcag agtcaccact tcctctgttg    7560
tagaaaaact atgtgatgaa actttgaaaa agatatttat gatgttaaca tttcaggtta    7620
agcctcatac gttaaaaata aaactctcag ttgtttatta tcctgatcaa gcatggaaca    7680
aagcatgttt caggatcaga tcaatacaat cttggagtca aaaggcaaat catttggaca    7740
atctgcaaaa tggagagaat acaataacta ctacagtaaa gtctgtttct gcttccttac    7800
acatagatat aattatgtta tttagtcatt atgagggca cattcttatc tccaaaacta    7860
gcattcttaa actgagaatt atagatgggg ttcaagaatc cctaagtccc ctgaaattat    7920
ataaggcatt ctgtataaat gcaaatgtgc atttttctga cgagtgtcca tagatataaa    7980
gccatttggt cttaattctg accaataaaa aaataagtca ggaggatgca attgttgaaa    8040
gctttgaaat aaaataacaa tgtcttcttg aaatttgtga tggccaagaa agaaaatgat    8100
gatgacatta ggcttctaaa ggacatacat ttaatatttc tgtggaaata tgaggaaaat    8160
ccatggttat ctgagatagg agatacaaac tttgtaattc taataatgca ctcagtttac    8220
tctctccctc tactaatttc ctgctgaaaa taacacaaca aaaatgtaac aggggaaatt    8280
atataccgtg actgaaaact agagtcctac ttacatagtt gaaatatcaa ggaggtcaga    8340
agaaaattgg actggtgaaa acagaaaaaa cactccagtc tgccatatca ccacacaata    8400
ggatccccct tcttgccctc cacccccata agattgtgaa gggtttactg ctcccttccat   8460 ctgcctgacc ccttcactat gactacacag aatctcctga tagtaaaggg ggctggaggc    8520
aaggataagt tatagagcag ttggaggaag catccaaaga ttgcaaccca gggcaaatgg    8580
aaaacaggag atcctaatat gaaagaaaaa tggatcccaa tctgagaaaa ggcaaaagaa    8640
tggctacttt tttctatgct ggagtatttt ctaataatcc tgcttgaccc ttatctgacc    8700
tctttggaaa ctataacata gctgtcacag tatagtcaca atccacaaat gatgcaggtg    8760
caaatggttt atagccctgt gaagttctta aagtttagag gctaacttac agaaatgaat    8820
aagttgtttt gttttatagc ccggtagagg agttaacccc aaaggtgata tggttttatt    8880
tcctgttatg tttaacttga taatcttatt ttggcattct tttcccattg actatataca    8940
tctctatttc tcaaatgttc atggaactag ctcttttatt ttcctgctgg tttcttcagt    9000
aatgagttaa ataaaacatt gacacataca aacaaaaaaa aaaaaaaa                 9048
```

<210> SEQ ID NO 7
<211> LENGTH: 4410
<212> TYPE: DNA
<213> ORGANISM: Artificial Sequence
<220> FEATURE:
<223> OTHER INFORMATION: BDD FVIII cDNA

<400> SEQUENCE: 7

-continued

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaaatcttt tccattcaac     180
acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg cttcccatc ctgtcagtct tcatgctgtt      360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggatagggat     720
gctgcatctg ctcgggcctg gcctaaaatg cacacagtca atggttatgt aaacaggtct     780
ctaccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt cctggaaat ctcgccaata actttcctta ctgctcaaac actcttgatg      960
gaccttggac agtttctact gttttgtcat atctcttccc accaacatga tggcatggaa    1020
gcttatgtca aagtagacag ctgtccagag gaaccccaac tacgaatgaa aaataatgaa    1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctcccct agtcctcgcc    1260
cccgatgaca aagttataa aagtcaatat ttgaacaatg ccctcagcg gattggtagg      1320 aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt ccttttctgtc ttcttctctg atataccttt caaacacaaa    2040
atggtctatg aagacacact caccctattc ccattctcag agaaactgt cttcatgtcg     2100 atggaaaacc aggtctatg gattctgggg tgccacaact cagactttcg aacagaggc     2160 atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctctcaga atccaccagt cttgaaacgc catcaacggg aaataactcg tactactctt    2340
```

```
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata taagagcaa gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat tggacccctt    2940
ctggtctgcc acactaacac actgaaccct gctcatggga gacaagtgac agtacaggaa    3000
tttgctctgt ttctcaccat ctttgatgag accaaaagct ggtacttcac tgaaaatatg    3060
gaaagaaact gcagggctcc ctgcaatatc cagatggaag atcccacttt taagagaat    3120 tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa gctggaatt    3360 tggcgggtgg aatgccttat tggcgagcat ctacatgctg ggatgagcac actttttctg    3420
gtgtacagca ataagtgtca gactcccctg ggaatggctt ctggacacat tagagatttt    3480
cagattacag cttcaggaca atatggacag tgggcccaa agctggccag acttcattat    3540
tccggatcaa tcaatgcctg gagcaccaag gagccctttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg ggaagaagtg gcagacttat    3720
cgaggaaatt ccactggaac cttaatggtc ttctttggca atgtggattc atctgggata    3780
aaacacaata ttttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga agtcacagg agtaactact cagggagtaa aatctctgct taccagcatg    4140
tatgtgaagg agttcctcat ctccagcagt caagatggcc atcagtggac tctctttttt    4200
cagaatggca agtaaaggt ttttcaggga aatcaagact ccttcacacc tgtggtgaac    4260
tctctagacc caccgttact gactcgctac cttcgaattc accccagag ttgggtgcac    4320 cagattgccc tgaggatgga ggttctgggc tgcgaggcac aggacctcta cggaggcggt    4380
ggggactaca aggacgatga cgacaagtaa                                      4410
```

<210> SEQ ID NO 8
<211> LENGTH: 4374
<212> TYPE: DNA
<213> ORGANISM: Artificial Sequence
<220> FEATURE:
<223> OTHER INFORMATION: BDD FVIII cDNA

<400> SEQUENCE: 8

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaaatcttt tccattcaac     180
acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaagacttt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggatagggat     720
gctgcatctg ctcgggcctg gcctaaaatg cacacagtca atggttatgt aaacaggtct     780
ctaccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt cctggaaaat ctcgccaata actttcctta ctgctcaaac actcttgatg     960
gaccttggac agtttctact gttttgtcat atctcttccc accaacatga tggcatggaa    1020
gcttatgtca aagtagacag ctgtccagag gaaccccaac tacgaatgaa aaataatgaa    1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctcccct tagtcctcgcc   1260 cccgatgaca aagttataa aagtcaatat ttgaacaatg gccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaagaaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg atataccttt caaacacaaa    2040
atggtctatg aagacacact caccctattc ccattctcag agaaactgt cttcatgtcg    2100 atggaaaacc aggtctatg gattctgggg tgccacaact cagactttcg aacagaggc    2160 atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctctcaga atccaccagt cttgaaacgc catcaacggg aaataactcg tactactctt    2340
```

```
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata taagagca gaagttgaag ataatatcat ggtaactttc      2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat tggacccctt    2940
ctggtctgcc acactaacac actgaaccct gctcatggga gacaagtgac agtacaggaa    3000
tttgctctgt ttctcaccat ctttgatgag accaaaagct ggtacttcac tgaaaatatg    3060
gaaagaaact gcagggctcc ctgcaatatc cagatggaag atcccacttt taagagaat    3120
tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctg     3420
gtgtacagca ataagtgtca gactcccctg ggaatggctt ctggacacat tagagatttt    3480
cagattacag cttcaggaca atatggacag tgggccccaa agctggccag acttcattat    3540
tccggatcaa tcaatgcctg gagcaccaag gagcccttt cttggatcaa ggtggatctg     3600
ttggcaccaa tgattattca cggcatcaag acccagggtg cccgtcagaa gttctccagc    3660
ctctacatct ctcagtttat catcatgtat agtcttgatg gaagaagtg gcagacttat     3720
cgaggaaatt ccactggaac cttaatggtc ttctttggca atgtggattc atctgggata    3780
aaacacaata tttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga aagtcacagg agtaactact cagggagtaa aatctctgct taccagcatg    4140
tatgtgaagg agttcctcat ctccagcagt caagatggcc atcagtggac tctcttttt     4200
cagaatggca agtaaaggt ttttcaggga aatcaagact ccttcacacc tgtggtgaac    4260
tctctagacc caccgttact gactcgctac cttcgaattc accccagag ttgggtgcac     4320
cagattgccc tgaggatgga ggttctgggc tgcgaggcac aggacctcta ctaa           4374
```